(12) United States Patent
Wang et al.

(10) Patent No.: US 7,465,415 B2
(45) Date of Patent: Dec. 16, 2008

(54) PHOTOCHROMIC MATERIALS DERIVED FROM RING-OPENING MONOMERS AND PHOTOCHROMIC INITIATORS

(75) Inventors: Feng Wang, Export, PA (US); Barry Van Gemert, Murrysville, PA (US); Kevin J. Stewart, Murrysville, PA (US); Carol L. Knox, Monroeville, PA (US); Anu Chopra, Pittsburgh, PA (US); Patrick M. Brown, Moon Township, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 377 days.

(21) Appl. No.: 10/903,770

(22) Filed: Jul. 30, 2004

(65) Prior Publication Data

US 2006/0022176 A1     Feb. 2, 2006

(51) Int. Cl.
*C09K 9/02* (2006.01)
*C08G 63/08* (2006.01)
*C08G 63/58* (2006.01)
*C08G 77/60* (2006.01)
*C08F 24/00* (2006.01)

(52) U.S. Cl. ............... 252/586; 252/583; 525/415; 526/269; 528/35; 528/365

(58) Field of Classification Search ............ 252/583, 252/586; 525/415; 526/269; 528/35, 365
See application file for complete search history.

(56) References Cited

U.S. PATENT DOCUMENTS

| | | | |
|---|---|---|---|
| 3,933,509 A | 1/1976 | Noguchi et al. | |
| 4,289,873 A * | 9/1981 | Kubo et al. ............ | 528/357 |
| 4,719,296 A | 1/1988 | Irie et al. | |
| 4,889,413 A * | 12/1989 | Ormsby et al. ............ | 359/241 |
| 4,929,693 A | 5/1990 | Akashi et al. | |
| 4,986,934 A | 1/1991 | Kwiatkowski et al. | |
| 5,110,881 A * | 5/1992 | McBain et al. ............ | 525/455 |
| 5,166,345 A | 11/1992 | Akashi et al. | |
| 5,236,958 A | 8/1993 | Miyashita | |
| 5,252,742 A | 10/1993 | Miyashita | |
| 5,359,085 A | 10/1994 | Iwamoto et al. | |
| 5,389,287 A | 2/1995 | Nishiyama et al. | |
| 5,488,119 A | 1/1996 | Fischer-Reimann et al. | |
| 5,645,767 A | 7/1997 | Van Gemert | |
| 5,645,768 A | 7/1997 | Melzig et al. | |
| 5,770,115 A * | 6/1998 | Misura ............ | 252/586 |
| 5,821,287 A | 10/1998 | Hu et al. | |
| 5,945,488 A | 8/1999 | Gregorovich et al. | |
| 6,022,497 A | 2/2000 | Kumar | |
| 6,113,814 A | 9/2000 | Gemert et al. | |
| 6,146,554 A | 11/2000 | Melzig et al. | |
| 6,315,928 B1 | 11/2001 | Mann et al. | |
| 6,555,028 B2 | 4/2003 | Walters et al. | |
| 6,630,597 B1 | 10/2003 | Lin et al. | |
| 6,660,727 B1 | 12/2003 | Mann et al. | |
| 6,736,998 B2 | 5/2004 | Petrovskaia et al. | |
| 2001/0025948 A1 | 10/2001 | Walters et al. | |
| 2003/0141490 A1 | 7/2003 | Walters et al. | |

FOREIGN PATENT DOCUMENTS

| | | |
|---|---|---|
| EP | 0446717 A2 | 9/1991 |
| EP | 0875509 B1 | 11/1998 |
| JP | 01-026846 A | 1/1989 |
| JP | 02-042084 A | 2/1990 |
| JP | 03-011081 A | 1/1991 |
| JP | 03-091578 A | 4/1991 |
| JP | 03-205476 A | 9/1991 |
| JP | 05-098252 A | 4/1993 |
| JP | 05-163324 A | 6/1993 |
| JP | 06-256758 A | 9/1994 |
| JP | 07-062337 A | 3/1995 |
| JP | 08-176139 A | 7/1996 |
| WO | WO 97/05213 | 2/1997 |
| WO | WO 00/05325 | 2/2000 |
| WO | WO 00/21968 | 4/2000 |
| WO | WO 01/70719 A2 | 9/2001 |
| WO | WO 2004/041961 A1 | 5/2004 |

OTHER PUBLICATIONS

Fink, J.K., Polyurethanes, Reactive Polymers Fundamentals and Applications A Concise Guide to Industrial Polymers, William Andrew Publishing, 2005, pp. 69-70.*
Reactive Polymers Fundamentals and Applications, A Concise Guide to Industrial Polymers by Johannes Karl Fink, 2005, Chapter 2, "Urethanes", pp. 69-138.

* cited by examiner

*Primary Examiner*—Timothy J Kugel
(74) *Attorney, Agent, or Firm*—Frank P. Mallak; Linda Pingitore; Deborah M. Altman

(57) ABSTRACT

Various non-limiting embodiments disclosed herein related to photochromic materials comprising the reaction product of (a) at least one ring-opening cyclic monomer, and (b) a photochromic initiator. Other non-limiting embodiments related to photochromic materials represented by:

$$PC-[S']_n$$

wherein S' comprises the at least one ring-opened cyclic monomer as set forth herein. Other non-limiting embodiments related to photochromic compositions, optical elements, and methods of inhibiting migration of a photochromic material in a polymeric material using the photochromic materials disclosed herein. Methods of making such photochromic materials, compositions, and optical elements are also disclosed.

21 Claims, 6 Drawing Sheets

PHOTOCHROMIC MATERIALS DERIVED FROM RING-OPENING MONOMERS AND PHOTOCHROMIC INITIATORS

BACKGROUND

Various non-limiting embodiments disclosed herein generally relate to materials having at least one flexible segment bonded thereto, and more particular relate to photochromic materials comprising at least one ring-opened cyclic monomer bonded thereto. Other non-limiting embodiments relate to photochromic compositions and optical elements, such as but not limited to ophthalmic lenses, that include the disclosed photochromic materials.

Photochromic materials can be incorporated into polymeric materials to impart desired optical properties to the polymeric material. For example, photochromic materials have been successfully incorporated into polymeric materials that are used to form ophthalmic lenses, as well as polymeric coatings applied thereto. Typically, the polymeric materials into which the photochromic materials are incorporated are relatively soft, and thus, susceptible to mechanical damage, such as scuffing and scratching. Since it is generally undesirable for certain articles of manufacture, such as ophthalmic lenses, to be susceptible to such damage, often one or more "hard coatings" are applied to the surfaces of the articles to enhance, among other things, their abrasion-resistance. For example, hard coatings are routinely applied to the surfaces of ophthalmic lenses formed from "soft" polymeric materials to enhance their abrasion-resistance.

However, it has been observed that, under certain conditions, photochromic materials have a tendency to migrate from the soft polymeric material into which they are incorporated into such other hard coatings. Since the photochromic performance of a photochromic material (i.e., the coloration (or activation) and fade rates of the photochromic material) is influenced by the local environment surrounding the photochromic material, migration can deteriorate photochromic performance. Generally speaking, for an organic photochromic material, the time required for coloration or fading to occur tends to increase with the hardness of the local environment surrounding the photochromic material. Thus, when a photochromic material migrates from a relatively soft or flexible environment to a relatively hard or rigid environment, the photochromic performance of the material can deteriorate. Consequently, migration can result in a decrease of the utility of a photochromic material, as well as that of a coating or an article into which it is incorporated.

One method of reducing the migration of a photochromic material in a polymeric material is to bond the photochromic material to the polymeric material. For example, photochromic materials having relative short, organic chain segments that can be polymerized into a polymeric material have been disclosed. Such photochromic materials have a reduced tendency to migrate in the polymeric material due to the physical constraints afforded by bonding of the photochromic material to the polymeric material. However, bonding the photochromic material to the polymeric material using such short, organic chain segments can have the effect of slowing the coloration and fade rates of the photochromic material as compared to a similar photochromic material that is not bonded to the polymeric material. Additionally, for some photochromic materials, it is preferred to place the short, organic chain segments at locations that are distant from the "active" portion of the photochromic material, i.e., that portion of the photochromic material that undergoes reversible transformation from one state to another on exposure to actinic radiation. That is, for some photochromic materials, if the chain segments are placed too close to the active portion of the photochromic material, the ability of the photochromic material to transform can be impeded. Consequently, the photochromic performance of the material can be diminished.

Other methods of modifying the fade rates of photochromic materials have focused on creating a relatively "soft" environment around the photochromic material, such that the photochromic performance of the material is relatively unaffected by the hardness of the polymeric material into which it is incorporated, rather than reducing migration. For example, photochromic materials that are adducts of a photochromic moiety and at least one pendant oligomeric group have been disclosed. However, because such photochromic materials are not generally bonded to the polymeric materials into which they are incorporated, phase separation may occur if the photochromic materials are not compatible with the polymeric material. That is, the photochromic materials may separate from the polymeric material, which can result in undesirable properties, such as haze and blooming, which can limit the utility of the materials in many applications wherein the transparency is important.

Accordingly, it would be advantageous to develop photochromic materials having both a reduced tendency to migrate and favorable coloration and/or fade rates that can be incorporated into a variety of polymeric materials.

BRIEF SUMMARY OF THE DISCLOSURE

Various non-limiting embodiments disclosed herein relate to photochromic materials. For example, one non-limiting embodiment provides a photochromic material comprising a reaction product of (a) at least one ring-opening cyclic monomer chosen from a cyclic ester and a cyclic carbonate, and (b) a photochromic initiator.

Another non-limiting embodiment provides a photochromic material represented by:

wherein (a) PC is a photochromic group; (b) n is an integer chosen from 1 to 8; and (c) each S' is independently chosen for each occurrence from a group represented by:

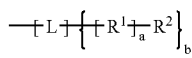

wherein (1) L is a linking group independently chosen for each occurrence from —O—, —N—, and —S—, or L comprises a linear or branched organic bridging group comprising at least one linking group that is independently chosen for each occurrence from —O—, —N—, and —S—; (2) 'a' is an integer that is independently chosen for each occurrence from 1 to 500; (3) $R^1$ is a independently chosen for each occurrence from a ring-opened cyclic ester monomer and a ring-opened cyclic carbonate monomer; (4) $R^2$ is independently chosen for each occurrence from hydrogen and an organic material comprising the residue of at least one reactive group; and (5) b is a integer that is independently chosen for each occurrence from 1 to 20.

Another non-limiting embodiment provides a photochromic material represented by:

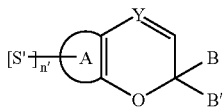

wherein (a) Y is chosen from C and N; (b) A is chosen from naphtho, benzo, phenanthro, fluorantheno, antheno, quinolino, thieno, furo, indolo, indolino, indeno, benzofuro, benzothieno, thiopheno, indenonaphtho, heterocyclic-fused naphtho, and heterocyclic-fused benzo; (c) n' is an integer chosen from 0 to 8, provided that if n' is 0 at least one of B and B' comprises the group S'; (d) S' is represented by:

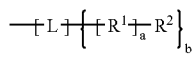

wherein (1) L is a linking group independently chosen for each occurrence from —O—, —N—, and —S—, or L comprises a linear or branched organic bridging group comprising at least one linking group that is independently chosen for each occurrence from —O—, —N—, and —S—; (2) 'a' is an integer that is independently chosen for each occurrence from 1 to 500; (3) $R^1$ is independently chosen for each occurrence from a ring-opened cyclic ester monomer and a ring-opened cyclic carbonate monomer; (4) $R^2$ is independently chosen for each occurrence from hydrogen and an organic material comprising the residue of at least one reactive group, wherein the residue of the at least one reactive group is chosen from an acrylate, an alkyl, an alkyl phosphonate, an alkyldialkoxysilyl, an alkyloxydialkylsilyl, an allyl carbonate, an amide, an amine, an anhydride, an aryl, an aziridine, a carboxylic acid, a chloroformate, a cycloaliphatic epoxide, an isocyanate, an isothiocyanate, an epoxide, an ester, a halogen, a hydroxyl group, a methacrylate, a propenyl ether, a residue of a ring-opening cyclic monomer, a trialkoxysilyl, a thiirane, a thiol, a vinyl carbonate, a vinyl ether, a vinylbenzyl ether, and combinations thereof; (5) b is a integer that is independently chosen for each occurrence from 1 to 20; and (e) B and B' are independently chosen from: (1) the group S'; (2) mono-$R^{17}$-substituted phenyl wherein $R^{17}$ is represented by one of: -G[$(OC_2H_4)_q(OC_3H_6)_r(OC_4H_8)_s$]J and —[$(OC_2H_4)_q(OC_3H_6)_r(OC_4H_8)_s$]J, wherein -G is chosen from —C(O)— and —CH$_2$—, J is chosen from C1-C12 alkoxy and a polymerizable group; q, r, and s are each a number between 0 and 50, and the sum of q, r, and s is between 2 and 50; (3) an unsubstituted, mono-, di-, or tri-substituted aryl group; (4) 9-julolidinyl, an unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, each of the aryl and heteroaromatic substituents in (3) and (4) are independently chosen from: (i) hydroxy; (ii) the group —C(O)$R^{18}$, wherein $R^{18}$ is chosen from —O$R^{19}$, —N($R^{21}$, piperidino and morpholino, wherein $R^{19}$ is chosen from allyl, C1-C6 alkyl, phenyl, mono(C1-C6)alkyl substituted phenyl, mono(C1-C6) alkoxy substituted phenyl, phenyl(C1-C3)alkyl, mono(C1-C6)alkyl substituted phenyl(C1-C3)alkyl, mono(C1-C6) alkoxy substituted phenyl(C1-C3)alkyl, C1-C6 alkoxy(C2-C4)alkyl and C1-C6 haloalkyl; $R^{20}$ and $R^{21}$ are each chosen from C1-C6 alkyl, C5-C7 cycloalkyl, phenyl, mono-substituted phenyl and di-substituted phenyl, the phenyl substituents being chosen from C1-C6 alkyl and C1-C6 alkoxy, and said halo substituent being chosen from chloro and fluoro; (iii) aryl, mono(C1-C12)alkoxyaryl, di(C1-C12)alkoxyaryl, mono(C1-C12)alkylaryl, di(C1-C12)alkylaryl, haloaryl, C3-C7 cycloalkylaryl, C3-C7 cycloalkyl, C3-C7 cycloalkyloxy, C3-C7 cycloalkyloxy(C1-C12)alkyl, C3-C7 cycloalkyloxy(C1-C12)alkoxy, aryl(C1-C12)alkyl, aryl(C1-C12) alkoxy, aryloxy, aryloxy(C1-C12)alkyl, aryloxy(C1-C12) alkoxy, mono- or di(C1-C12)alkylaryl(C1-C12)alkyl, mono- or di-(C1-C12)alkoxyaryl(C1-C12)alkyl, mono- or di-(C1-C12)alkylaryl(C1-C12)alkoxy, mono- or di-(C1-C12)alkoxyaryl(C1-C12)alkoxy, amino, mono(C1-C12)alkylamino, di(C1-C12)alkylamino, diarylamino, piperazino, N-(C1-C12)alkylpiperazino, N-arylpiperazino, aziridino, indolino, piperidino, morpholino, thiomorpholino, tetrahydroquinolino, tetrahydroisoquinolino, pyrrolidyl, C1-C12 alkyl, C1-C12 haloalkyl, C1-C12 alkoxy, mono(C1-C12) alkoxy(C1-C12)alkyl, acryloxy, methacryloxy, and halogen; (5) an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, each of said substituents being independently chosen from C1-C12 alkyl, C1-C12 alkoxy, phenyl, and halogen; (6) a monosubstituted phenyl, said phenyl having a substituent located at the para position, wherein the substituent is chosen from —(CH$_2$)$_t$— and —O—(CH$_2$)$_t$—, wherein t is an integer chosen from 1, 2, 3, 4, 5 and 6, the substituent being connected to an aryl group on another photochromic material; (7) a group represented by one of:

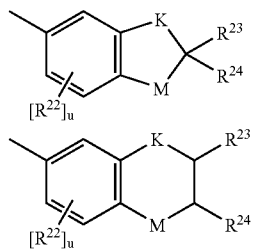

wherein K is independently chosen in each formula from methylene and oxygen, and M is independently chosen in each formula from oxygen and substituted nitrogen, provided that when M is substituted nitrogen, K is methylene; the substituted nitrogen substituents being chosen from hydrogen, C1-C12 alkyl, and C1-C12 acyl; each $R^{22}$ being independently chosen for each occurrence in each formula from C1-C12 alkyl, C1-C12 alkoxy, hydroxy, and halogen; $R^{23}$ and $R^{24}$ each being independently chosen in each formula from hydrogen and C1-C12 alkyl; and u is an integer chosen from 0, 1 and 2; (8) C1-C12 alkyl, C1-C12 haloalkyl, C1-C12 alkoxy(C1-C12)alkyl, C3-C7 cycloalkyl, mono(C1-C12) alkoxy (C3-C7)cycloalkyl, mono(C1-C12)alkyl(C3-C7)-cycloalkyl, halo(C3-C7)cycloalkyl, and C4-C12 bicycloalkyl, provided that both B and B' are not chosen from (8); and (9) a group represented by:

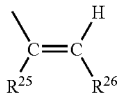

wherein $R^{25}$ is chosen from hydrogen and C1-C12 alkyl, and $R^{26}$ is chosen from an unsubstituted, mono-, or di-substituted group chosen from naphthyl, phenyl, furanyl, and thienyl, wherein the substituents are independently chosen from C1-C12 alkyl, C1-C12 alkoxy, and halogen; or (10) B and B' taken together form a fluoren-9-ylidene, mono-, or di-substituted fluoren-9-ylidene or a spirocyclic group chosen from saturated C3-C12 spiro-monocyclic hydrocarbon rings, saturated C7-C12 spiro-bicyclic hydrocarbon rings, or saturated C7-C12 spiro-tricyclic hydrocarbon rings, provided that said spirocyclic group is not norbornylidene or bicyclo[3.3.1]9-nonylidene, each of said fluoren-9-ylidene substituents being independently chosen from C1-C12 alkyl, C1-C12 alkoxy, halogen, or the group S'.

Another non-limiting embodiment provides a photochromic material represented by:

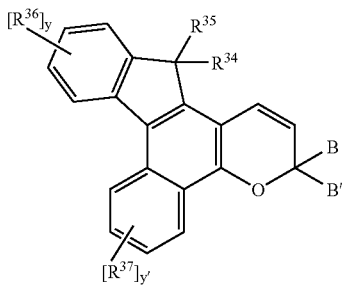

wherein (a) $R^{34}$ and $R^{35}$ are independently chosen from (1) a group S', wherein S' is represented by

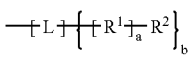

wherein (A) L comprises at least one group chosen from C1-C10 alkyloxy, C1-C10-alkylamino, C1-C10 alkylthio, C2-C20 beta-oxypoly(ethoxy), C3-C30 beta-oxypoly(propoxy), C4-C40 beta-oxypoly(butoxy), C2-C20 beta-aminopoly(ethoxy), C3-C30 beta-aminopoly(propoxy), C4-C40 beta-aminopoly(butoxy), C2-C20 beta-thiopoly(ethoxy), C3-C30 beta-thiopoly(propoxy), C4-C40 beta-thiopoly(butoxy), aryl C1-C10 alkyloxy, aryl C1-C10 alkylamino, aryl C1-C10 alkylthio, aryl C2-C20 beta-oxypoly(ethoxy), aryl C3-C30 beta-oxypoly(propoxy), aryl C4-C40 beta-oxypoly(butoxy), aryl C2-C20 beta-aminopoly(ethoxy), aryl C3-C30 beta-aminopoly(propoxy), aryl C4-C40 beta-aminopoly(butoxy), aryl C2-C20 beta-thiopoly(ethoxy), aryl C3-C30 beta-thiopoly(propoxy), aryl C4-C40 beta-thiopoly(butoxy), heterocyclic C1-C10 alkyloxy, heterocyclic C1-C10 alkylamino, heterocyclic C1-C10 alkylthio, heterocyclic C2-C20 beta-oxypoly(ethoxy), heterocyclic C3-C30 beta-oxypoly(propoxy), heterocyclic C4-C40 beta-oxypoly(butoxy), heterocyclic C2-C20 beta-aminopoly(ethoxy), heterocyclic C3-C30 beta-aminopoly(propoxy), heterocyclic C4-C40 beta-aminopoly(butoxy), heterocyclic C2-C20 beta-thiopoly(ethoxy), heterocyclic C3-C30 beta-thiopoly(propoxy), and heterocyclic C4-C40 beta-thiopoly(butoxy); (B) 'a' is an integer that is independently chosen for each occurrence from 1 to 500; (C)$R^1$ is independently chosen for each occurrence from a ring-opened cyclic ester monomer and a ring-opened cyclic carbonate monomer; (D) $R^2$ is independently chosen for each occurrence from hydrogen and an organic material comprising the residue of at least one reactive group, wherein the residue of the at least one reactive group is chosen from an acrylate, an alkyl, an alkyl phosphonate, an alkyldialkoxysilyl, an alkyloxydialkylsilyl, an allyl carbonate, an amide, an amine, an anhydride, an aryl, an aziridine, a carboxylic acid, a chloroformate, a cycloaliphatic epoxide, an isocyanate, an isothiocyanate, an epoxide, an ester, a halogen, a hydroxyl group, a methacrylate, a propenyl ether, a residue of a ring-opening cyclic monomer, a trialkoxysilyl, a thiirane, a thiol, a vinyl carbonate, a vinyl ether, a vinylbenzyl ether, and combinations thereof; and (E) b is a integer that is independently chosen for each occurrence from 1 to 20; and (2) hydrogen, hydroxy, C1-C6 alkyl, C3-C7 cycloalkyl, allyl, phenyl, mono-substituted phenyl, benzyl, mono-substituted benzyl, chloro, fluoro, the group —C(O)$R^{40}$, wherein $R^{40}$ is hydroxy, C1-C6 alkyl, C1-C6 alkoxy, phenyl, mono-substituted phenyl, amino, mono(C1-C6)alkylamino, or di(C1-C6)alkylamino; or (3) $R^{34}$ and $R^{35}$ are each the group —O$R^{41}$, wherein $R^{41}$ is C1-C6 alkyl, phenyl(C1-C3)alkyl, mono(C1-C6)alkyl substituted phenyl(C1-C3)alkyl, mono(C1-C6)alkoxy substituted phenyl(C1-C3)alkyl, C1-C6 alkoxy(C2-C4)alkyl, C3-C7 cycloalkyl, mono(C1-C4)alkyl substituted C3-C7 cycloalkyl, C1-C6 chloroalkyl, C1-C6 fluoroalkyl, allyl, the group —CH($R^{42}$)$R^{43}$, wherein $R^{42}$ is hydrogen or C1-C3 alkyl and $R^{43}$ is CN, CF$_3$, or COOR$^{44}$ and $R^{44}$ is hydrogen or C1-C3 alkyl; or $R^{41}$ is the group —C(O)$R^{45}$, wherein $R^{45}$ is hydrogen, C1-C6 alkyl, C1-C6 alkoxy, the unsubstituted, mono- or di-substituted aryl groups phenyl or naphthyl, phenoxy, mono- or di-(C1-C6)alkyl substituted phenoxy, mono- or di-(C1-C6)alkoxy substituted phenoxy, amino, mono(C1-C6)alkylamino, di(C1-C6)alkylamino, phenylamino, mono- or di-(C1-C6)alkyl substituted phenylamino, or mono- or di-(C1-C6)alkoxy substituted phenylamino, each of said phenyl, benzyl and aryl group substituents being C1-C6 alkyl or C1-C6 alkoxy; or (4) $R^{34}$ and $R^{35}$ together form an oxo group, a spiro-carbocyclic ring containing 3 to 6 carbon atoms or a spiro-heterocyclic group containing 1 or 2 oxygen atoms and 3 to 6 carbon atoms including the spirocarbon atom, said spiro-carbocyclic and spiro-heterocyclic groups being annellated with 0, 1 or 2 benzene rings; (b) y and y' are integers that are independently chosen from 0 to the total number of available positions; (c) each $R^{36}$ and $R^{37}$ is independently chosen from the group S', hydrogen, C1-C6 alkyl, C3-C7 cycloalkyl, phenyl, mono-substituted phenyl, di-substituted phenyl and the groups —O$R^{50}$ and —OC(O)$R^{50}$, wherein $R^{50}$ is C1-C6 alkyl, phenyl (C1-C3)-alkyl, mono(C1-C6)alkyl substituted phenyl(C1-C3)alkyl, mono(C1-C6)alkoxy substituted phenyl(C1-C3)alkyl, C1-C6 alkoxy(C2-C4)alkyl, C3-C7 cycloalkyl or mono (C1-C4)alkyl substituted C3-C7 cycloalkyl, and said phenyl substituent being C1-C6 alkyl or C1-C6 alkoxy; (e) B and B' are as set forth above; provided that the photochromic material comprises at least one group S'.

Other non-limiting embodiments relate to photochromic composition and optical elements comprising the aforementioned photochromic materials and methods of making the same. One specific non-limiting embodiment provides a photochromic composition comprising (a) a polymeric material; and (b) at least one photochromic material bonded to at least a portion of the polymeric material, the at least one photochromic material comprising (1) a photochromic group, and (2) at least one segment comprising the residue of a plurality of ring-opening cyclic monomers bonded to the photochromic group, the ring-opening cyclic monomers being chosen from cyclic esters, cyclic carbonates, cyclic ethers, cyclic siloxanes, and combinations thereof, wherein the at least one segment has a number average molecular weight of at least 1000 g/mol.; and wherein the photochromic material when bonded to the polymeric material has a T½ value that is no greater than a T½ value of a corresponding photochromic material that lacks a segment comprising the residue of a plurality of ring-opening cyclic monomers.

Still another non-limiting embodiment provides a method of inhibiting migration of a photochromic material in a polymeric material, the method comprising bonding the photochromic material to at least a portion of the polymeric material, wherein the photochromic material comprises (1) a photochromic group, and (2) at least one segment comprising the residue a plurality of ring-opening cyclic monomers bonded to the photochromic group, the ring-opening cyclic monomers being chosen from cyclic esters, cyclic carbonates, cyclic ethers, cyclic siloxanes, and combinations thereof, wherein the at least one segment has a number average molecular weight of at least 1000 g/mol.

Another non-limiting embodiment provides a method of making a photochromic material comprising: initiating ring-opening of at least one ring-opening one cyclic monomer chosen from a cyclic ester, a cyclic carbonate, a cyclic ether, and a cyclic siloxane, with a photochromic initiator comprising at least one functional group adapted to initiate ring-opening of at least one ring-opening cyclic monomer, the at least one functional group being chosen from an alcohol, an amine, a carboxylic acid, a silanol, a thiol, and combinations, salts and complexes thereof.

BRIEF DESCRIPTION OF THE SEVERAL VIEWS OF THE DRAWING(S)

Various non-limiting embodiments disclosed herein will be better understood when read in conjunction with the drawings, in which.

Figure 1:
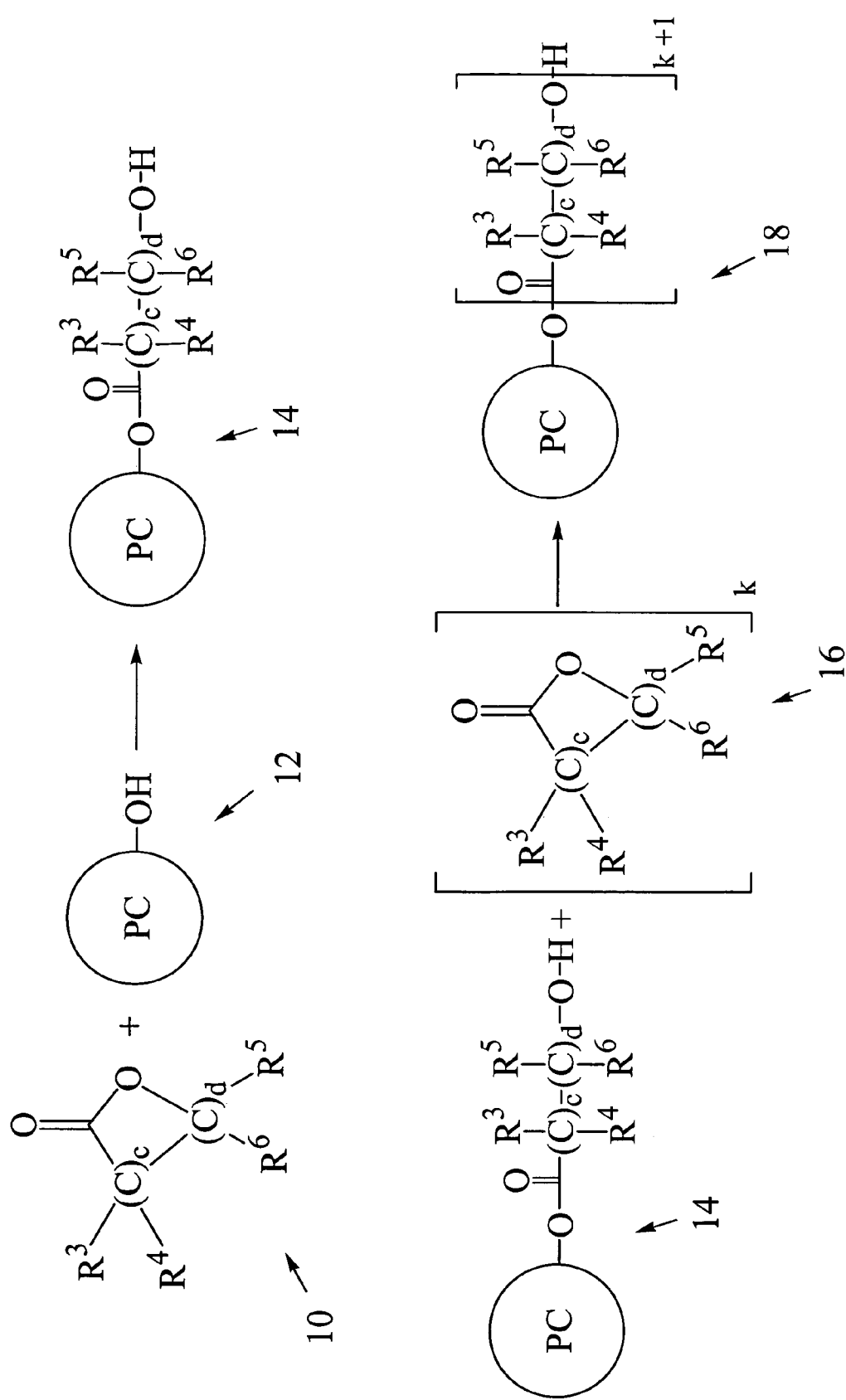
FIGS. 1 and 4-6 are schematic depictions of various routes for preparing photochromic materials according to various non-limiting embodiments disclosed herein.

FIGS. 7(*a*)-7(*c*) depict photochromic materials according to various non-limiting embodiments disclosed herein.

DETAILED DESCRIPTION

As used in this specification and the appended claims, the articles "a," "an," and "the" include plural referents unless expressly and unequivocally limited to one referent.

Additionally, for the purposes of this specification, unless otherwise indicated, all numbers expressing quantities of ingredients, reaction conditions, and other properties or parameters used in the specification are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

Further, while the numerical ranges and parameters setting forth the broad scope of the invention are approximations as discussed above, the numerical values set forth in the Examples section are reported as precisely as possible. It should be understood, however, that such numerical values inherently contain certain errors resulting from the measurement equipment and/or measurement technique.

As previously discussed, photochromic materials are often incorporated into polymeric materials to impart desired optical properties to the polymeric material or an article of manufacture made therefrom. Further, as discussed above, the photochromic performance (i.e., the coloration and fade rates of the photochromic material) can be influenced by the environment surrounding the photochromic material. Thus, when an organic photochromic material migrates from a relatively "soft" or "flexible" environment to a relatively "hard" or "rigid" environment, the photochromic performance of the material can be compromised. While, bonding the photochromic material to the polymer material can help to reduce migration, previous attempts to do so have generally resulted in decreased photochromic performance of the photochromic material as compared to that of the un-migrated, un-bonded photochromic material.

Although not limiting herein, rigid or hard polymers tend to have glass transition temperatures higher than room temperature, e.g. 23° C.; whereas polymers having glass transition temperatures less than room temperature tend to be soft and flexible. Those skilled in the art will appreciate that the by selecting appropriate rigid and/or flexible polymer segments, polymers having a desired the hardness or softness can be prepared. Rigid polymer segments are segments that tend to form polymeric materials that are stiff and undergo little plastic deformation before breaking. Flexible polymer segments are segments that tend to form polymeric materials that are pliable and capable of being plastically deformed without breaking. For example, methods of preparing urethane materials by choosing the components, e.g., isocyanates and polyols, to form the appropriate segment types are known to those skilled in the art. See for example the discussion of hard and soft segments in U.S. Pat. No. 6,187,444 at col. 3, line 49 to col. 4, line 46, which disclosure is hereby specifically incorporated by reference herein.

As discussed herein below, it has been observed by the inventors that when the photochromic materials according to various non-limiting embodiments disclosed herein are bonded to polymeric materials, the tendency of the photochromic materials to migrate can be reduced as compared to similar conventional photochromic materials that are not bonded to the polymeric material. Further, it has been observed that, even when bonded to the polymeric material, the photochromic performance of the photochromic materials according to various non-limiting embodiments disclosed herein can be equivalent to or better than that of similar conventional photochromic materials that are not bonded to the polymeric material.

Photochromic materials according to various non-limiting embodiments of the invention will now be discussed. As used herein, the term "photochromic" means having an absorption spectrum for at least visible radiation that varies in response to at least actinic radiation. Further, as used herein the term "photochromic material" means any substance that is adapted to display photochromic properties, i.e. adapted to have an absorption spectrum for at least visible radiation that varies in response to at least actinic radiation. Thus, as used herein the term "photochromic materials" includes organic photochromic materials, inorganic photochromic materials, and combinations thereof. As used herein the term "organic photochromic material" means organic materials, such as but not limited to photochromic groups, as well as polymers, prepolymers, monomers, and other compounds that comprise at least one photochromic group. As used herein the term "photochromic group" refers to an organic photochromic entity comprising at least one photochromic moiety, and which may contain other organic groups or compounds (e.g., functional groups, and/or aliphatic, alicyclic, aromatic, and heterocyclic groups and compounds, etc.) that are linked or fused thereto. As used herein the term "photochromic moiety" refers the portion of a photochromic group that can undergo reversible transformation from one state to another on exposure to actinic radiation (i.e., the "active portion" of the photochromic material as previously discussed). As used herein the term "linked" means covalently bonded. Further, as used herein the term "fused" means covalently bonded at least two positions.

Further, as used herein, the term "pre-polymers" or "pre-polymeric materials" refers to partially polymerized materials, including without limitation oligomeric and partially polymerized materials. As used herein, the terms "polymers" and "polymeric materials" refer to homopolymers and copolymers (e.g. block copolymers, random copolymers, and alternating copolymers), as well as blends and other combinations thereof.

Non-limiting examples of photochromic groups that can be used in conjunction with various non-limiting embodiments disclosed herein include photochromic pyrans, photochromic oxazines, and photochromic fulgides. Non-limiting examples of photochromic pyrans that can be used herein include benzopyrans; naphthopyrans, e.g., naphtho[1,2-b]pyrans, naphtho[2,1-b]pyrans; indenonaphthopyrans, such as those disclosed in U.S. Pat. No. 5,645,767 at col. 2, line 16 to col. 12, line 57; heterocyclic-fused naphthopyrans, such as those disclosed in U.S. Pat. No. 5,723,072 at col. 2, line 27 to col. 15, line 55; U.S. Pat. No. 5,698,141 at col. 2, line 11 to col. 19, line 45, U.S. Pat. No. 6,153,126 at col. 2, line 26 to col. 8, line 60, and U.S. Pat. No. 6,022,497 at col. 2, line 21 to col. 11, line 46, which disclosures are hereby specifically incorporated by reference herein; spiro-9-fluoreno[1,2-b]pyrans; phenanthropyrans; quinolinopyrans; fluoroanthenopyrans; and spiropyrans, e.g., spiro(benzindoline)naphthopyrans, spiro(indoline) benzopyrans, spiro(indoline)naphthopyrans, and spiro (indoline)pyrans. More specific non-limiting examples of naphthopyrans are described in U.S. Pat. No. 5,658,501 at col. 1, line 64 to col. 13, line 17, which disclosure is hereby specifically incorporated by reference herein. Spiro(indoline) pyrans are also described in the text, *Techniques in Chemistry*, Volume III, "Photochromism", Chapter 3, Glenn H. Brown, Editor, John Wiley and Sons, Inc., New York, 1971, which disclosure is also specifically incorporated by reference herein.

Non-limiting examples of photochromic oxazines that can be used in conjunction with various non-limiting embodiments disclosed herein include benzoxazines; naphthoxazines; and spiro-oxazines, e.g., spiro(indoline)naphthoxazines, spiro(indoline)pyridobenzoxazines, spiro (benzindoline)pyridobenzoxazines, spiro(benzindoline) naphthoxazines, spiro(indoline)benzoxazines, spiro (indoline)fluoranthenoxazine, and spiro(indoline) quinoxazine.

Non-limiting examples of thermally reversible photochromic fulgides or fulgimides that can be used in conjunction with various non-limiting embodiments disclosed herein include those fulgides and fulgimides that are disclosed in U.S. Pat. No. 4,685,783 at col. 1, line 57 to col. 5, line 27, the disclosure of which is hereby specifically incorporated by reference herein, and mixtures of any of the aforementioned photochromic materials.

Various non-limiting embodiments provided herein relate to a photochromic material comprising a reaction product of: (a) at least one ring-opening cyclic monomer, and (b) a photochromic initiator. As used herein, the term "photochromic initiator(s)" refers to photochromic material(s) comprising at least one functional group that is adapted to initiate ring-opening of at least one cyclic monomer. As previously discussed, as used herein, the term "photochromic material" means any substance that is adapted to display photochromic properties. Accordingly, the photochromic initiators according to various non-limiting embodiments disclosed herein can be organic photochromic materials, inorganic photochromic materials, or combinations thereof that comprise at least one functional group that is adapted to initiate a ring-opening reaction. Suitable non-limiting organic photochromic materials include photochromic groups, as well as polymers, prepolymers, monomers, and other compounds that comprise at least one photochromic group. Non-limiting examples of photochromic groups that can be used in conjunction with these and other non-limiting embodiments disclosed herein are set forth above in detail.

As used herein, the term "ring-opening cyclic monomer" refers to a monomer having a ring structure that is capable of undergoing a ring-opening reaction or ring-opening polymerization. As used herein the terms "ring-opening" and "ring-opening reaction" refer to the conversion of a cyclic monomer into its acyclic form, typically on reaction with an initiator. Further, as used herein, the term "ring-opening polymerization" refers to formation of a chain of a plurality of ring-opened cyclic monomers. As used herein the term "ring-opened cyclic monomer" means the acyclic form of a ring-opening cyclic monomer. As used herein the term "residue of a ring-opening cyclic monomer" means that which remains after a ring-opening cyclic monomer undergoes a ring-opening reaction. As used herein, the term "plurality" means at least two.

Examples of ring-opening cyclic monomers that can be used in conjunction with various non-limiting embodiments disclosed herein include, without limitation, cyclic esters, cyclic carbonates, cyclic ethers, and cyclic siloxanes.

Non-limiting examples of suitable cyclic esters include those represented by:

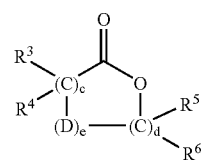

wherein c and d are integers ranging from 1 to 8; and $R^3$, $R^4$, $R^5$, and $R^6$ are independently chosen for each carbon unit (i.e., for each $(C)_c$ and $(C)_d$ unit) from —H, —CH$_3$, C2-C$_{1-6}$ alkyl, C(CH$_3$)$_2$, and HO—CH$_2$—; e is 0 or 1; and D is chosen from —O— or —O—C(O)—. Alternatively, c can be 1, D can be —C(R$^{3'}$)(R$^{4'}$)—, and R$^{3'}$ and R$^{4'}$ can come together with R$^3$ and R$^4$ to form a fused-aryl, fused-heterocyclic aryl, or fused-cycloaliphatic group, for example as shown below.

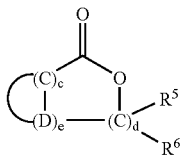

Specific non-limiting examples of suitable cyclic esters include ε(epsilon)-caprolactone; t-butyl caprolactone; ζ(zeta)-enantholactone; δ(delta)-valerolactone; a monoalkyl δ-valerolactone, such as but not limited to monomethyl-, monoethyl-, and monohexyl-δ-valerolactone; the nonalkyl, dialkyl, and trialkyl-ε-caprolactones, such as but not limited to the monomethyl-, monoethyl-, monohexyl-, dimethyl-, di-n-propyl-, di-n-hexyl-, trimethyl-, triethyl-, and tri-n-ε-caprolactones, 5-nonyl-oxepan-2-one, 4,4,6- or 4,6,6-trimethyl-oxepan-2-one, 5-hydroxymethyl-oxepan-2-one; β(beta)-lactones, such as but not limited to β-propiolactone, β-butyrolactone; γ(gamma)-lactones, such as but not limited to γ-butyrolactone and pivalolactone; dilactones, such as but not limited to lactides, dilactides, glycolides (e.g., tetramethyl glycolides); and ketodioxanones, such as but not limited to 1,4-dioxan-2-one and 1,5-dioxepane-2-one.

Non-limiting examples of suitable cyclic carbonates include those represented by:

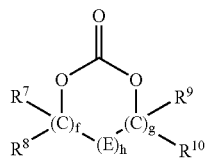

wherein f and g are integers ranging from 1 to 3; $R^7$, $R^8$, $R^9$, and $R^{10}$ are independently chosen for each carbon unit (i.e., for each $(C)_f$ and $(C)_g$ unit) from —H, —CH$_3$, C2-C16 alkyl, C(CH$_3$)$_2$, HO—CH$_2$—, or —OC$_6$H$_5$; h is 0 or 1; and E is —O—. Specific examples of suitable cyclic carbonates include, without limitation, ethylene carbonate, 3-ethyl-3-hydroxylmethyl trimethylene carbonate, propylene caronate, trimethylene carbonate, trimethylolpropane monocarbonate, 4,6-dimethyl-1,3-propylene carbonate, 2,2-dimethyl trimethylene carbonate, and 1,2-dioxepan-2-one.

Non-limiting examples of suitable cyclic ethers include those represented by:

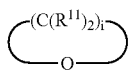

wherein 'i' is an integer ranging from 2 to 5, and each $R^{11}$ may be the same or different and may be chosen from hydrogen; a halogen, such as but not limited to fluorine, chlorine, bromine, and iodine; C1-C10 alkyl, such as but not limited to linear or branched methyl, ethyl, n-propyl, isopropyl, n-butyl, sec-butyl, pentyl, hexyl, heptyl, octyl, nonyl, and decyl; phenyl, which may be substituted or unsubstituted; halogenated C1-C10 alkyl, such as but not limited to chloromethyl, bromomethyl, iodomethyl, dichloromethyl, 2-chloromethyl, and 3-chloromethyl; and C1-C6 alkylols, such as methylol (e.g., —CH$_2$OH). Specific non-limiting examples of cyclic ethers include, for example, ethylene oxide, 1,2-propylene oxide, epichlorohydrin, epibromohydrin, 1,2-butylene oxide, 2,3-butylene oxide, isobutylene oxide, oxetane, 3-methyloxetane, 3,3-dimethyloxetane, tetrahydrofuran, 2-methyltetrahydrofuran, 3-methyltetrahydrofuran, and tetrahydrofuran.

Non-limiting examples of suitable cyclic siloxanes include those represented by:

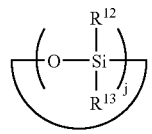

wherein $R^{12}$ and $R^{13}$ are the same or different and each is independently chosen for each siloxane unit from C1-C8 linear or branched alkyl, aryl, aryl(C1-C6)alkyl, or (C1-C6) alkylaryl, and j is the number of siloxane units and is chosen from 3 to 6. For example, although not limiting herein, according to one non-limiting embodiment $R^{12}$ and $R^{13}$ can each be methyl and j can be 3 or 4. Non-limiting examples of such cyclic siloxanes include, without limitation, hexamethylcyclotrisiloxane (i.e., j=3) and octamethylcyclotetrasiloxane (i.e., j=4).

Although not limiting herein, according to one non-limiting embodiment disclosed herein the photochromic material comprises a reaction product of: (a) at least one ring-opening cyclic monomer chosen from a cyclic ester and a cyclic carbonate, and (b) a photochromic initiator. For example, although not limiting herein, according to this non-limiting embodiment the at least one cyclic monomer can be chosen from ε-caprolactone and δ-valerolactone.

As mentioned above, the ring-opening of a ring-opening cyclic monomer typically involves an initiator. It will be appreciated by those skilled in the art that the choice of initiator will depend, in part, upon the cyclic monomer involved. For example, suitable initiators for use with ring-opening cyclic esters can be chosen from, without limitation, alcohols, amines, carboxylic acids, thiols, as well as combinations, salts and complexes thereof. Further, once the ring-opening cyclic monomer has undergone a ring-opening reaction with an appropriate initiator, the ring-opened monomer itself can serve to initiate the ring-opening of another ring-opening cyclic monomer, which in turn can serve to initiate ring-opening of yet another ring-opening cyclic monomer, etc., thereby forming a chain of two (or more) ring-opened monomers. In other words, ring-opening polymerization of a plurality of ring-opening cyclic monomers can occur. Depending upon the ring-opening cyclic monomers employed, ring-opening polymerization can result in the formation of a homopolymer or a copolymer. For example, a homopolymer can be formed by ring-opening polymerization of a plurality of ring-opening cyclic monomers of the same kind. Alternatively, a copolymer can be formed by ring-opening polymerization of a plurality of ring-opening cyclic monomers, at least one of which is different from the remainder.

For example, although not limiting herein, as schematically depicted in FIG. 1, a ring-opening cyclic monomer (generally indicated as 10 in FIG. 1) can be ring-opened by reaction of the ring-opening cyclic monomer with a photochromic initiator (generally indicated as 12), thereby forming a photochromic material (generally indicated as 14) according to various non-limiting embodiments disclosed herein. As shown in FIG. 1, the ring-opening cyclic monomer is a cyclic ester as set forth above wherein e is 0. Further, as depicted in FIG. 1, photochromic initiator 12 comprises at least one functional group (i.e., a hydroxyl (—OH) group as shown in FIG. 1) that is adapted to initiate the ring-opening reaction. Although not required, as further depicted in FIG. 1, photochromic material 14 can be a photochromic initiator for one or more additional ring-opening cyclic monomers (generally indicated as 16), which may be the same or different from cyclic monomer 10, to form a photochromic material (generally indicated as 18) according to various non-limiting embodiments disclosed herein. Although not limiting herein, for example, in FIG. 1, k can be an integer ranging from 0 to 499 and photochromic material 18 can comprises the residue of from 1 to 500 ring-opening cyclic monomers, each of which may be the same or different from the remaining ring-opening cyclic monomers.

As discussed above, the photochromic materials according various non-limiting embodiments disclosed herein can comprise the reaction product of a plurality ring-opening cyclic monomers and at least one photochromic initiator. Additionally, as discussed above, the ring-opening cyclic monomers can be the same or different. For example, although not limiting herein, according to one non-limiting embodiment, each of the plurality of ring-opening cyclic monomers can be independently chosen from ε-caprolactone and δ-valerolactone. Further, according to this non-limiting embodiment, one of the ring-opening cyclic monomers can be ε-caprolactone and another can be δ-valerolactone. Thus, according to this non-limiting embodiment, the photochromic material can comprises a polymer chain segment that is a homopolymer of either α-caprolactone or δ-valerolactone, or a copolymer (e.g., a random, alternating, or block copolymer) of ε-caprolactone and δ-valerolactone.

As previously discussed, the photochromic initiators according to various non-limiting embodiments disclosed herein comprise at least one functional group adapted to initiate ring-opening of at least one cyclic monomer and can be adapted to initiate ring-opening polymerization of a plurality of ring-opening cyclic monomers. Examples of functional groups that are suitable for use in conjunction with various non-limiting embodiments disclosed herein include, without limitation, alcohols, amines, carboxylic acids, silanols, thiols, and combinations, salts and complexes thereof. According to one non-limiting embodiment, the photochromic initiator comprises at least one functional group chosen from a primary alcohol group, a secondary alcohol group, and salts and complexes thereof. However, as discussed above, the choice of functional group will depend, in part, upon the ring-opening cyclic monomers.

Specific non-limiting examples of photochromic initiators that can be used in conjunction with various non-limiting embodiments disclosed herein are set forth in Table 1, below. It should be appreciated that Table 1 is not intended to be an exhaustive listing of all suitable photochromic initiators and is presented for illustration purposes only. Those skilled in the art will recognize various other photochromic initiators and modification of those photochromic initiators listed below, which are within the spirit and scope of the present disclosure, and that can be used in conjunction with the various non-limiting embodiments disclosed herein.

TABLE 1

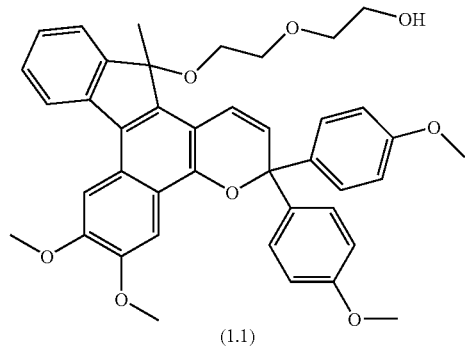

(1.1)

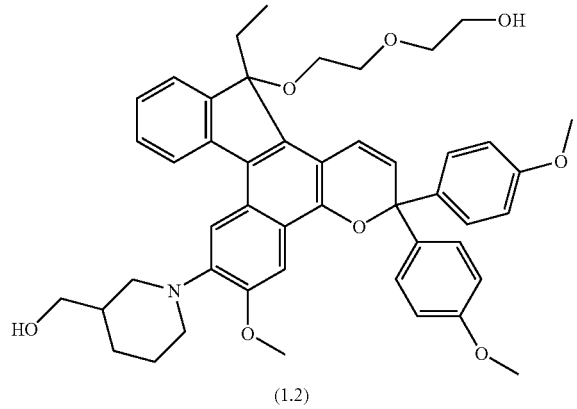

(1.2)

TABLE 1-continued
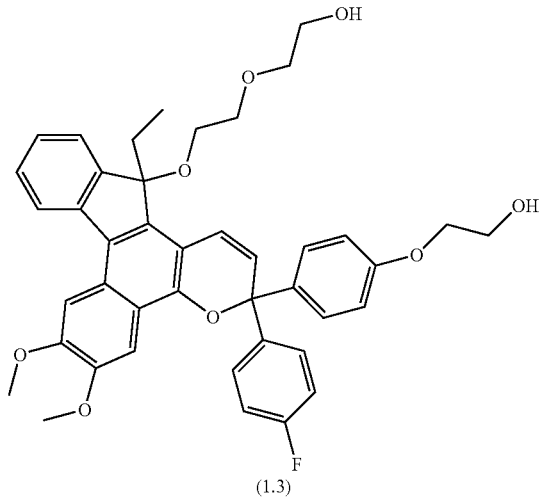
(1.3)
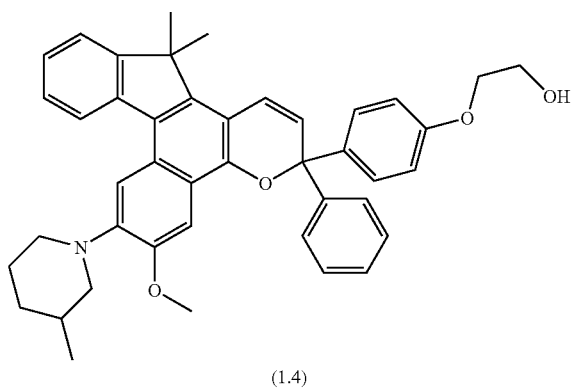
(1.4)
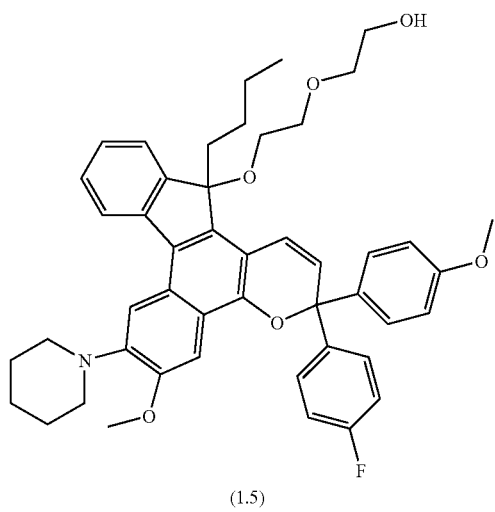
(1.5)

TABLE 1-continued
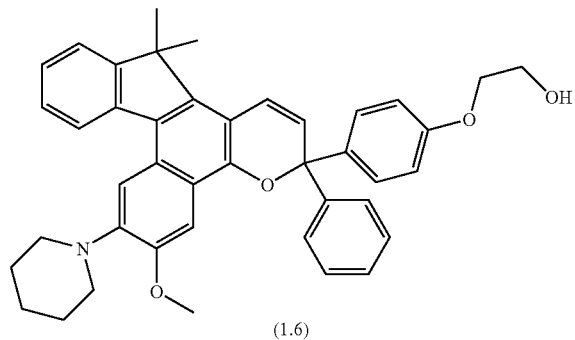
(1.6)
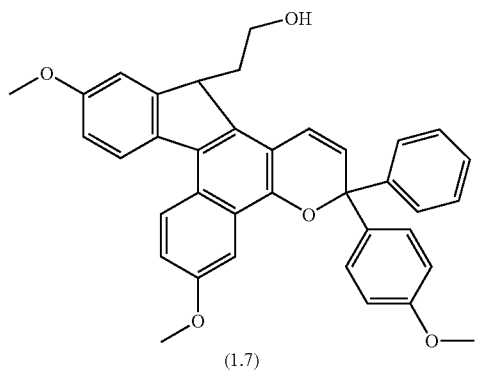
(1.7)
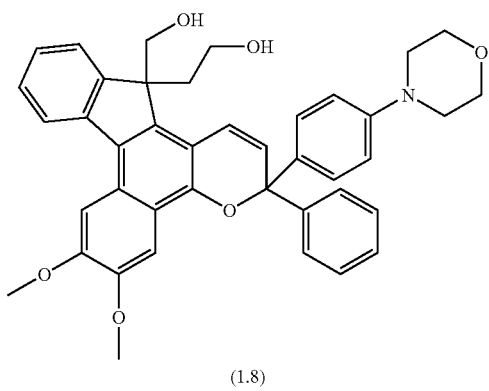
(1.8)
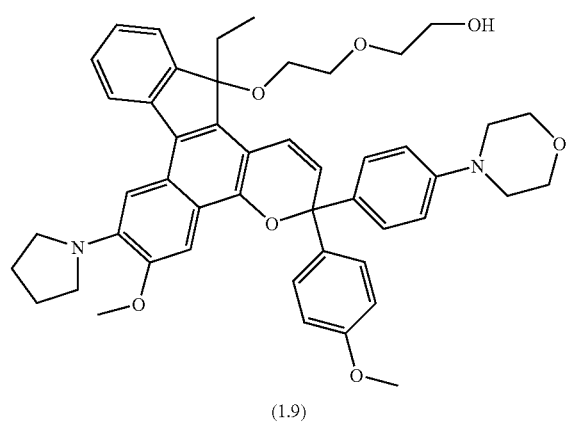
(1.9)

TABLE 1-continued
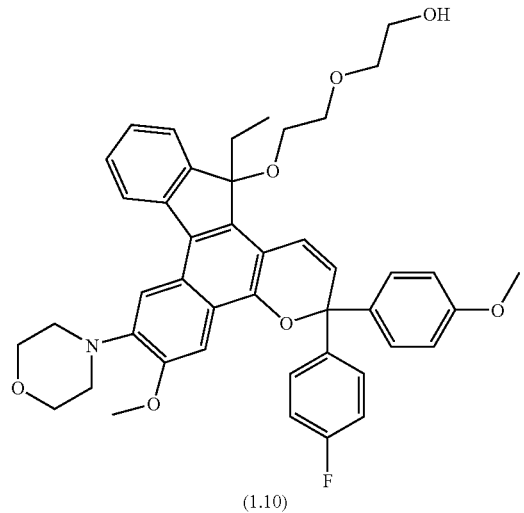
(1.10)
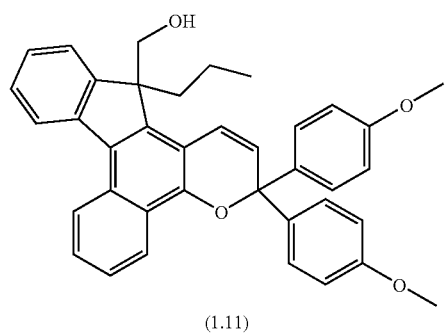
(1.11)
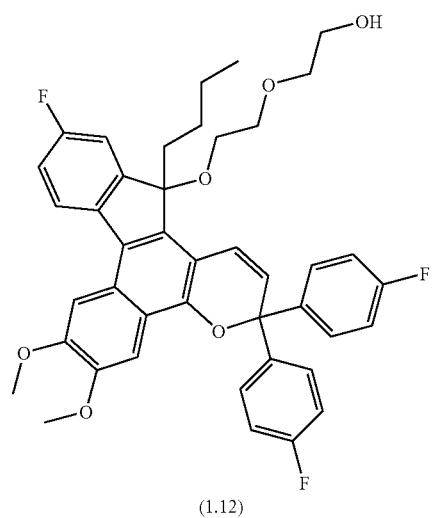
(1.12)

TABLE 1-continued
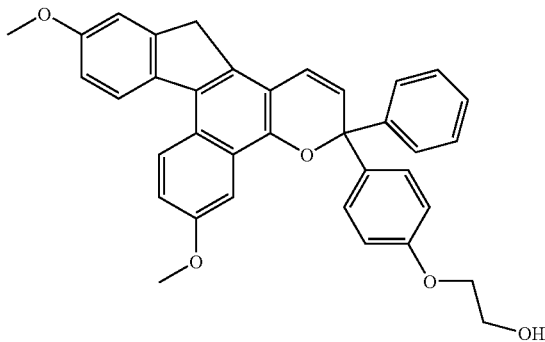
(1.13)
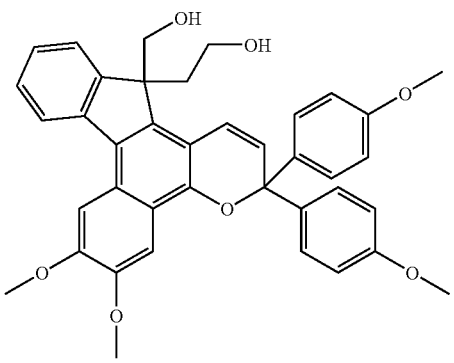
(1.14)
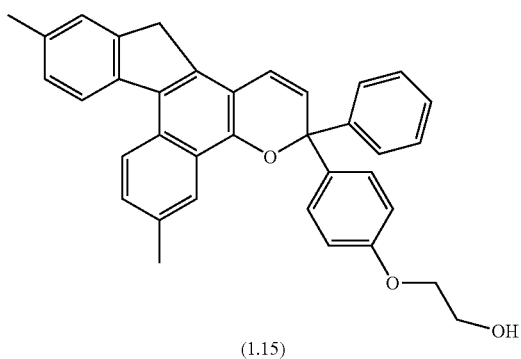
(1.15)
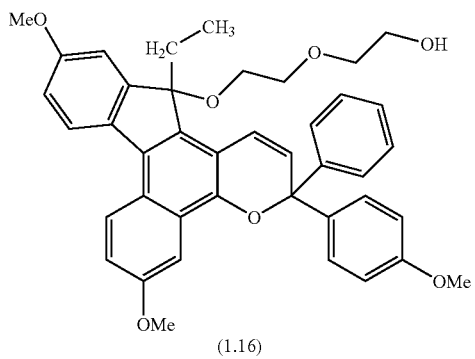
(1.16)

TABLE 1-continued
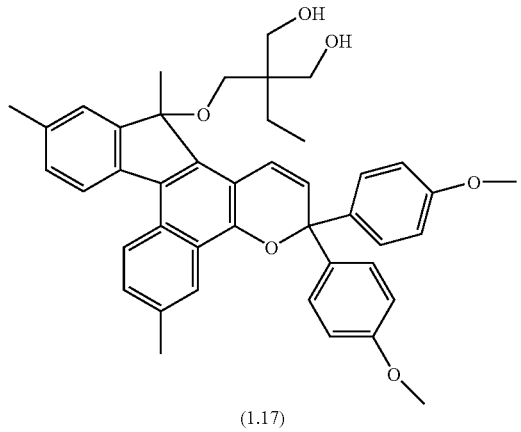
(1.17)
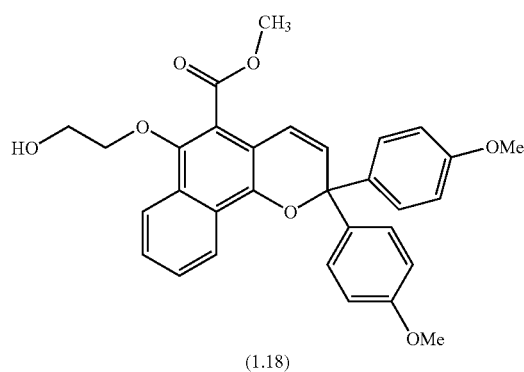
(1.18)
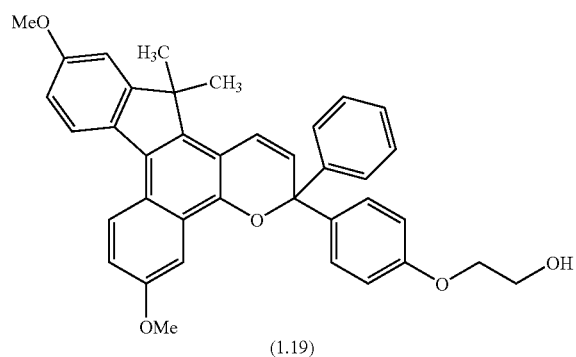
(1.19)
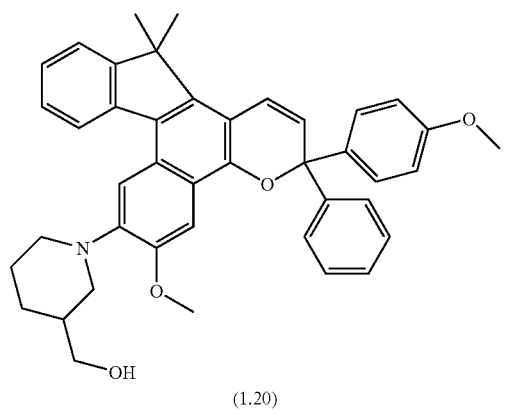
(1.20)

TABLE 1-continued
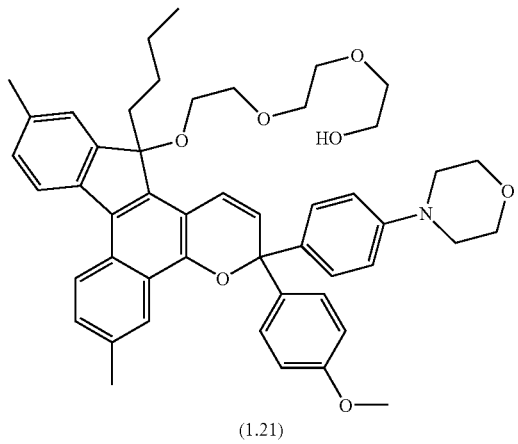
(1.21)
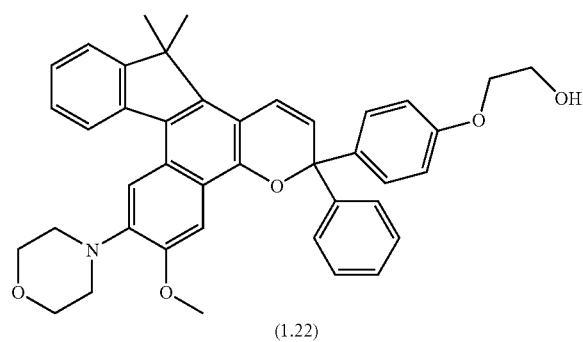
(1.22)
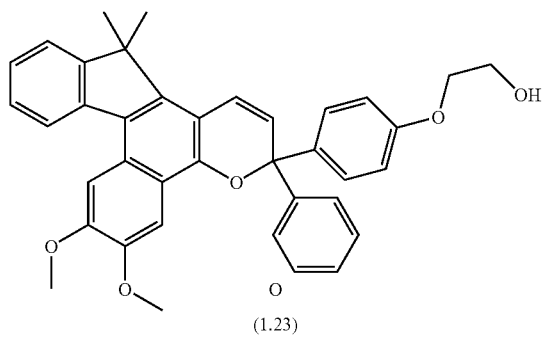
(1.23)
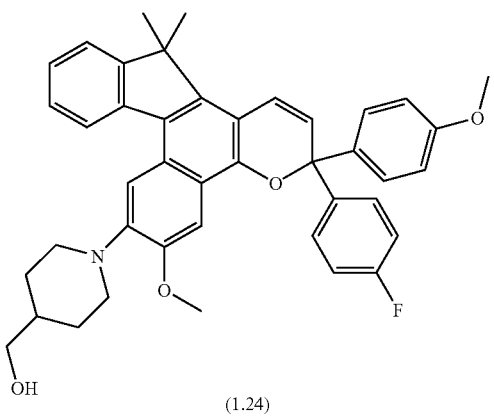
(1.24)

TABLE 1-continued
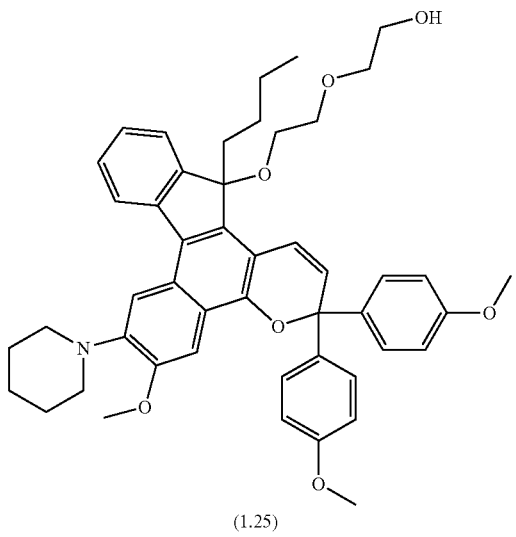
(1.25)
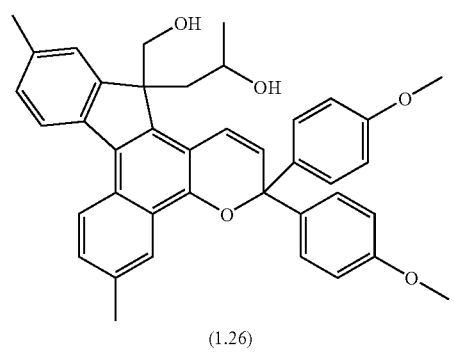
(1.26)
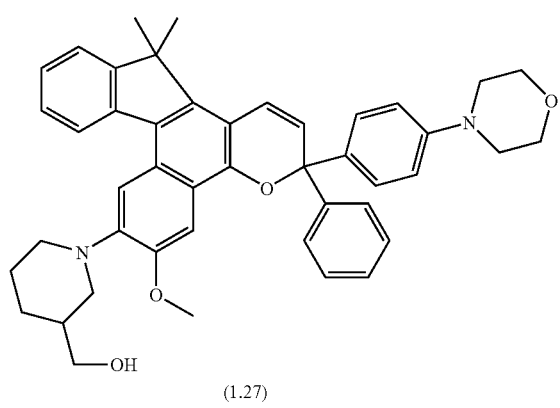
(1.27)

TABLE 1-continued
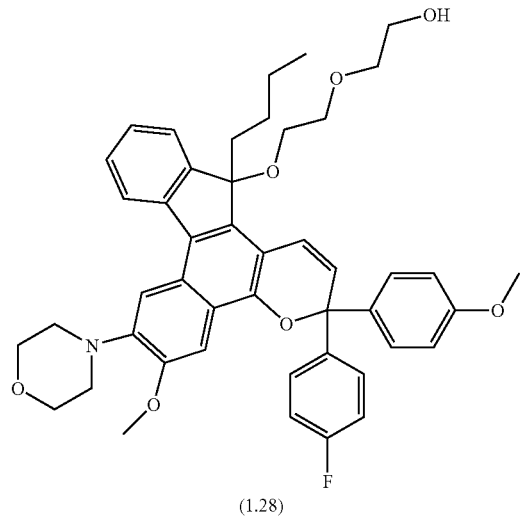
(1.28)
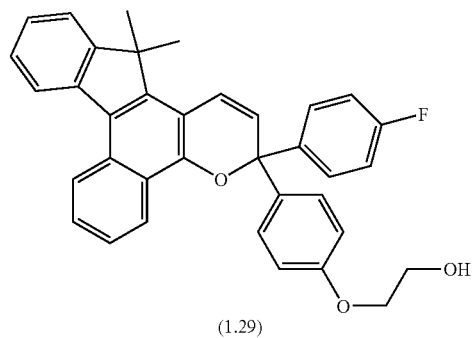
(1.29)
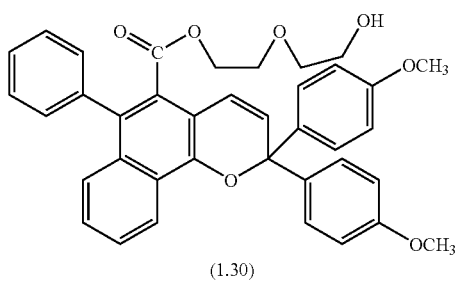
(1.30)
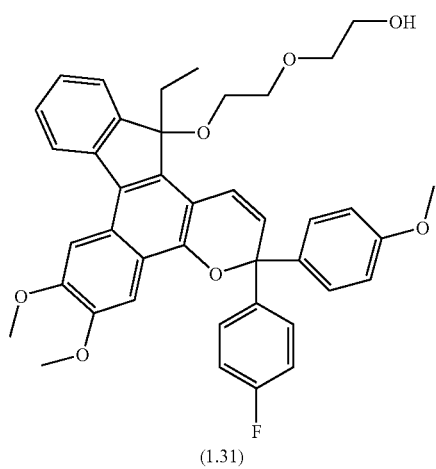
(1.31)

TABLE 1-continued
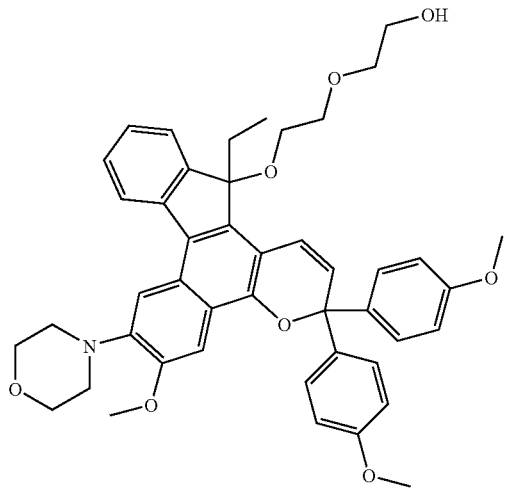
(1.32)
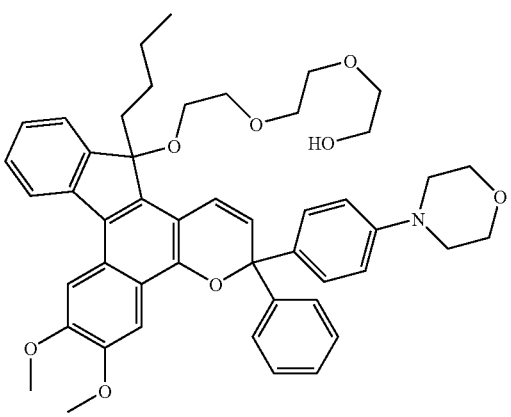
(1.33)
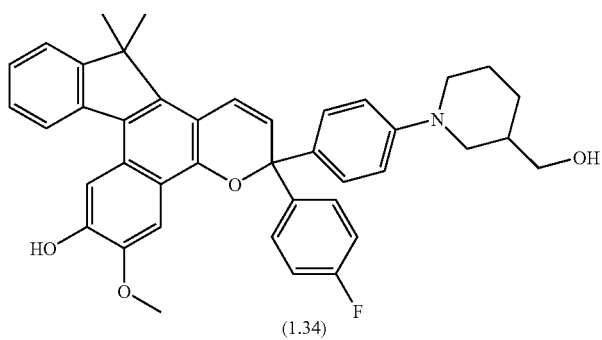
(1.34)

TABLE 1-continued
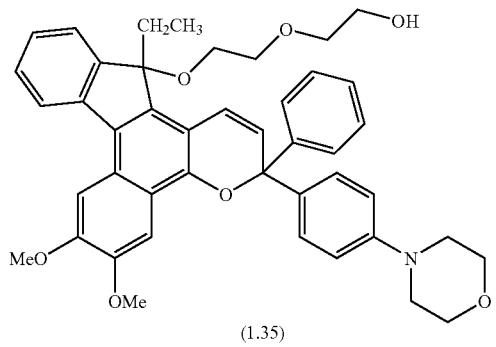
(1.35)
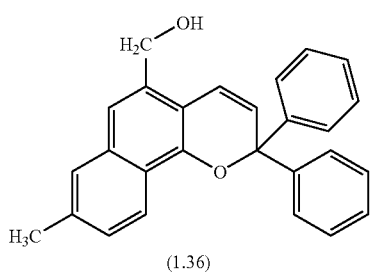
(1.36)
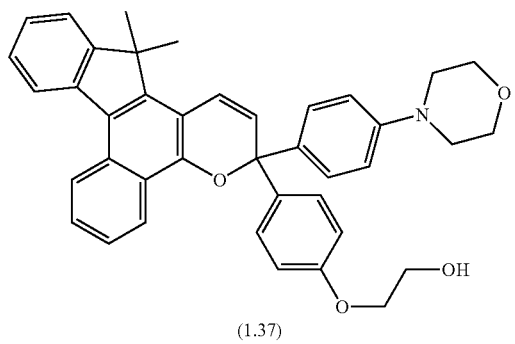
(1.37)
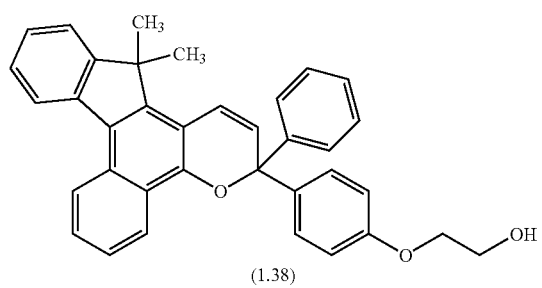
(1.38)
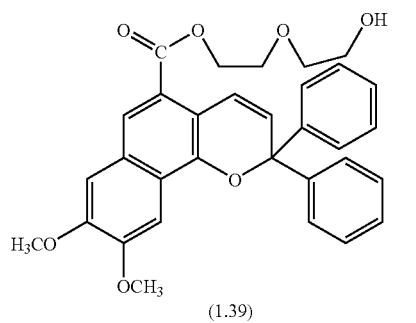
(1.39)

TABLE 1-continued
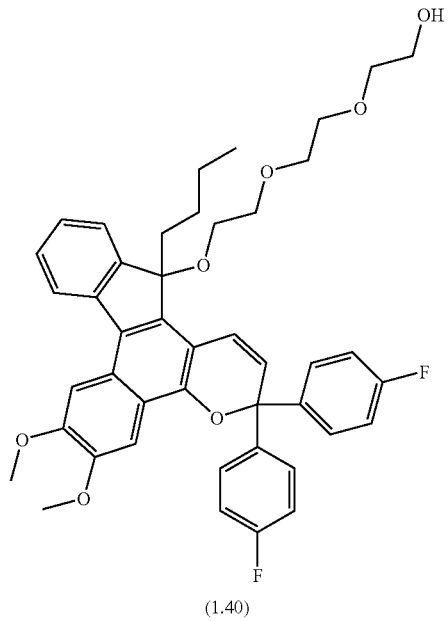
(1.40)
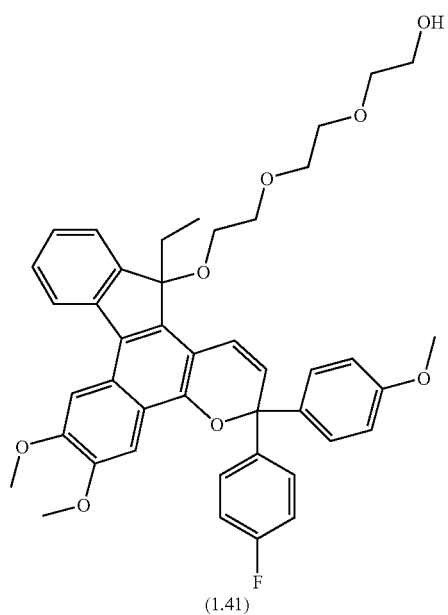
(1.41)
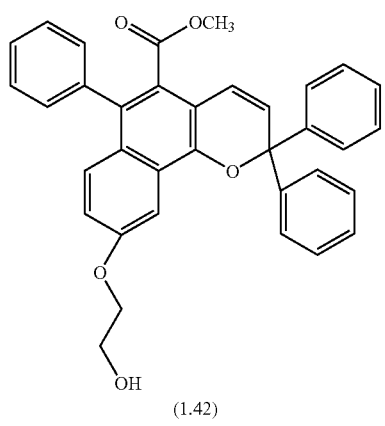
(1.42)

TABLE 1-continued
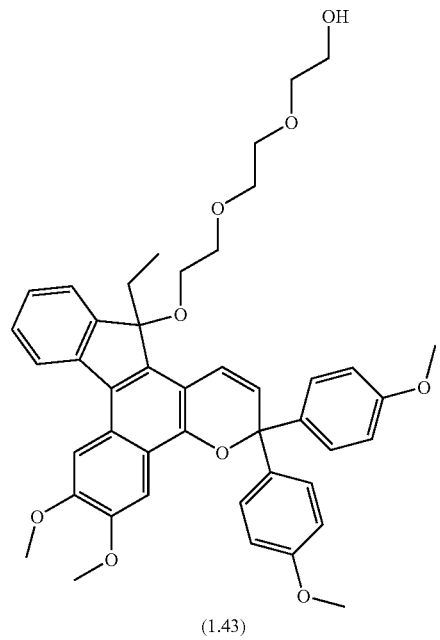
(1.43)
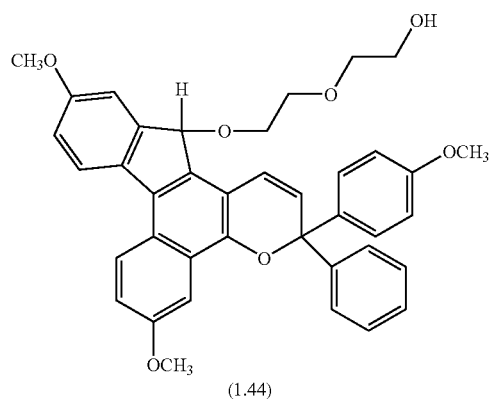
(1.44)
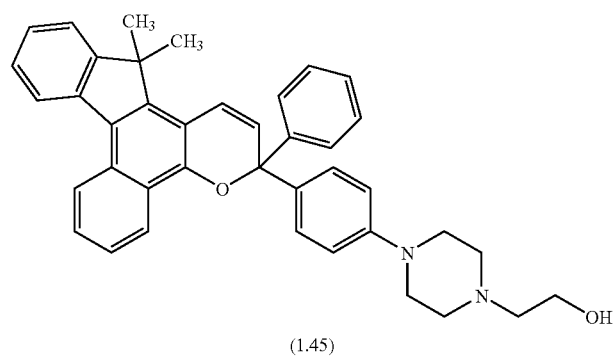
(1.45)

TABLE 1-continued
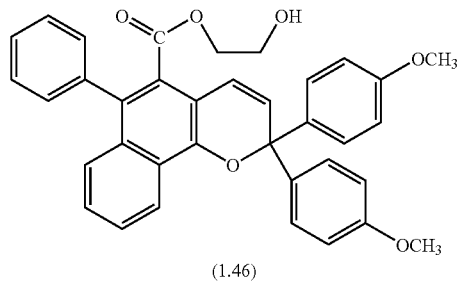
(1.46)
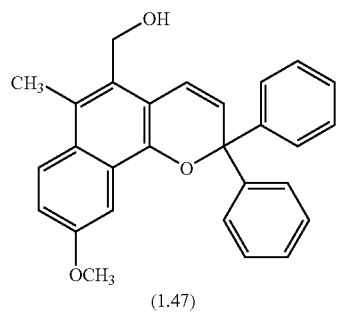
(1.47)
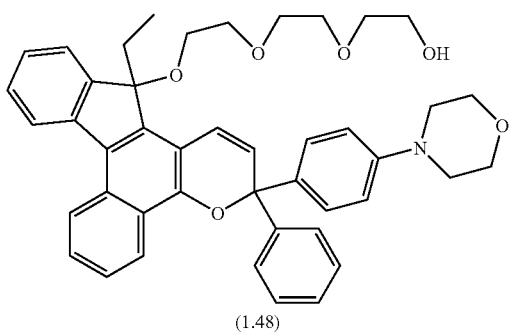
(1.48)
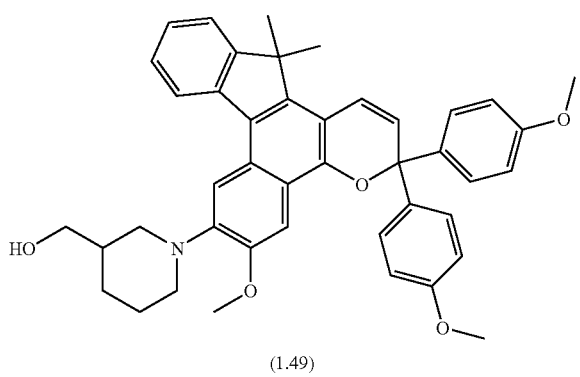
(1.49)
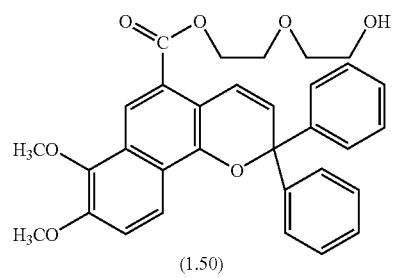
(1.50)

TABLE 1-continued
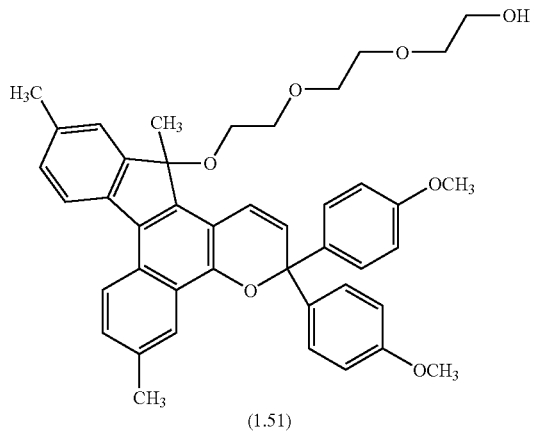
(1.51)
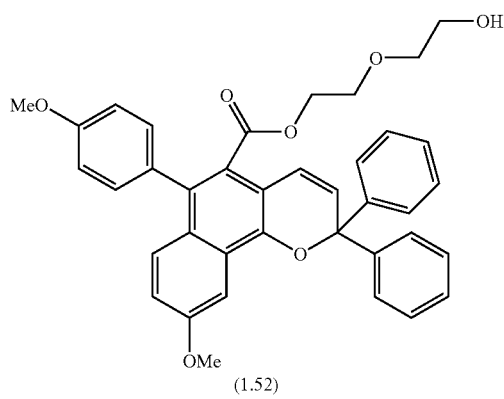
(1.52)
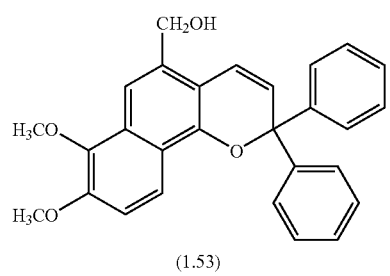
(1.53)
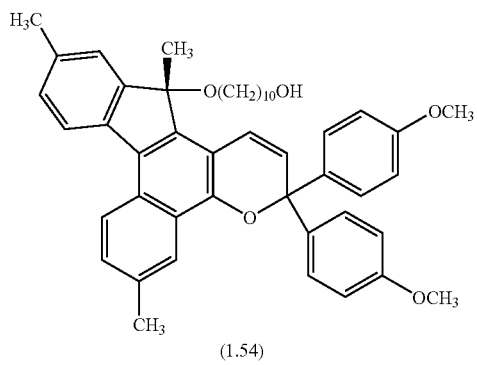
(1.54)

TABLE 1-continued
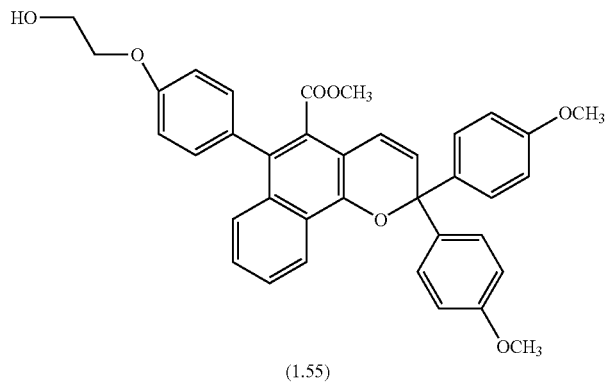
(1.55)
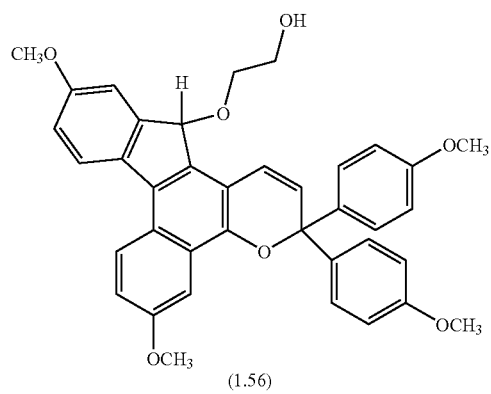
(1.56)
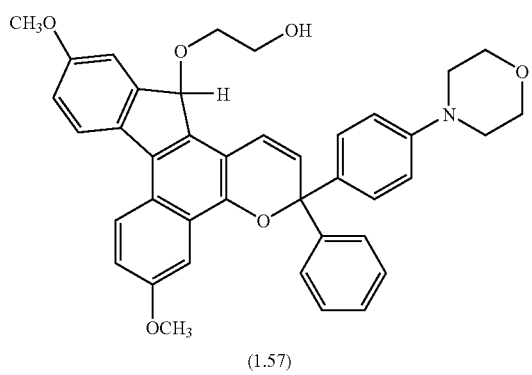
(1.57)
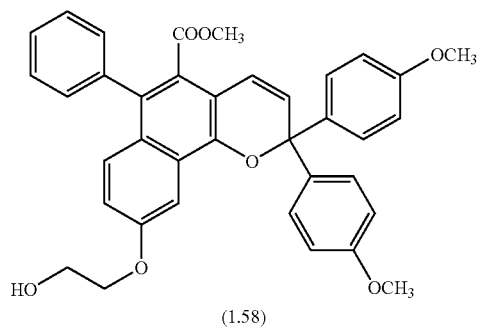
(1.58)

TABLE 1-continued
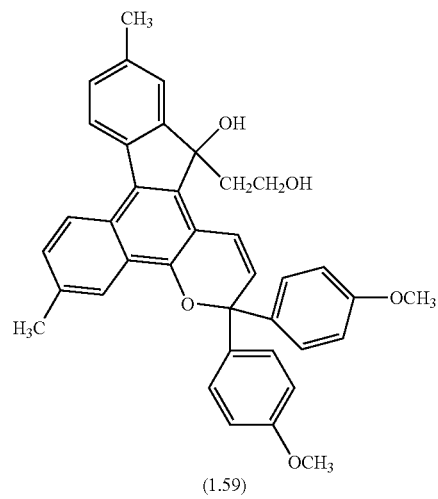
(1.59)
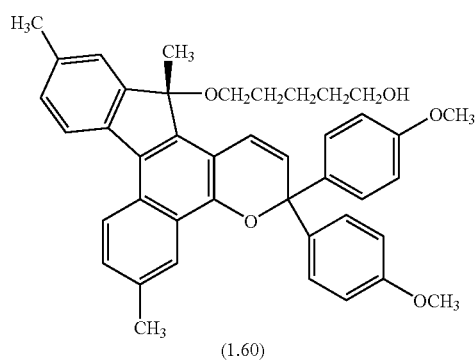
(1.60)
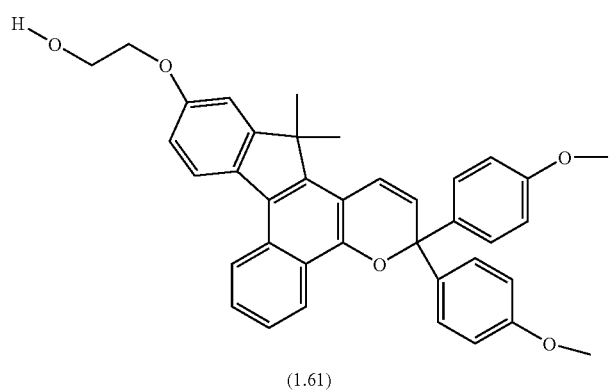
(1.61)

TABLE 1-continued
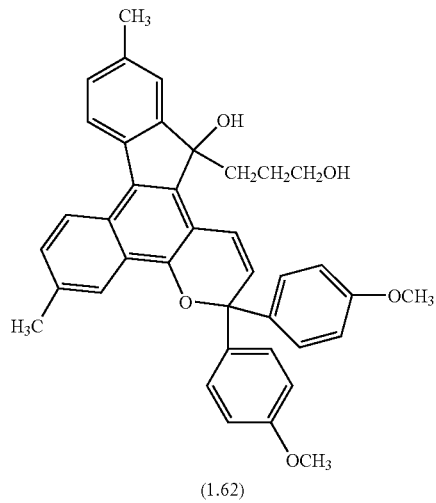
(1.62)
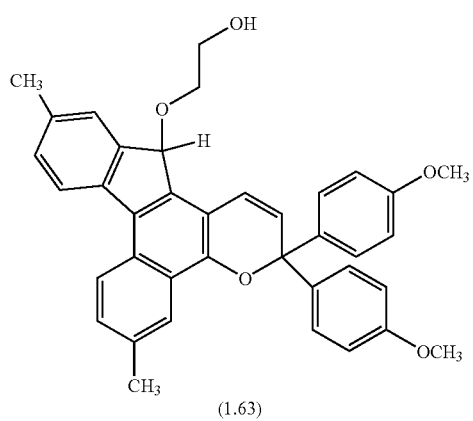
(1.63)
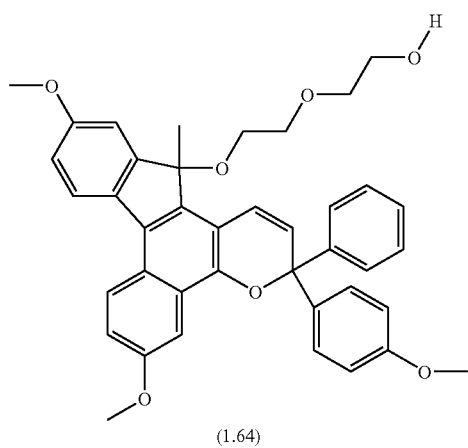
(1.64)

TABLE 1-continued
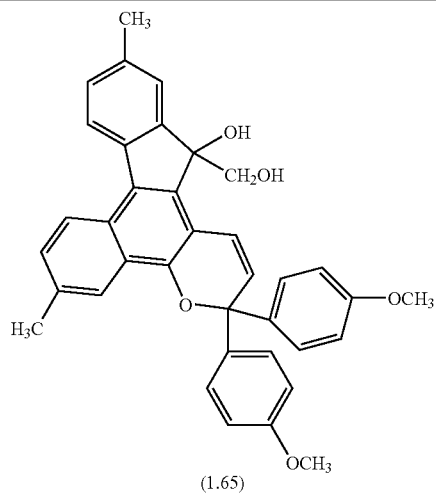
(1.65)
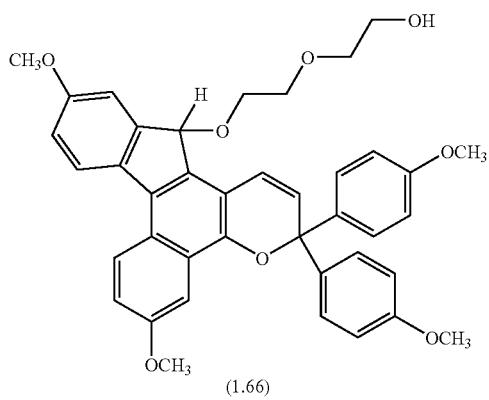
(1.66)
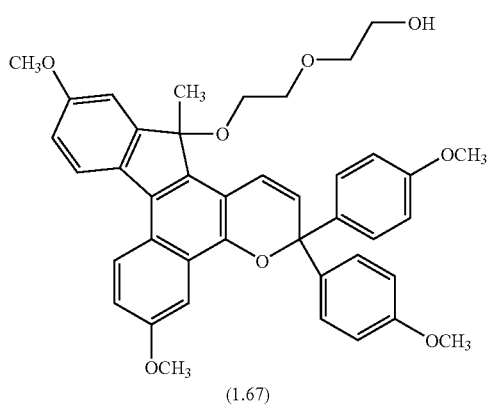
(1.67)
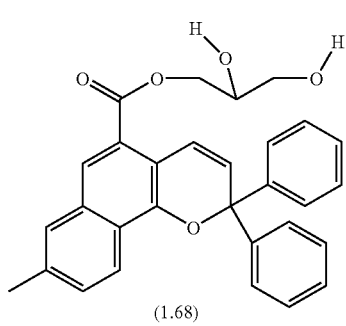
(1.68)

TABLE 1-continued
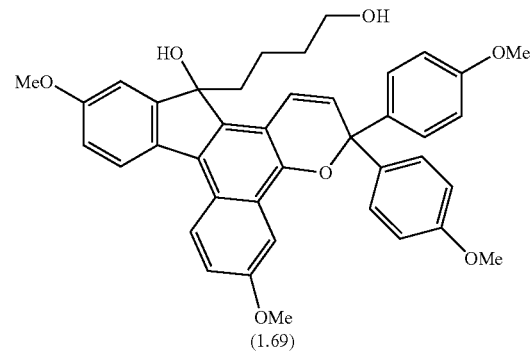
(1.69)
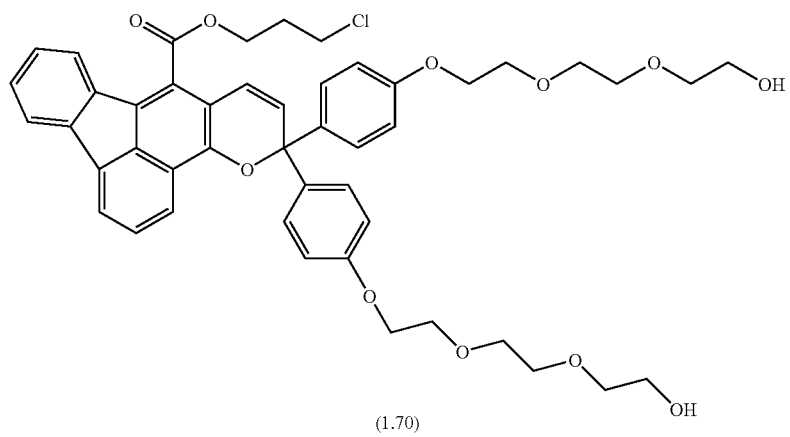
(1.70)
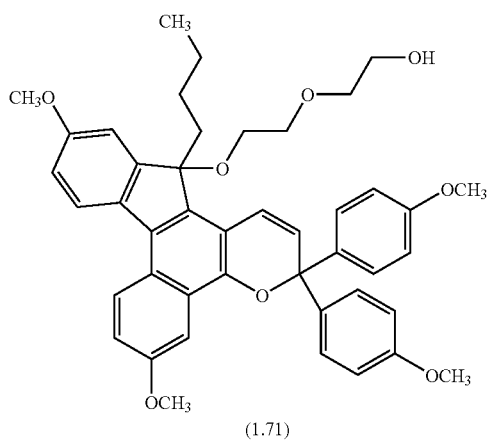
(1.71)
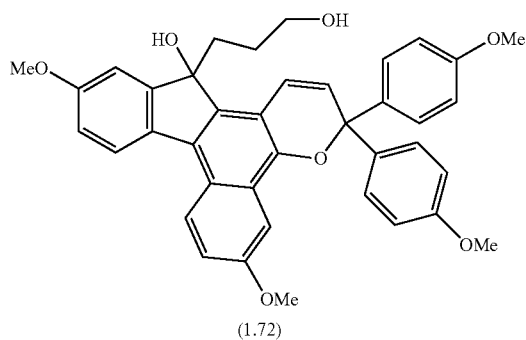
(1.72)

TABLE 1-continued
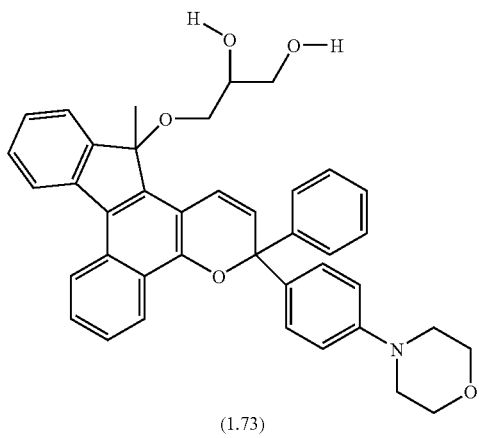
(1.73)
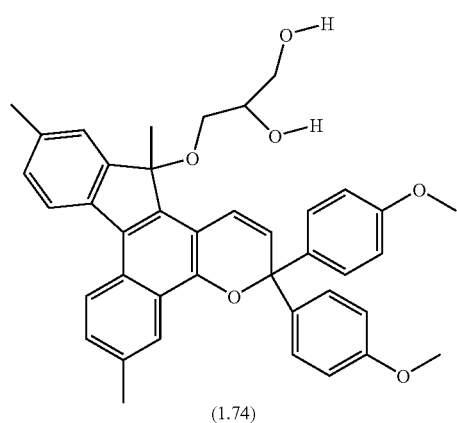
(1.74)
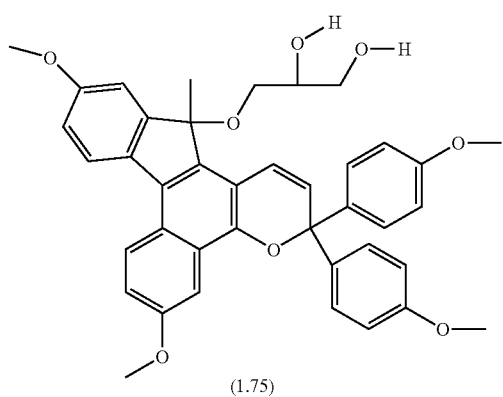
(1.75)
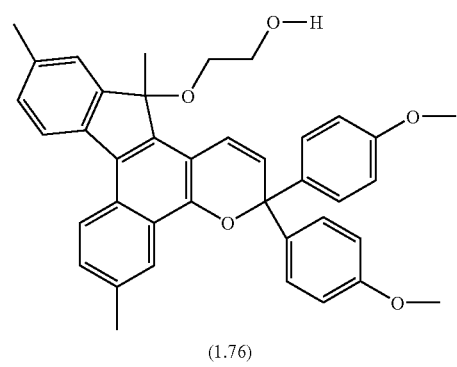
(1.76)

TABLE 1-continued
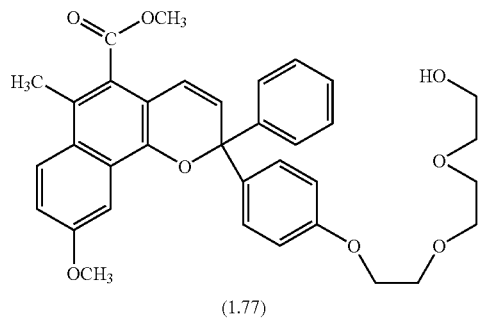
(1.77)
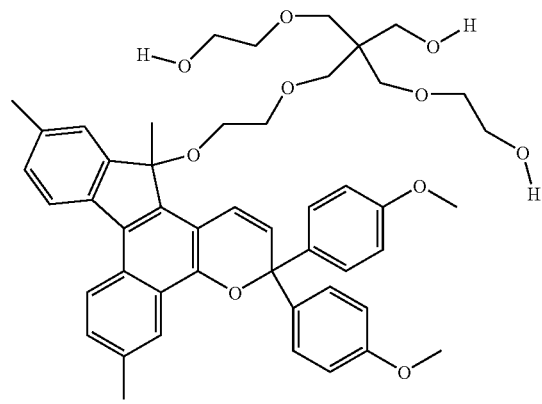
(1.78)
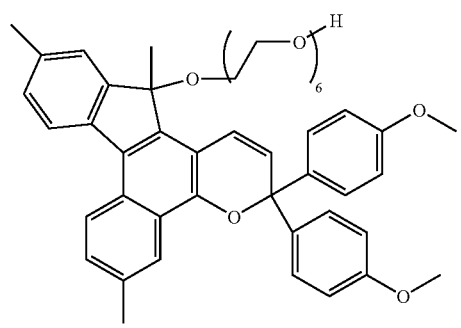
(1.79)
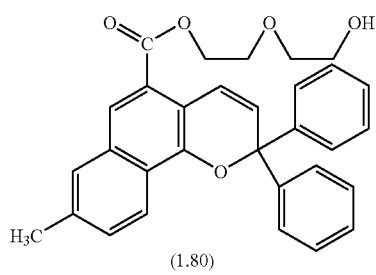
(1.80)

TABLE 1-continued
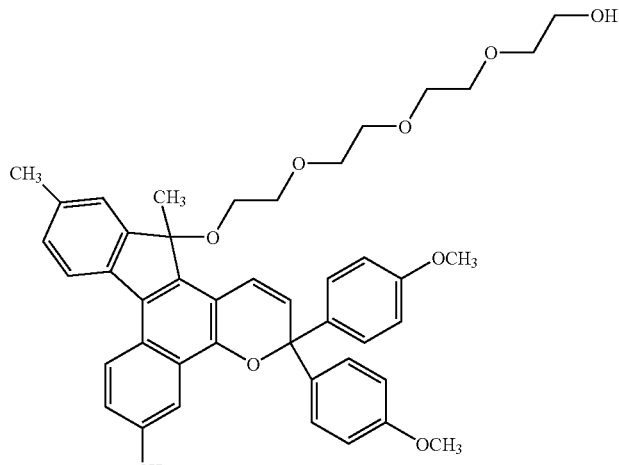
(1.81)
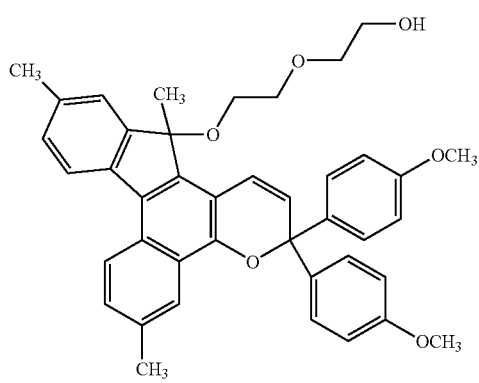
(1.82)
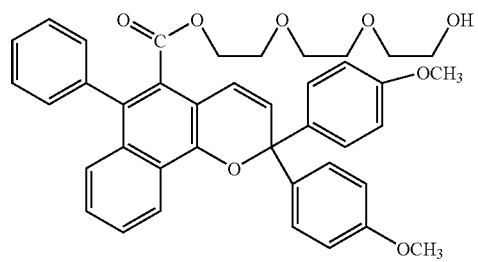
(1.83)
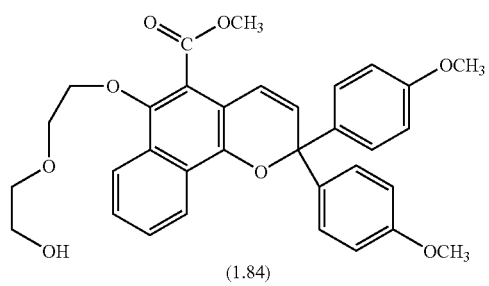
(1.84)

TABLE 1-continued

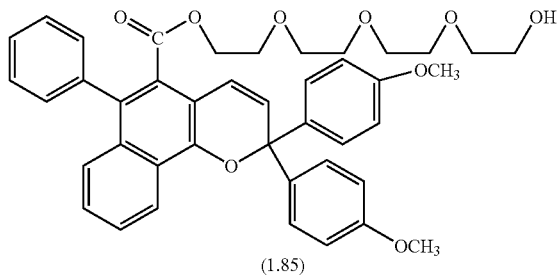

(1.85)

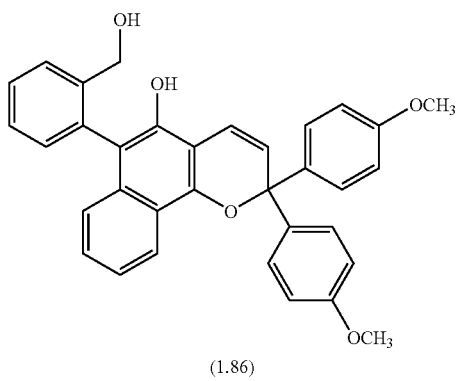

(1.86)

Methods of forming these and other non-limiting photochromic initiators will be readily understood by those skilled in the art in view of the present disclosure and examples. For example, although not limiting herein, one method of forming a 2,2-bis(4-methoxyphenyl)-5-methoxycarbonyl-6-hydroxy-[2H]-naphtho[1,2-b]pyran that can be used in preparing photochromic initiators such as 1.18 and 1.84 (shown above in Table 1) can be found in Example 1 of U.S. Pat. No. 5,458,814 at col. 13, lines 15-52, which example is hereby specifically incorporated by reference.

Figure 2:
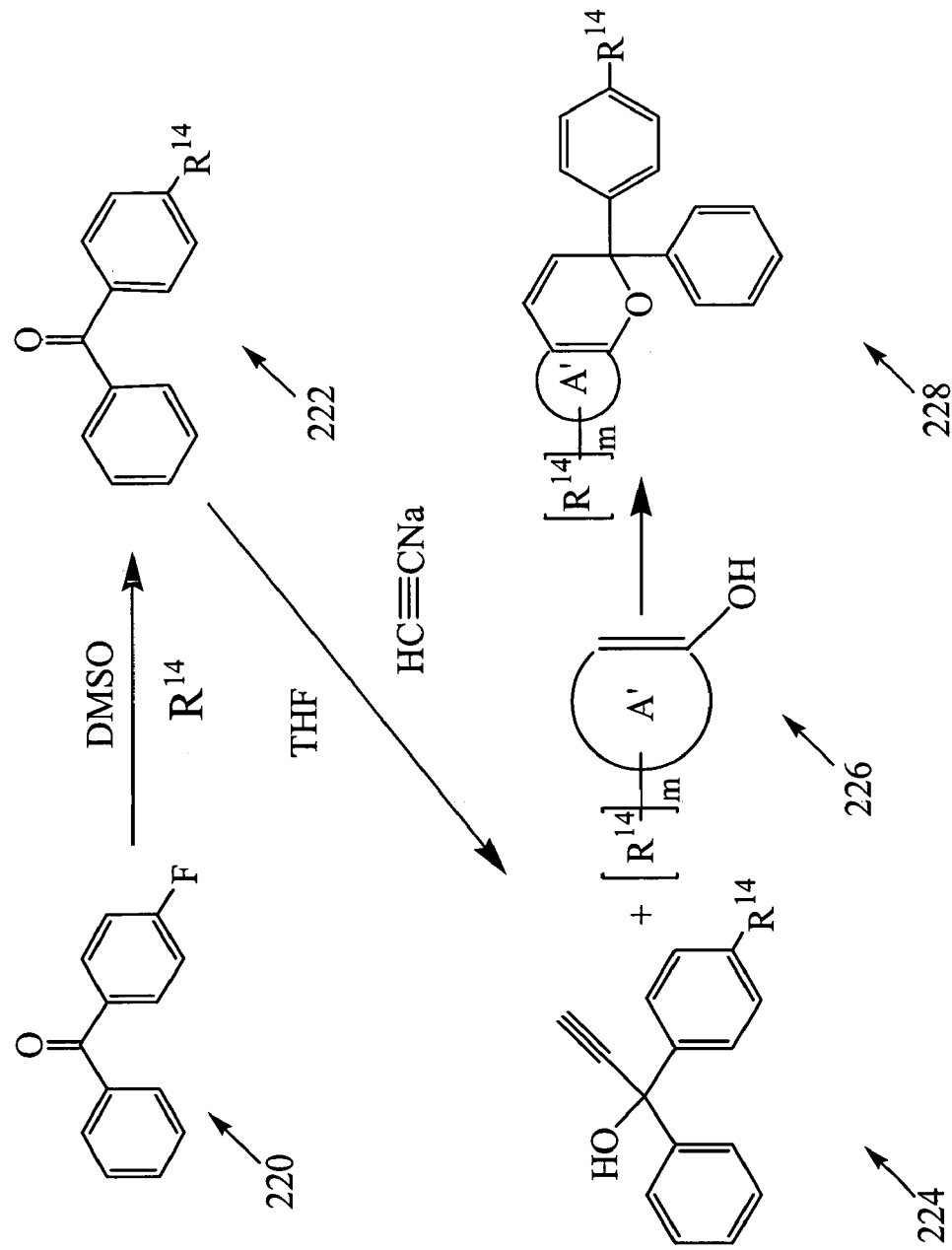
FIGS. 2 and 3 are schematic depictions of various routes for preparing photochromic initiators that can be used in conjunction with various non-limiting embodiments disclosed herein.
Figure 3:
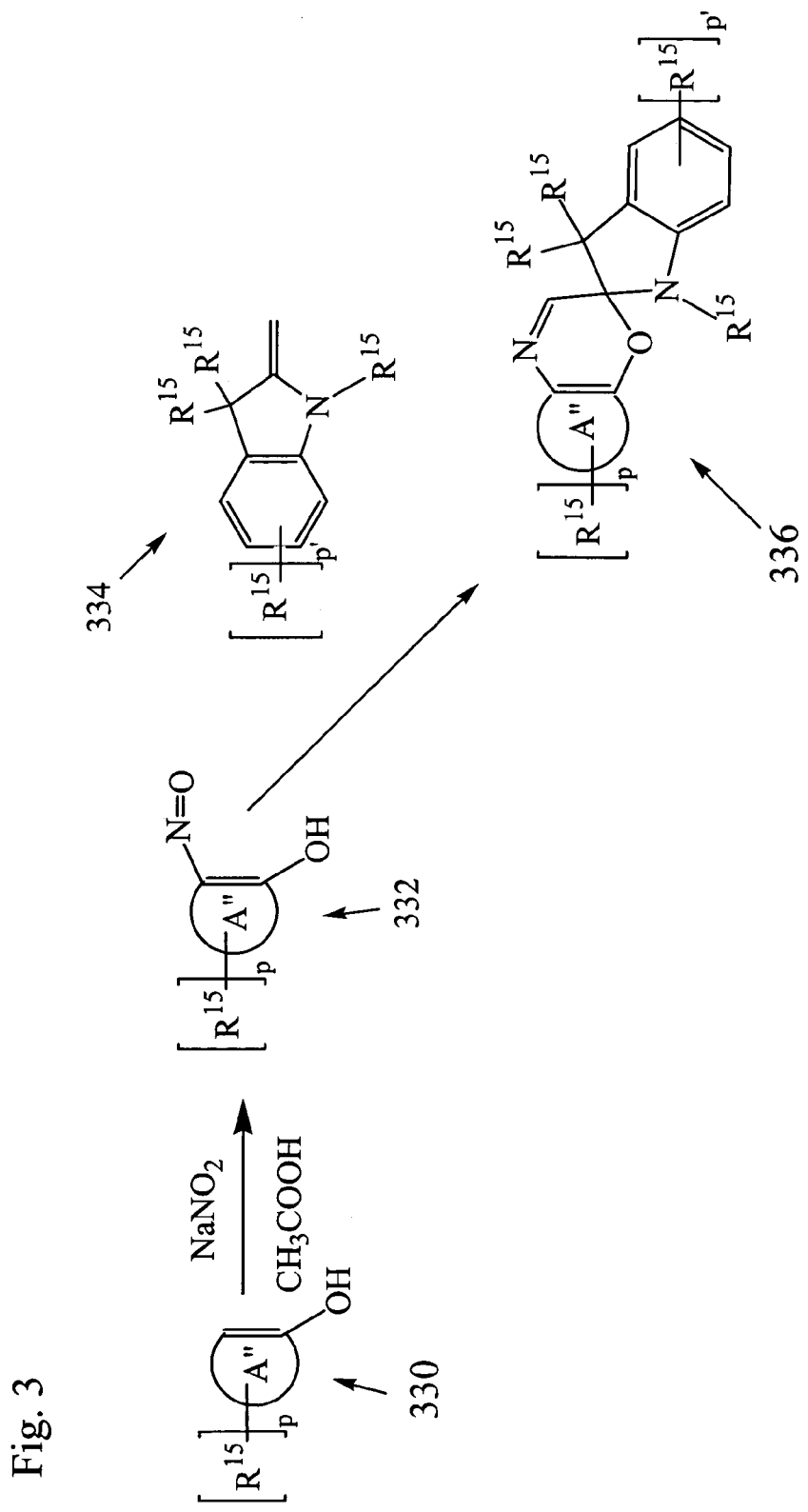

General reaction schemes for forming photochromic pyran initiators and photochromic oxazines initiators that can be used in conjunction with various non-limiting embodiments disclosed herein are set forth in FIGS. 2 and 3, respectively. It should be appreciated that the general reaction schemes depicted in FIGS. 2 and 3 are not intended to be limiting herein and are meant for illustration purposes only. Those skilled in the art will recognize that, in addition to the general reaction schemes shown in FIGS. 2 and 3 and modifications thereof, other methods can be used to form suitable photochromic initiators that can be used in accordance with various non-limiting embodiments disclosed herein.

FIG. 2 schematically depicts a general reaction scheme for preparing a photochromic pyran comprising at least one functional group adapted to initiate ring-opening of at least one ring-opening cyclic monomer. In FIG. 2, 4-fluorobenzophenone, which is generally indicated as 220 in FIG. 2, can be reacted under nitrogen in the anhydrous solvent dimethyl sulfoxide (DMSO) with an organic group comprising at least one functional group adapted to initiate ring-opening of at least one cyclic monomer ("$R^{14}$"), to form the substituted ketone generally indicated as 222. For example, while not limiting herein, $R^{14}$ can be a linear or branched group comprising a functional group chosen from an alcohol, an amine, a carboxylic acid, a silanol, a thiol, or combinations, salts and complexes thereof. It will be appreciated by those skilled in the art that 4-fluorobenzophenone can either be purchased or prepared by Friedel-Crafts methods known in the art. For example, see the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992, which are hereby specifically incorporated by reference herein. Thereafter, substituted ketone 222 can be reacted with sodium acetylide in a suitable solvent, such as but not limited to anhydrous tetrahydrofuran (THF), to form the corresponding propargyl alcohol (generally indicated as 224). Propargyl alcohol 224 can then be coupled with a hydroxy substituted A' group (generally indicated as 226) to form the photochromic pyran initiator, generally indicated as 228. Suitable non-limiting examples of A' groups include naphtho, benzo, phenanthro, fluorantheno, antheno, quinolino, indenonaphtho, heterocyclic-fused naphtho, and heterocyclic-fused benzo. Further, as depicted in FIG. 2, optionally, the A' group can be substituted with one or more $R^{14}$ groups (e.g., m can be 0 to the total number of available positions), and each $R^{14}$ can be the same or different from the remaining $R^{14}$ groups.

FIG. 3 schematically depicts a general reaction scheme for preparing a photochromic oxazine comprising at least one functional group adapted to initiate ring-opening of at least one cyclic monomer. In FIG. 3 a general nitrosation and coupling process is shown in which a hydroxylated A" group, generally indicated as 330, is reacted with sodium nitrite in the presence of an acid, such as but not limited to acetic acid, to produce the nitroso-substituted A"group generally indicated as 332. Suitable non-limiting examples of A" groups include naphtho, benzo, phenanthro, fluorantheno, antheno, quinolino, indenofused naphtho, heterocyclic-fused naphtho, and heterocyclic-fused benzo. Optionally, the A" group can be substituted with one or more organic groups comprising a functional group adapted to initiate a ring-opening reaction ("$R^{15}$"). Nitroso-substituted A" group 332 is then coupled with a Fischer's base, generally indicated as 334, which may also comprise one or more groups $R^{15}$. Coupling is conducted in a solvent, such as but not limited to absolute ethanol, and heated under reflux conditions to produce the photochromic oxazine initiator, generally indicated as 336. Further, in FIG. 3, p and p' can range from 0 to the total number of available positions on the molecule to which the group is attached, provided that at least one functional group adapted to initiate ring-opening is present, and each $R^{15}$ group can be the same or different from the remaining $R^{15}$ groups.

As previously discussed, once a ring-opening cyclic monomer is opened with an appropriate initiator, the ring-opened monomer can serve to initiate ring opening of another ring-opening cyclic monomer, and so on. Accordingly, once the photochromic initiator initiates ring-opening of at least one ring-opening cyclic monomer, the resultant photochromic material can serve as a photochromic initiator for yet another ring-opening cyclic monomer. In this manner a photochromic material comprising at least one polymer chain comprising a plurality of ring-opened cyclic monomers, which may be the same or different, can be formed. Thus, for example, any of the photochromic initiators listed above in Table 1 can be reacted with one or more cyclic monomers to form still other photochromic initiators that are suitable for use in conjunction with various non-limiting embodiments disclosed herein.

Additionally, the photochromic materials according to various non-limiting embodiments disclosed herein can be further reacted with an organic material comprising at least one reactive group such that the resultant photochromic material further comprises an organic material comprising the residue of at least one reactive group. As used herein the term "reactive group" means any group capable of being reacted with a hydroxyl group, either with or without a catalyst. Further, as used herein the term "residue of a reactive group" means that which remains after a reactive group has been reacted.

Non-limiting examples of suitable organic materials comprising at least one reactive group that can be used in conjunction with various non-limiting embodiments disclosed herein include those set forth in Table 2 below. Non-limiting examples of reactions in which the organic material comprising the at least one reactive group may participate include addition reactions, elimination reactions, condensation reactions, substitution reactions, and polymerization reactions (e.g., radical polymerization, anionic polymerization, cationic polymerization, ring-opening polymerization, condensation polymerization, addition polymerization, and such polymerization processes that are described in *Ullmann's Encyclopedia of Industrial Chemistry*, "Polymerization Processes," Vol. 21A, at pages 305 to 428, which are hereby specifically incorporated by reference). Other specific non-limiting reactions are set forth below in Table 2. Non-limiting examples of the residue of the at least one reactive group which is obtained after reacting the at least one reactive group are also shown below in Table 2. It should be appreciated that Table 2 is not intended to be an exhaustive listing of all suitable organic materials comprising at least one reactive group, possible reactions, and/or residues, and that Table 2 is presented for illustration purposes only. Those skilled in the art will recognize various other organic materials comprising at least one reactive group, possible reactions and residues, which are within the spirit and scope of the present disclosure, that can be used in conjunction with the various non-limiting embodiments disclosed herein.

As discussed above, after reaction with an organic material comprising at least one reactive group, the photochromic materials according to various non-limiting embodiments disclosed herein will further comprise an organic material comprising the residue of at least one reactive group. Non-limiting examples of residues of at least one reactive group, which the photochromic materials according to various non-limiting embodiments disclosed herein may comprise, include acrylates, alkyl groups, alkyl phosphonates, alkyl-dialkoxysilyl groups, alkyloxydialkylsilyl groups, allyl carbonates, amides, amines, anhydrides, aryl groups, aziridines, carboxylic acids, chloroformates, cycloaliphatic epoxides, epoxides, esters, halogens, hydroxy groups, isocyanates, isothiocyanates, methacrylates, propenyl ethers, residues of ring-opening cyclic monomers, trialkoxysilyl groups, thiranes, thiols, vinyl carbonates, vinyl ethers, vinylbenzyl ethers, and combinations thereof. Those skilled in the art will appreciate that depending upon the intended use of the photochromic material, the organic material comprising the at least one reactive group can be chosen such that the organic material comprising the residue of the reactive group can be further reacted with other materials or groups, such as but not limited to polymeric, pre-polymeric, and monomeric materials. Alternatively, the organic material comprising the at least one reactive group can be chosen such that the organic material comprising the residue of the reactive group is essentially non-reactive in subsequent use.

TABLE 2

| Organic Material Comprising Reactive Group(s) | Reaction Type | Residue of Reactive Group(s) |
| --- | --- | --- |
| methyl-3,4-epoxycyclohexanecarboxylate | Transesterification | Cycloaliphatic epoxide |
| Epichlorohydrin | Alkylation | Glycidyl ether |
| Phosgene | Phosgenation | Chloroformate |
| Vinylchloroformate | Acylation | Vinyl carbonate |
| Allylchloroformate | Acylation | Allyl carbonate |
| Chloroethylvinylether | Alkylation | Vinyl ether |
| Allylbromide | Akylation | Allyl ether |
| 4-Vinylbenzylchloride | Alkylation | Styryl (Styrene) |
| Acryloylchloride | Acylation | Acrylate |
| Methacrylic anhydride | Acylation | Methacrylate |
| 2-Isocyanatoethylmethacrylate | Carbamoylation | Methacrylate |
| Isocyanatopropyl-trimethoxysilane | Carbamoylation | Trimethoxysilyl |
| ((Chloromethyl)phenyl-ethyl)methyldimethoxysilane | Alkylation | Dimethoxysilyl |
| Isophorone diisocyanate | Carbamoylation | Isocyanate |
| 3-isopropenyl-α,α-dimethylbenzyl isocyanate | Carbamoylation | Isopropenylphenyl |
| 2-bromoethylisocyanate | Carbamoylation | Halogen |
| Phenyl isocyanate | Carbamolyation | Phenyl (aryl) |
| N-butyl bromide | Alkylation | Butyl (alkyl) |

Figure 4:
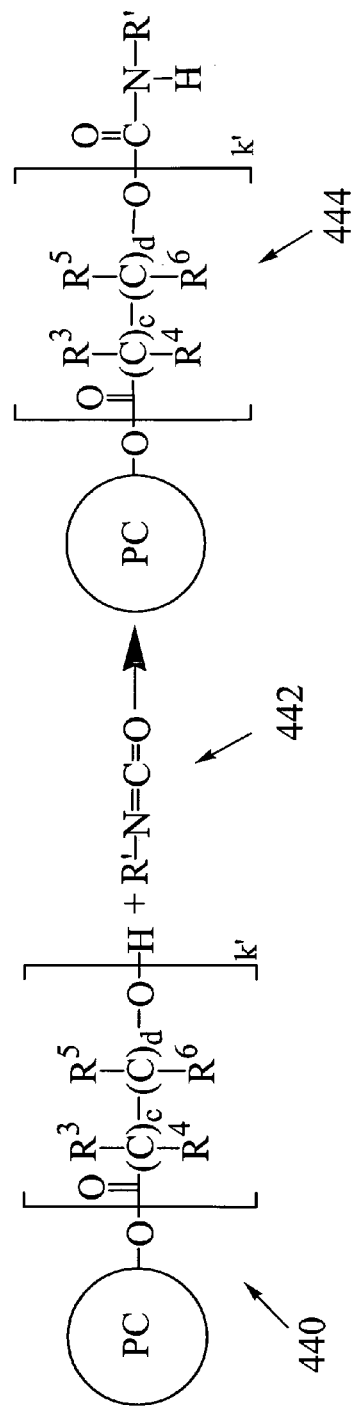

For example, although not limiting herein, as schematically depicted in FIG. 4, a photochromic material (generally indicated as 440) according to various non-limiting embodiments disclosed herein can be further-reacted with an organic material comprising a reactive group (generally indicated as 442) to form a photochromic material (generally indicated as 444) comprising an organic material comprising the residue of at least one reactive group. Although not limiting herein, as shown in FIG. 4, the organic material comprising the at least one reactive group 442 can be chosen such that the resultant residue of the at least one reactive group is essentially non-reactive. For example, although not limiting herein, organic material 442 can be a polymeric or pre-polymeric material comprising at least one reactive group, and the photochromic material can be bonded to the polymeric material by reacting the reactive group of the polymeric or pre-polymeric material with a hydroxyl group of the photochromic material. Further, although not limiting herein, in FIG. 4, k' can range from 1 to 500.

Figure 5:
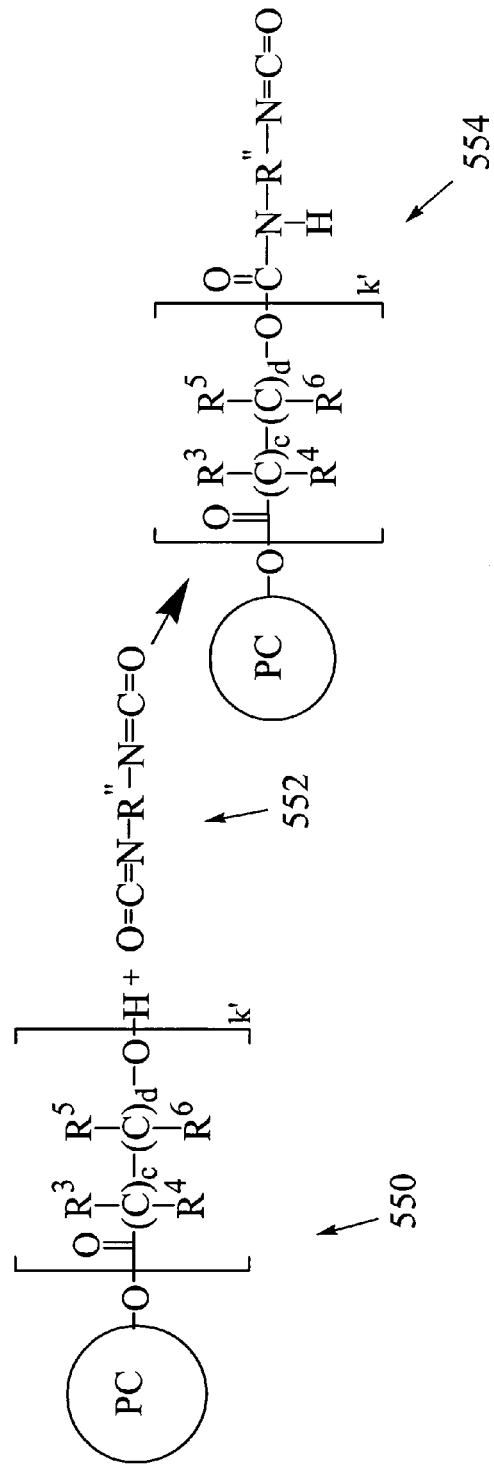

Alternatively, as discussed above, according to other non-limiting embodiments, the organic material comprising the at least one reactive group can be chosen such that the resultant photochromic material comprises an organic material comprising the residue of the at least one reactive group that can be further reacted with one or more additional materials or groups. For example, although not limiting herein, as schematically depicted in FIG. 5, the photochromic material (generally indicated as 550) according to various non-limiting embodiments disclosed herein can be further reacted with an organic material comprising two reactive groups (generally indicated as 552) to form a photochromic material (generally indicated as 554) comprising an organic material comprising the residue of at least one reactive group and an unreacted reactive group. As shown in FIG. 5, organic material 552 is a diisocyanate, and the resultant photochromic material 554 comprises an organic material comprising the residue of an isocyanate group and an unreacted isocyanate group. Further, although not shown in FIG. 5, the unreacted isocyanate group can be further reacted with one or more additional materials or groups, for example to form a polymer segment or to bond or link the photochromic material to another material, such as a polymeric material or a surface.

Figure 6:
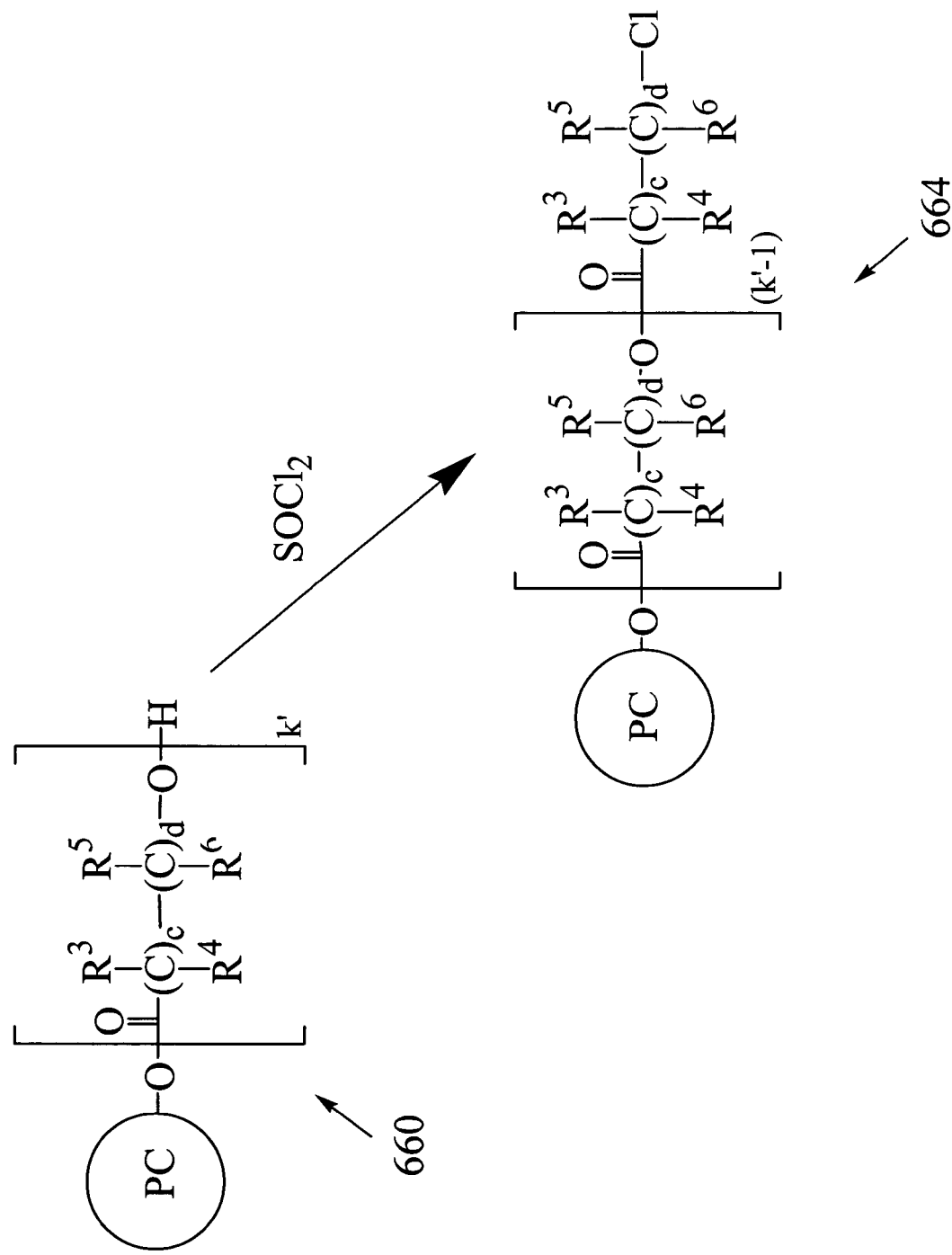

It will be appreciated by those skilled in the art that other methods of reacting the photochromic materials disclosed herein with organic materials comprising reactive groups and/or bonding a reactive group (or other functionality) to the photochromic materials according to various non-limiting embodiments disclosed herein can be employed, and that the aforementioned examples are provided for illustration purposes only and are not intended to be limiting herein. For example, although not limiting herein, as shown in FIG. 6, a photochromic material according to various non-limiting embodiments disclosed herein (generally indicated as 660) can be reacted in an halogenation reaction with an organic material comprising at least one reactive group (such as thionylchloride ($SOCl_2$) as shown in FIG. 6) to form a photochromic material (generally indicated as 664) comprising an organic material comprising the residue of a ring-opening cyclic monomer, in which the terminal hydroxyl group is substituted with a reactive group (such as chlorine as shown in FIG. 6).

Thus, one specific non-limiting embodiment disclosed herein provides a photochromic composition comprising a reaction product of (a) a photochromic material that is a reaction product of (1) at least one ring-opening cyclic monomer chosen from a cyclic ester and a cyclic carbonate, and (2) a photochromic initiator; and (b) an organic material comprising at least one reactive group. As discussed above, according to various non-limiting embodiments disclosed herein, the organic material comprising the at least one reactive group can be chosen, for example, so as to provide the photochromic material with a desired functionality or to link or bond the photochromic material to another group or material. For example, according to this non-limiting embodiment, the organic material comprising the at least one reactive group can be chosen such that, after reaction, the photochromic composition comprises an organic material comprising the residue of a reactive group bonded to the photochromic material, wherein the residue is chosen from an acrylate, an alkyl group, an alkyl phosphonate, an alkyldialkoxysilyl group, an alkyloxydialkylsilyl group, an allyl carbonate, an amide, an amine, an anhydride, an aryl group, an aziridine, a carboxylic acid, a chloroformate, a cycloaliphatic epoxide, an epoxide, an ester, a halogen, a hydroxy group, an isocyanate, an isothiocyanate, a methacrylate, a propenyl ether, a residue of a ring-opening cyclic monomer, a trialkoxysilyl group, a thiirane, a thiol, a vinyl carbonate, a vinyl ether, a vinylbenzyl ether, and combinations thereof.

Other non-limiting embodiments disclosed herein provide a photochromic material represented by:

$$PC \text{---} [S']_n \qquad \text{Formula 1}$$

wherein PC is a photochromic group, n is an integer chosen from 1 to 8; and each S' is independently chosen for each occurrence from a group represented by:

$$\text{---}[L]\text{---}\{[R^1]_a\text{---}R^2\}_b \qquad \text{Formula 2}$$

wherein (1) L is a linking group independently chosen for each occurrence from —O—, —N—, and —S—, or L comprises a linear or branched organic bridging group comprising at least one linking group that is independently chosen for each occurrence from —O—, —N—, and —S—; (2) the group $R^1$ is a ring-opened cyclic monomer, and (3) the group $R^2$ is independently chosen for each occurrence from hydrogen and an organic material comprising the residue of at least one reactive group. Further, in Formula 2, 'a' is an integer that is independently chosen for each occurrence from 1 to 500, and b is an integer that is independently chosen for each occurrence from 1 to 20.

As previously discussed, as used herein the term "photochromic group" refers to an organic entity comprising at least one photochromic moiety, and which may contain other organic groups or compounds (e.g., functional groups, and/or aliphatic, alicyclic, aromatic, and heterocyclic groups and compounds, etc.) that are linked or fused thereto. Non-limiting examples of suitable photochromic groups includes those photochromic groups set forth above in detail. For example and without limitation, the photochromic group PC according to various non-limiting embodiments disclosed herein can be chosen from those photochromic pyrans, photochromic oxazines, and photochromic fulgides previously discussed. According to one specific non-limiting embodiment, PC is a photochromic pyran chosen from benzopyrans, naphthopyrans, phenanthropyrans, quinolinopyrans, fluoroanthenopyrans, and spiropyrans. According to another non-limiting embodiment, PC is a naphthopyran chosen from naphtho[1,2-b]pyrans, a naphtho[2,1-b]pyrans, indenonaphthopyrans, and heterocyclic-fused naphthopyrans. According to still another non-limiting embodiment, PC is an indenonaphthopyran.

As previously discussed, prior attempts to limit migration of photochromic materials in polymeric materials have generally involved bonding the photochromic materials to the polymeric materials with short organic segments. However, bonding photochromic materials in this manner can result in deterioration in the photochromic performance of the materials. Further, depending upon the photochromic material involved, the placement of the organic segments on the photochromic material can be limited to locations distant from the active portion of the photochromic material.

In contrast, inventors have observed that the photochromic materials according to various non-limiting embodiments disclosed herein can have good photochromic performance, even when the group S' is located near the active portion of the photochromic material. Further, according to various non-limiting embodiments disclosed herein, each PC can have more than one group S' (i.e., n can range from 1 to 8).

For example, according to one specific non-limiting embodiment, n is 4 and the photochromic material can have four S' groups, for example, as shown below:

Formula 3

According to another specific non-limiting embodiment, n is 2 and the photochromic material can have two S' groups, for example, as shown below:

Formula 4

Although not limiting herein, one specific non-limiting example of a photochromic material according to various non-limiting embodiments disclosed herein and having two S' groups, is set forth below in Example 5.

According to still another specific non-limiting embodiment, n is 1 and the photochromic material can have 1 S' group, for example, as shown below:

Formula 5

Although not limiting herein, non-limiting examples of various photochromic materials according to various non-limiting embodiments disclosed herein and having one S' group are set forth below in the Examples.

Figure 7A:
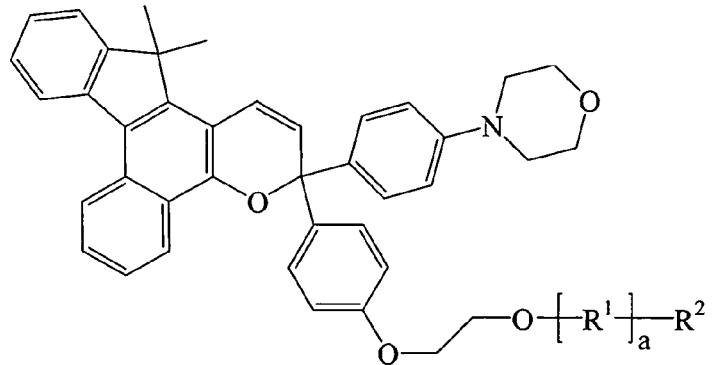

As discussed above, according to various non-limiting embodiments disclosed herein, L can be a linking group independently chosen for each occurrence from —O—, —N—, and —S—, or L can comprise a linear or branched organic bridging group comprising at least one linking group that is independently chosen for each occurrence from —O—, —N—, and —S—. As used herein the term "linking group" refers to a group forming at least one covalent bond to an $R^1$ group. As previously discussed, as used herein the term "linked" means covalently bonded. For example, although not limiting herein, as schematically depicted in FIG. 7(a), L comprises an organic bridging group having a single, linking —O— group linked to an $R^1$ group.

Figure 7B:
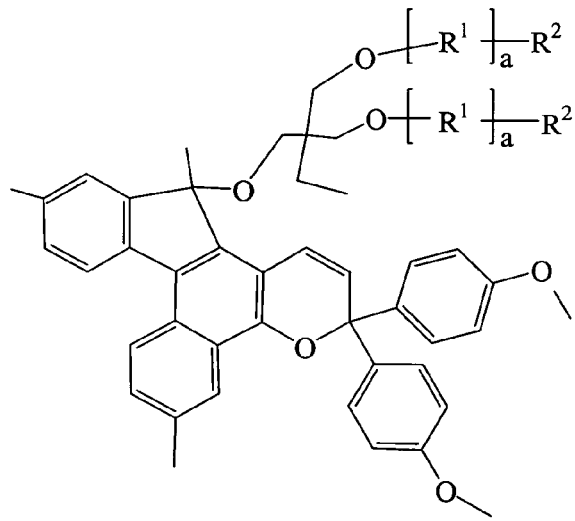
Figure 7C:
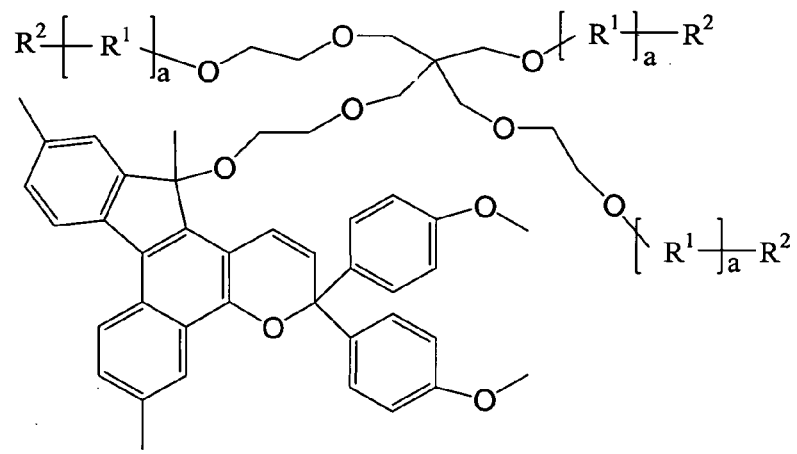

Further, as indicated above, L can comprise a linear or branched organic bridging group comprising more than one linking group. For example, and as schematically depicted in FIG. 7(b), one non-limiting embodiment disclosed herein provides a photochromic material represented by Formulae 1 and 2 above, wherein b is 2, and L is a linear or branched organic bridging group comprising two linking groups. More specifically, and without limitation herein, as depicted in FIG. 7(b), L can comprise an organic bridging group having two linking —O— groups, each of which is linked to an $R^1$ group. Further, as schematically depicted in FIG. 7(c), b is 3, and L is a branched organic bridging group having three linking —O— groups, each of which is linked to an $R^1$ group. According to still other non-limiting embodiments, the L group can be a bridging group comprising more than 3 linking groups. For example, while not limiting herein, as discussed above, b can range from 1 to 20, and L can be an organic bridging group comprising from 1 to 20 linking groups. According to other non-limiting embodiments, b can range from 1 to 16, from 1 to 10, or from 1 to 3.

According to various non-limiting embodiments disclosed herein, wherein L is a linear or branched organic bridging group comprising at least one linking group, L can be chosen from: C1-C10 alkyloxy, C1-C10 alkylamino, C1-C10 alkylthio, C2-C20 beta-oxypoly(ethoxy), C3-C30 beta-oxypoly(propoxy), C4-C40 beta-oxypoly(butoxy), C2-C20 beta-aminopoly(ethoxy), C3-C30 beta-aminopoly(propoxy), C4-C40 beta-aminopoly(butoxy), C2-C20 beta-thiopoly(ethoxy), C3-C30 beta-thiopoly(propoxy), C4-C40 beta-thiopoly(butoxy), aryl C1-C10 alkyloxy, aryl C1-C10 alkylamino, aryl C1-C10 alkylthio, aryl C2-C20 beta-oxypoly(ethoxy), aryl C3-C30 beta-oxypoly(propoxy), aryl C4-C40 beta-oxypoly(butoxy), aryl C2-C20 beta-aminopoly(ethoxy), aryl C3-C30 beta-aminopoly(propoxy), aryl C4-C40 beta-aminopoly(butoxy), aryl C2-C20 beta-thiopoly(ethoxy), aryl C3-C30 beta-thiopoly(propoxy), aryl C4-C40 beta-thiopoly(butoxy), heterocyclic C1-C10 alkyloxy, heterocyclic C1-C10 alkylamino, heterocyclic C1-C10 alkylthio, heterocyclic C2-C20 beta-oxypoly(ethoxy), heterocyclic C3-C30 beta-oxypoly(propoxy), heterocyclic C4-C40 beta-oxypoly(butoxy), heterocyclic C2-C20 beta-aminopoly(ethoxy), heterocyclic C3-C30 beta-aminopoly(propoxy), heterocyclic C4-C40 beta-aminopoly(butoxy), heterocyclic C2-C20 beta-thiopoly(ethoxy), heterocyclic C3-C30 beta-thiopoly(propoxy), heterocyclic C4-C40 beta-thiopoly(butoxy), and combinations thereof.

As used herein the term "heterocyclic" means a compound having a ring of atoms, wherein at least one atom forming the ring is different from the other atoms forming the ring. Non-limiting examples of suitable heterocyclic groups include: azaindolyl, dibenzofuro, dibenzothieno, benzofuro, benzothieno, thieno, furo, dioxano, dioxolano, carbazolyl, benzoxazolyl, benzimidazolyl, benzthiazolyl, imidazolyl, indazolyl, isobenzoxazolyl, isooxazolyl, isoindolyl, isooxazolyl, isoquinolinyl, isothiazolyl, morpholino, oxadiazolyl, oxathiazolyl, piperidino, purinyl, phenazinyl, piperazino, pyrazinyl, pyrazolyl, pyridyl, pyrimidinyl, pyrrolidinyl, quinolinyl, isoquinolinyl, thiazolyl, triazinyl, thiomorpholino, thiadiazolyl, tetrahydroquinolinyl, and tetrahydroisoquinolinyl.

Non-limiting examples of aryl group is chosen from phenyl and naphthyl.

Specific non-limiting examples of suitable bridging groups comprising at least one linking group from which L can be chosen, include those organic groups comprising at least one functional group adapted to initiate ring-opening of at least one cyclic monomer set forth in Table 1 above after reaction of the functional group with a cyclic monomer. For example, although not limiting herein, L can comprise the organic group comprising the hydroxy or alcohol group shown in structure 1.4 (i.e., the 4-(2-hydroxyethoxy)phenyl group) after reaction of the functional group with a ring-opening cyclic monomer. That is, L can be 4-(2-oxoethoxyphenyl) group.

As discussed above, $R^1$ is a ring-opened cyclic monomer. Further, as previously discussed, as used herein the term "ring-opened cyclic monomer" means the acyclic form of a ring-opening cyclic monomer. Non-limiting examples of suitable ring-opening cyclic monomers are set forth above in detail. For example, according to one non-limiting embodiment, $R^1$ can be chosen from a ring-opened cyclic ester monomer, a ring-opened cyclic carbonate monomer, a ring-opened cyclic ether monomer, and a ring-opened cyclic siloxane monomer. According to another non-limiting embodiment, $R^1$ can be chosen from a ring-opened cyclic ester monomer and a ring-opened cyclic carbonate monomer. According to still another non-limiting embodiment, $R^1$ can be chosen from a ring-opened ε-caprolactone monomer and a ring-opened δ-valerolactone monomer.

Further, as indicated above, according to various non-limiting embodiments disclosed herein, the photochromic materials can have from 1 to 8 S' groups, and each S' group can have one $R^1$ group or a plurality of $R^1$ groups. Thus, according to various non-limiting embodiments disclosed herein, 'a' in Formula 2 can be independently chosen for each occurrence 1 to 500. According to other non-limiting embodiments, 'a' can range from 1 to 100. According to still other non-limiting embodiments, 'a' can range from 1 to 60. According to still other non-limiting embodiments, 'a' can range from 20 to 60.

As previously discussed, according to various non-limiting embodiments disclosed herein, the photochromic material can comprise a polymeric chain segment comprising a plurality of ring-opened cyclic monomers. According various non-limiting embodiments, the polymeric chain segment is desirably a flexible chain segment having a plurality of $R^1$ groups that allows for flexible bonding of the photochromic material to a polymeric material. According to other non-limiting embodiments, the polymeric chain segment is a flexible chain segment having from 10 to 100 or from 20 to 60 $R^1$ groups that allows for flexible bonding of the photochromic material to a polymeric material. Further and as discussed in more detail below, according to these non-limiting embodiments, each $R^1$ groups can be the same or different from the remaining $R^1$ groups (i.e., the polymeric chain segment can be a homopolymer or copolymer). While not intending to be bound to any particular theory, it is contemplated that the flexible segments according to various non-limiting embodiments disclosed herein can be beneficial in allowing a photochromic material to be bonded to a polymeric material without impeding the photochromic performance of the material.

When S' comprises a plurality of $R^1$ groups, the $R^1$ groups can be linked together to form a chain segment. Moreover, each $R^1$ group in the plurality of $R^1$ groups can be the same as or different from the remaining $R^1$ groups. Thus, for example, according to one non-limiting embodiment wherein S' has a plurality of $R^1$ groups, each $R^1$ group can be independently chosen from ring-opened ε-caprolactone monomers and ring-opened δ-valerolactone monomers. According to another non-limiting embodiment wherein S' comprises a plurality of $R^1$ groups, at least one $R^1$ can be a ring-opened ε-caprolactone monomer and at least one $R^1$ can be a ring-opened δ-valerolactone monomer. Thus, according to this non-limiting embodiment S' comprises a copolymeric chain segment. For example, one non-limiting example of a photochromic material according to various non-limiting embodiments disclosed herein, wherein the photochromic material comprises two S' groups, each of which comprises a plurality of $R^1$ groups which together form a copolymeric chain segment, is set forth in Example 5 below.

Further, according to various non-limiting embodiments disclosed herein, for each S', each $-[R^1]_a-$ segment can have a number average molecular weight ranging from 100 to 22,000 grams per mole ("g/mol."). According to other non-limiting embodiments, for each S', each $-[R^1]_a-$ segment can have a number average molecular weight ranging from 2000 to 6000 g/mol. According to still other non-limiting embodiments, for each S', each $-[R^1]_a-$ segment can have a number average molecular weight ranging from 100 to 500 g/mol.

As discussed above, the group $R^2$ is independently chosen for each occurrence from hydrogen and an organic material comprising the residue of at least one reactive group. As previously discussed, as used herein the term "residue of a reactive group" means that which remains after a reactive group has been reacted. Further, although not limiting herein, according to various non-limiting embodiments wherein $R^2$ is an organic material comprising the residue of at least one reactive group, the residue of the at least one reactive group can be chosen from an acrylate an alkyl, an alkyl-phosphonate, an alkyldialkoxysilyl, an alkyloxydialkylsilyl, an allyl carbonate, an amide, an amine, an anhydride, an aryl, an aziridine, a carboxylic acid, a chloroformate, a cycloaliphatic epoxide, an isocyanate, an isothiocyanate, an epoxide, an ester, a halogen, a hydroxyl group, a methacrylate, a propenyl ether, a residue of a ring-opening cyclic monomer, a trialkoxysilyl, a thiirane, a thiol, a vinyl carbonate, a vinyl ether, a vinylbenzyl ether, and combinations thereof. According to still other non-limiting embodiments, $R^2$ can be an organic material comprising the residue of at least one reactive group, wherein the residue of the at least one reactive group is chosen from an acrylate, an alkyl, an alkyldialkoxysilyl, an alkyloxydialkylsilyl, an allyl carbonate, an amide, an amine, an anhydride, an aryl, a carboxylic acid, a chloroformate, a cycloaliphatic epoxide, an isocyanate, an isothiocyanate, an epoxide, a halogen, a hydroxyl group, a methacrylate, a thiol, a propenyl ether, a residue of a ring-opening cyclic monomer, a trialkoxysilyl, a vinyl carbonate, a vinyl ether, a vinylbenzyl ether, and combinations thereof. Further, as previously discussed, according to various non-limiting embodiments disclosed herein, the organic material comprising the residue of at least one reactive group can further comprise at least one unreacted reactive group.

As previously discussed, the photochromic materials according to various non-limiting embodiments disclosed herein can comprise an organic material comprising the residue of at least one reactive group that is not intended for further bonding or reaction. Thus, according to various non-limiting embodiments disclosed herein, $R^2$ can be an organic material comprising the residue of at least one reactive group that is not intended for further bonding or reaction. For example, and without limitation, the organic material comprising the residue of at least one reactive group can be capped with a non-reactive functionality. Although not limiting herein, for example, as shown in photochromic material 444 in FIG. 4, $R^2$ can be an organic material comprising the residue of an isocyanate group that is not intended for further bonding or reaction.

Alternatively, according to various non-limiting embodiments disclosed herein, $R^2$ can be an organic material comprising the residue of at least one reactive group that is intended for further bonding or reaction. For example, although not limiting herein, $R^2$ can be an organic material comprising the residue of an isocyanate group and an unreactive isocyanate group, such as shown in photochromic material 554 in FIG. 5; or as shown in photochromic material 664 in FIG. 6, $R^2$ can be an organic material comprising the residue of a ring-opening cyclic monomer which further comprises a reactive halogen group.

Other non-limiting embodiments disclosed herein provide a photochromic material represented by:

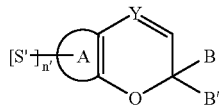

Formula 6 wherein Y can be chosen from carbon or nitrogen; the group A can be chosen from naphtho, benzo, phenanthro, fluorantheno, antheno, quinolino, thieno, furo, indolo, indolino, indeno, benzofuro, benzothieno, thiopheno, indenonaphtho, heterocyclic-fused naphtho, and heterocyclic-fused benzo; the group S' is as set forth above; and n' is an integer chosen from 0 to 8, provided that if n' is 0, then at least one of B or B' comprises the group S' (set forth above).

With continued reference to Formula 6, B and B' can be independently chosen from: (1) the group S'(which is set forth above); (2) mono-$R^{17}$-substituted phenyl wherein $R^{17}$ is represented by one of: -G[$(OC_2H_4)_q(OC_3H_6)_r(OC_4H_8)_s$]J and —[$(OC_2H_4)_q(OC_3H_6)_r(OC_4H_8)$S]J, wherein -G is chosen from —C(O)— and —CH$_2$—, J is chosen from C1-C12 alkoxy and a polymerizable group, q, r, and s are each a number between 0 and 50, and the sum of q, r and s is between 2 and 50; (3) an unsubstituted, mono-, di-, or tri-substituted aryl group; (4) 9-julolidinyl, an unsubstituted, mono- or di-substituted heteroaromatic group chosen from pyridyl furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, each of the aryl and heteroaromatic substituents in (3) and (4) are independently chosen from: (i) hydroxy, (ii) the group —C(O)$R^8$, wherein $R^{18}$ is chosen from —$OR^{19}$, —N($R^{20}$)$R^{21}$, piperidino and morpholino, wherein $R^{19}$ is chosen from allyl, C1-C6 alkyl, phenyl, mono(C1-C6)alkyl substituted phenyl, mono(C1-C6)alkoxy substituted phenyl, phenyl(C1-C3)alkyl, mono(C1-C6)alkyl substituted phenyl(C1-C3)alkyl, mono(C1-C6)alkoxy substituted phenyl(C1-C3)alkyl, C1-C6 alkoxy(C2-C4)alkyl and C1-C6 haloalkyl; $R^{20}$ and $R^{21}$ are each chosen from C1-C6 alkyl, C5-C7 cycloalkyl, phenyl, mono-substituted phenyl and di-substituted phenyl, the phenyl substituents being chosen from C1-C6 alkyl and C1-C6 alkoxy, and said halo substituent being chosen from chloro and fluoro; (iii) aryl, mono(C1-C12)alkoxyaryl, di(C1-C12)alkoxyaryl, mono(C1-C12)alkylaryl, di(C1-C12)alkylaryl, haloaryl, C3-C7 cycloalkylaryl, C3-C7 cycloalkyl, C3-C7 cycloalkyloxy, C3-C7 cycloalkyloxy(C1-C12)alkyl, C3-C7 cycloalkyloxy(C1-C12)alkoxy, aryl(C1-C12)alkyl, aryl(C1-C12)alkoxy, aryloxy, aryloxy(C1-C12)alkyl, aryloxy(C1-C12)alkoxy, mono- or di(C1-C12)alkylaryl(C1-C12)alkyl, mono- or di-(C1-C12)alkoxyaryl(C1-C12)alkyl, mono- or di-(C1-C12)alkylaryl(C1-C112)alkoxy, mono- or di-(C1-C12)alkoxyaryl(C1-C12)alkoxy, amino, mono(C1-C12)alkylamino, di(C1-C12)alkylamino, diarylamino, piperazino, N—(C1-C12)alkylpiperazino, N-arylpiperazino, aziridino, indolino, piperidino, morpholino, thiomorpholino, tetrahydroquinolino, tetrahydroisoquinolino, pyrrolidyl, C1-C12 alkyl, C1-C12 haloalkyl, C1-C12 alkoxy, mono(C1-C12)alkoxy(C1-C12)alkyl, acryloxy, methacryloxy, and halogen; (5) an unsubstituted or mono-substituted group chosen from pyrazolyl, imidazolyl, pyrazolinyl, imidazolinyl, pyrrolinyl, phenothiazinyl, phenoxazinyl, phenazinyl and acridinyl, each of said substituents being independently chosen from C1-C12 alkyl, C1-C12 alkoxy, phenyl, and halogen;

(6) a monosubstituted phenyl, said phenyl having a substituent located at the para position, wherein the substituent is chosen from —(CH$_2$)$_t$— and —O—(CH$_2$)$_t$—, wherein t is an integer chosen from 1, 2, 3, 4, 5 and 6, the substituent being connected to an aryl group on another photochromic material; (7) a group represented by one of the following:

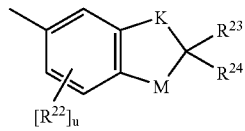

Formula 7

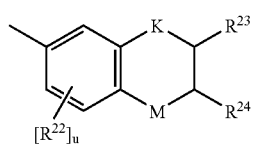

Formula 8 wherein K is independently chosen in each formula from methylene and oxygen, and M is independently chosen in each formula from oxygen and substituted nitrogen, provided that when M is substituted nitrogen, K is methylene; the substituted nitrogen substituents being chosen from hydrogen, C1-C12 alkyl, and C1-C12 acyl; each $R^{22}$ being independently chosen for each occurrence in each formula from C1-C12 alkyl, C1-C12 alkoxy, hydroxy, and halogen; $R^{23}$ and $R^{24}$ each being independently chosen in each formula from hydrogen and C1-C12 alkyl; and u is an integer chosen from 0, 1 and 2; and (8) C1-C12 alkyl, C1-C12 haloalkyl, C1-C12 alkoxy(C1-C12)alkyl, C3-C7 cycloalkyl, mono(C1-C12) alkoxy (C3-C7)cycloalkyl, mono(C1-C12)alkyl(C3-C7)-cycloalkyl, halo(C3-C7)cycloalkyl, and C4-C12 bicycloalkyl, provided that both B and B' are not chosen from (8); and (9) a group represented by the following graphic Formula 9:

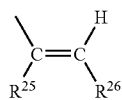

Formula 9 wherein $R^{25}$ is chosen from hydrogen and C1-C12 alkyl, and $R^{26}$ is chosen from an unsubstituted, mono-, or di-substituted group chosen from naphthyl, phenyl, furanyl, and thienyl, wherein the substituents are independently chosen from C1-C12 alkyl, C1-C12 alkoxy, and halogen.

Alternatively, according to various non-limiting embodiments disclosed herein, B and B' can together form a fluoren-9-ylidene, mono-, or di-substituted fluoren-9-ylidene or a spirocyclic group chosen from saturated C3-C12 spiro-monocyclic hydrocarbon rings, saturated C7-C12 spiro-bicyclic hydrocarbon rings, or saturated C7-C12 spiro-tricyclic hydrocarbon rings, provided that said spirocyclic group is not norbornylidene or bicyclo[3.3.1]9-nonylidene, each of said fluoren-9-ylidene substituents being independently chosen from C1-C12 alkyl, C1-C12 alkoxy, halogen, and the group S' (set forth above).

As previously discussed, photochromic materials having a relative short, organic chain segments attached thereto, and which can be polymerized into a polymeric material, have been described. However, for certain photochromic materials, the placement of such organic chain segments on the photochromic material can be limited to locations that are distant from the active portion of the photochromic material. If the chain segments are placed too close to the active portion of the photochromic material, the ability of the photochromic material to transform can be impeded, thereby deteriorating the photochromic performance of the material. However, the inventors have observed that the S' groups according to various non-limiting embodiments disclosed herein generally do not impede the photochromic performance, even when placed close to the active portion of a photochromic material. Further, as discussed in more detail below, the photochromic performance of the photochromic materials according to various non-limiting embodiments disclosed herein can be better than that of similar photochromic materials which do not contain the group S'.

Thus, according to various non-limiting embodiments disclosed herein, wherein Y in Formula 6 is carbon and A is indenonaphtho, the photochromic material is an indenonaphthopyran represented by:

Formula 10

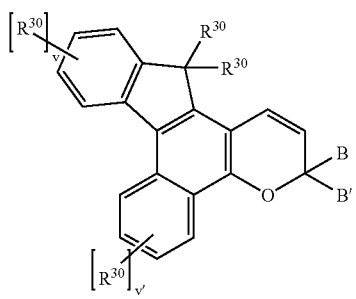

wherein v and v' are integers chosen from 0 to the total number of available positions, provided that at least one of an $R^{30}$ group, B and B' comprises the group S'. For example, although not limiting herein, according to one non-limiting embodiment the photochromic material is an indenonaphthopyran represented by:

Formula 11

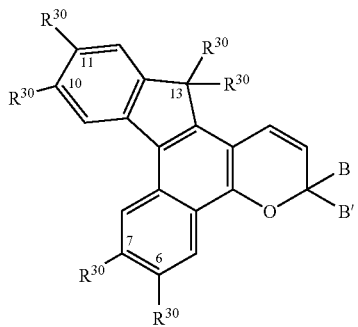

and at least one of an $R^{30}$ group, B and B' comprises the group S'. Other non-limiting examples of groups from which the $R^{30}$ groups in the 13 position can be chosen are set forth in U.S. Pat. No. 6,555,028 at col. 9 lines 4 to 42, which disclosure is hereby specifically incorporated by reference herein. Other non-limiting examples of groups from which the $R^{30}$ groups in the 6, 7, 10, and 11 positions can be chosen are set forth in U.S. Pat. No. 6,555,028 at col. 8 line 62 to col. 9 line 4, which disclosure is hereby specifically incorporated by reference herein. Other non-limiting examples of groups from which B and B' can be chosen are set forth above.

According other non-limiting embodiments disclosed herein, wherein Y in Formula 6 is carbon and A is naphtho derived from α-naphthol, the photochromic material is a 2H-naphtho[1,2-b]pyran represented by:

Formula 12

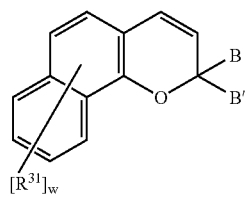

wherein w is an integer chosen from 0 to the total number of available positions, provided at least one of an $R^{31}$ group, B and B' comprises the group S'. For example, although not limiting herein, according to one non-limiting embodiment the photochromic material is a 2H-naphtho[1,2-b]pyran represented by:

Formula 13

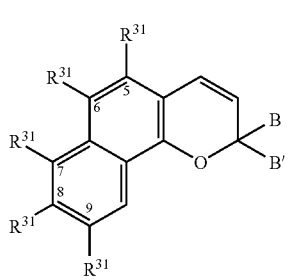

and at least one of an $R^{31}$ group, B and B' comprises the group S'. Other non-limiting examples of groups from which the $R^{31}$ groups in the 7, 8, and 9 positions can be chosen are set forth in U.S. Pat. No. 6,555,028 at col. 8, line 62 to col. 9, line 4, which disclosure is hereby specifically incorporated by reference herein. Other non-limiting examples of groups from which the $R^{31}$ groups in the 5 position can be chosen are set forth in U.S. Pat. No. 6,555,028 at col. 8, lines 40 to 51, which disclosure is hereby specifically incorporated by reference herein. Other non-limiting examples of groups from which the $R^{31}$ groups in the 6 position can be chosen are set forth in U.S. Pat. No. 6,555,028 at col. 8, lines 52 to 61, which disclosure is hereby specifically incorporated by reference herein. Other non-limiting examples of groups from which B and B' can be chosen are set forth above.

According to still other non-limiting embodiments disclosed herein, wherein Y in Formula 6 is carbon and A is naphtho derived from β-naphthol, the photochromic material is a 3H-naphtho[2,1-b]pyran represented by:

Formula 14

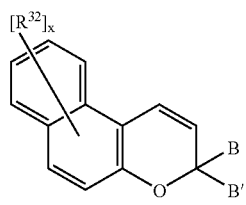

wherein x is an integer chosen from 0 to the total number of available positions, provided that at least one of an $R^{32}$ group, B and B' comprises the group S'. For example, although not limiting herein, in one non-limiting embodiment, the photochromic material is a 3H-naphtho[2,1-b]pyran represented by:

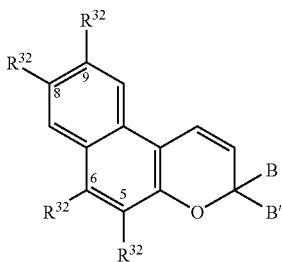

Formula 15 and at least one of an $R^{32}$ group, B and B' comprises the group S'. Other non-limiting examples of groups from which the $R^{32}$ groups in the 5 and 6 positions can be chosen are set forth in U.S. Pat. No. 6,555,028 at col. 8, line 62 to col. 9, line 4, which disclosure is hereby specifically incorporated by reference herein. Other non-limiting examples of groups from which the $R^{32}$ group in the 9 position can be chosen are set forth in U.S. Pat. No. 6,555,028 at col. 8, lines 40 to 51, which disclosure is hereby specifically incorporated by reference herein. Other non-limiting examples of groups from which the $R^{32}$ group in the 8 position can be chosen are set forth in U.S. Pat. No. 6,555,028 at col. 8, lines 52 to 61, which disclosure is hereby specifically incorporated by reference herein.

Other non-limiting embodiments disclosed herein provide a photochromic material represented by:

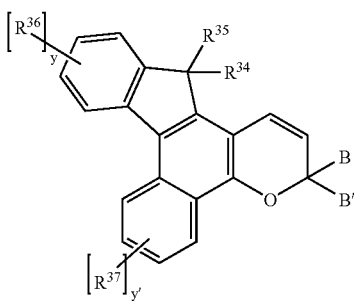

Formula 16 wherein $R^{34}$ and $R^{35}$ can be independently chosen from the group S' (as set forth above), hydrogen, hydroxy, C1-C6 alkyl, C3-C7 cycloalkyl, allyl, phenyl, mono-substituted phenyl, benzyl, mono-substituted benzyl, chloro, fluoro, the group —C(O)$R^{40}$, wherein $R^{40}$ is hydroxy, C1-C6 alkyl, C1-C6 alkoxy, phenyl, mono-substituted phenyl, amino, mono(C1-C6)alkylamino, or di(C1-C6)alkylamino.

Alternatively, $R^{34}$ and $R^{35}$ can each be the group —O$R^{41}$, wherein $R^{41}$ is C1-C6 alkyl, phenyl(C1-C3)alkyl, mono(C1-C6)alkyl substituted phenyl(C1-C3)alkyl, mono(C1-C6) alkoxy substituted phenyl(C1-C3)alkyl, C1-C6 alkoxy(C2-C4)alkyl, C3-C7 cycloalkyl, mono(C1-C4)alkyl substituted C3-C7 cycloalkyl, C1-C6 chloroalkyl, C1-C6 fluoroalkyl, allyl, the group —CH($R^{42}$)$R^{43}$, wherein $R^{42}$ is hydrogen or C1-C3 alkyl and $R^{43}$ is CN, CF$_3$, or COO$R^{44}$ and $R^{44}$ is hydrogen or C1-C3 alkyl; or $R^{41}$ is the group —C(O)$R^{45}$, wherein $R^{45}$ is hydrogen, C1-C6 alkyl, C1-C6 alkoxy, the unsubstituted, mono- or di-substituted aryl groups phenyl or naphthyl, phenoxy, mono- or di-(C1-C6)alkyl substituted phenoxy, mono- or di-(C1-C6)alkoxy substituted phenoxy, amino, mono(C1-C6)alkylamino, di(C1-C6)alkylamino, phenylamino, mono- or di-(C1-C6)alkyl substituted phenylamino, or mono- or di-(C1-C6)alkoxy substituted phenylamino, each of said phenyl, benzyl and aryl group substituents being C1-C6 alkyl or C1-C6 alkoxy.

Further, $R^{34}$ and $R^{35}$ together can form an oxo group, a spiro-carbocyclic ring containing 3 to 6 carbon atoms or a spiro-heterocyclic group containing 1 or 2 oxygen atoms and 3 to 6 carbon atoms including the spirocarbon atom, said spiro-carbocyclic and spiro-heterocyclic groups being annellated with 0, 1 or 2 benzene rings.

With continued reference to Formula 16 above, each $R^{36}$ and $R^{37}$ is independently chosen from the group S' (as set forth above), hydrogen, C1-C6 alkyl, C3-C7 cycloalkyl, phenyl, mono-substituted phenyl, di-substituted phenyl and the groups —O$R^{50}$ and —OC(O)$R^{50}$, wherein $R^{50}$ is C1-C6 alkyl, phenyl(C1-C3)-alkyl, mono(C1-C6)alkyl substituted phenyl(C1-C3)alkyl, mono(C1-C6)alkoxy substituted phenyl(C1-C3)alkyl, C1-C6 alkoxy(C2-C4)alkyl, C3-C7 cycloalkyl or mono(C1-C4)alkyl substituted C3-C7 cycloalkyl, and the phenyl substituent being C1-C6 alkyl or C1-C6 alkoxy. The groups B and B' are as set forth above with respect to Formula 6. Further, in Formula 16, y and y' are each integers that are independently from 0 to the total number of available positions, provided that the photochromic material represented by Formula 16 comprises at least one group S'.

Other non-limiting embodiments disclosed herein contemplate methods of making the aforementioned photochromic materials. For example, one non-limiting embodiment provides a method of making a photochromic material, the method comprising initiating ring-opening of at least one ring-opening one cyclic monomer chosen from a cyclic ester, a cyclic carbonate, a cyclic ether, and a cyclic siloxane, with a photochromic initiator comprising at least one functional group adapted to initiate ring-opening of the at least one ring-opening cyclic monomer. Suitable non-limiting examples of functional group that can be used to initiate ring-opening (and ring-opening polymerization) of various ring-opening cyclic monomers include alcohols, amines, carboxylic acids, silanols, thiols, and combinations, salts and complexes thereof. While not limiting herein, according to one non-limiting embodiment, the at least one functional group can be chosen from a primary alcohol, a secondary alcohol, or a salt or complex thereof.

As previously discussed, by initiating ring-opening of at least one cyclic monomer with a photochromic initiator comprising at least one suitable functional group, it is possible to form a photochromic material comprising the residue of at least one ring-opening cyclic monomer or at least one ring-opened cyclic monomer. Further, as previously discussed, once the photochromic initiator initiates ring-opening of at least one cyclic monomer, the resultant photochromic material comprising the residue of the ring-opening cyclic monomer can further initiate the ring-opening of another ring-opening monomer (i.e., the photochromic material is a photochromic initiator), etc., thereby forming a polymeric chain comprised of the residue of a plurality of ring-opening cyclic monomers. Further, although not required, initiation of the ring-opening reaction can occur in the presence of at least one catalyst. Non-limiting examples of suitable catalysts include aluminum isopropoxide, triethyl aluminum, tin(II)2-ethylhexanoate, trifluoro acetic acid, enzymes, potassium or an appropriate salt thereof, and trifluoromethanesulfonic anhydride. The choice of appropriate catalyst will be readily appreciated by those skilled in the art.

The photochromic materials according to various non-limiting embodiments disclosed herein can be incorporated into polymeric materials, which can be used, for example and without limitation, to form articles of manufacture, such as optical elements, and coatings. Further, it is contemplated that the photochromic materials according to various non-limiting embodiments disclosed herein may each be used alone, in combination with other photochromic materials according to various non-limiting embodiments disclosed herein, or in combination with one or more other appropriate complementary conventional photochromic materials. For example, the photochromic materials according to various non-limiting embodiments disclosed herein can be used in conjunction with one or more other conventional photochromic materials having at least one activated absorption maxima within the range of 300 to 1000 nanometers. The complementary conventional photochromic materials may include other polymerizable or compatabilized photochromic materials, such as those disclosed in U.S. Pat. Nos. 4,719,296; 5,166,345; 5,236,958; 5,252,742; 5,359,085; 5,488,119; and 6,113,814 (at col. 2, line 39 to col. 8 line 416), and 6,555,028 (at col. 2, line 65 to col. 12 line 56), which disclosures are hereby specifically incorporated by reference herein.

Further examples of complementary conventional photochromic materials include other naphthopyrans and indenonaphthopyrans, benzopyrans and oxazines, substituted 2H-phenanthro[4,3-b]pyran and 3H-phenanthro[1,2-b]pyrans, benzopyrans having substituents at the 2-position of the pyran ring and mixtures of such photochromic materials, such as those photochromic materials are described in U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,981; 5,274,132; 5,384,077; 5,405,958; 5,429,774; 5,458,814; 5,466,398; 5,514,817; 5,552,090; 5,552,091; 5,565,147; 5,573,712; 5,578,252; 5,637,262; 5,645,767; 5,656,206; 5,658,500; 5,658,501; 5,674,432 and 5,698,141. Still other complementary photochromic materials contemplated are fulgides and fulgimides, e.g., the 3-furyl and 3-thienyl fulgides and fulgimides, which are described in U.S. Pat. No. 4,931,220 at col. 20, line 5 to col. 21, line 38.

Additionally, according to various non-limiting embodiments disclosed herein, the photochromic compositions may contain one photochromic material or a mixture of two or more photochromic materials, as desired. Mixtures of photochromic materials may be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

For example, various non-limiting embodiment disclosed herein provide a photochromic composition comprising (a) a polymeric material; and (b) at least one photochromic material in contact with at least a portion of the polymeric material, the at least one photochromic material comprising a reaction product of (1) at least one ring-opening cyclic monomer chosen from a cyclic ester and a cyclic carbonate, and (2) a photochromic initiator. As used herein the term "photochromic composition" refers at least one photochromic material in combination with at least one other material, which may or may not be a photochromic material. As used herein, the term "contact" includes both direct and indirect contact. For example, although not limiting herein, according to various non-limiting embodiments disclosed herein, the at least one photochromic material can be be in contact with at least a portion of the polymeric material by blending or bonding. As used herein, the term "blended" means that the photochromic material is intermixed with the at least a portion of the polymer material, but not bonded to the polymeric material. Further, as used herein, the term "bonded" means that the photochromic material is either directly attached to a portion of the polymeric material or indirectly attached to a portion of the polymeric material through one or more other groups.

For example, one non-limiting embodiment provides, a photochromic composition comprising (a) a polymeric material; and (b) at least one photochromic material that is blended with at least a portion of the polymeric material, the at least one photochromic material comprising a reaction product of (1) at least one ring-opening cyclic monomer chosen from a cyclic ester and a cyclic carbonate, and (2) a photochromic initiator. Another non-limiting embodiment provides, a photochromic composition comprising (a) a polymeric material; and (b) at least one photochromic material that is bonded to at least a portion of the polymeric material, the at least one photochromic material comprising a reaction product of: (1) at least one ring-opening cyclic monomer chosen from a cyclic ester and a cyclic carbonate, and (2) a photochromic initiator.

Examples of polymeric materials which may be used in conjunction with various non-limiting embodiments disclosed herein include, without limitation: polymers of bis (allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers, such as those described in U.S. Pat. No. 5,373,033; and vinylbenzene monomers, such as those described in U.S. Pat. No. 5,475,074 and styrene. Other non-limiting examples of suitable polymeric materials include polymers of polyfunctional, e.g., mono-, di- or multi-functional, acrylate and/or methacrylate monomers; poly(C1-C12 alkyl methacrylates), such as poly (methyl methacrylate); poly(oxyalkylene)dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly (α-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric materials are disclosed in the U.S. Pat. No. 5,753,146 at col. 8, line 62 to col. 10, line 34, which disclosure is hereby specifically incorporated herein by reference. Other suitable non-limiting examples of polymeric materials are those prepared from the monomers and mixtures of monomers disclosed in U.S. Pat. No. 5,962,617 at col. 2, line 9 to col. 5, line 64; and in U.S. Pat. No. 5,658,501 at col. 15, line 28 to col. 16, line 17, which disclosures are hereby specifically incorporated herein by reference. Also contemplated are copolymers of the aforementioned monomers and blends of the aforementioned polymers and copolymers with other polymers, e.g., to form interpenetrating network products.

Further, according to various non-limiting embodiments wherein transparency of the photochromic composition is desired, the polymeric material can comprise transparent polymers, copolymers and blends thereof. For example, according to various non-limiting embodiments, the polymeric material can be an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane prepolymer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, e.g., copolymers of from 80-90 percent diethylene glycol bis(allyl carbonate) and 10-20 percent vinyl acetate, particularly 80-85 percent of the bis(allyl carbonate) and 15-20 percent vinyl acetate; copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. Although not limiting herein, optically clear polymeric materials typically have a refractive index that may range from about 1.48 to about 1.75.

According to one non-limiting embodiment, the polymeric material can be an optical resins sold by PPG Industries, Inc. under the CR-designation, e.g., CR-307, CR-407, and CR-607, or a polymeric material prepared for use as hard or soft contact lenses. Methods for producing both types of contact lenses are disclosed in U.S. Pat. No. 5,166,345, at col. 11, line 52, to col. 12, line 52, which disclosure is hereby specifically incorporated by reference herein. Additional polymeric materials that can be used in accordance with various non-limiting embodiments disclosed herein, include polymeric materials used to form soft contact lenses with high moisture content described in U.S. Pat. No. 5,965,630 and extended wear contact lenses described in U.S. Pat. No. 5,965,631, both disclosures of which are incorporated herein by reference.

According to one specific non-limiting embodiment, the polymeric material is chosen from copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); and poly(silane).

According to still other non-limiting embodiments, the photochromic materials according to various non-limiting embodiments disclosed herein can be incorporated into polymeric microparticles, for example by bonding the photochromic material to a portion of the microparticles or encapsulating the photochromic material in the microparticles. For example, although not limiting herein, the photochromic materials can be bonded to the microparticles by bonding the photochromic material to at least one component of a polymerizable system comprising at least one substantially hydrophobic polymeric, pre-polymeric, or monomeric material, and at least one substantially hydrophilic polymeric, pre-polymeric, or monomeric material, wherein the components of the polymerizable system are adapted to combine and to form at least partially cross-linked photochromic polymeric microparticles. Alternatively, the photochromic material can be encapsulated in the microparticles without bonding. For example, the components of the polymerizable system can self-assemble into at least partially formed microparticles that encapsulate the photochromic material during formation.

Another non-limiting embodiment provides a photochromic composition comprising a polymeric material, and at least one photochromic material in contact with at least a portion of the polymeric material, wherein the at least one photochromic material is represented by Formula 1, which is set forth in detail above.

As previously discussed, it has been observed by the inventors that when the photochromic materials according to various non-limiting embodiments disclosed herein are incorporated, with or without bonding, into polymeric materials, such as those described above, the photochromic performance of the materials, i.e., the activation or coloration and fade rates of the materials, can be equivalent to or better than the photochromic performance of corresponding photochromic materials. For example, although not limiting herein, photochromic materials according to various non-limiting embodiments disclosed herein (such as those represented by Formula 1), can have equivalent or better photochromic performance when incorporated into a polymeric material than a corresponding photochromic material represented by PC, but lacking a group S'. Further, the photochromic materials according to various non-limiting embodiments disclosed herein can display equivalent or better photochromic performance than such corresponding photochromic materials, even when bonded to the polymeric material and corresponding photochromic material is not. As previously discussed, prior attempts to bond photochromic materials to a polymeric material to prevent migration of the photochromic material have generally resulted in deterioration of photochromic performance.

Further, it has been observed that photochromic materials represented by PC-[S']$_n$ according to various non-limiting embodiments disclosed herein, when bonded to a polymeric material, can have equivalent migration and improved photochromic performance as compared to corresponding photochromic materials having a short, organic chain segment (such as a photochromic material represented by PC-L-H), but which lack an —[R$^1$]$_a$— segment, when bonded to the same polymeric material.

For example, one non-limiting embodiment disclosed herein provides a photochromic composition comprising: (a) a polymeric material; and (b) at least one photochromic material in contact with at least a portion of the polymeric material, the at least one photochromic material comprising a reaction product of (1) at least one ring-opening cyclic monomer chosen from a cyclic ester and a cyclic carbonate, and (2) a photochromic initiator, wherein a fade rate of the at least one photochromic material when bonded to the polymeric material is equal to or faster than a fade rate of a corresponding photochromic material that lacks a residue of a cyclic monomer when bonded to the polymeric material. According to other non-limiting embodiments, the T½ value of the at least one photochromic material when bonded to the polymeric material is no greater than a T½ value of a corresponding photochromic material that lacks a residue of a cyclic monomer when bonded to the polymeric material. According to still other non-limiting embodiments, the T½ value of the at least one photochromic material when bonded to the polymeric material is less than a T½ value of a corresponding photochromic material that lacks a residue of a cyclic monomer when bonded to the polymeric material. As discussed in the Examples, as used herein, the term "T½ value" refers to the time interval in seconds for the ΔOD of the activated form of the photochromic material in a photochromic composition to reach one half the fifteen-minute ΔOD at 73.4° F. (23° C.), after removal of the activating light source Another non-limiting embodiment provides a photochromic composition comprising a polymeric material, and at least one photochromic material bonded to at least a portion of the polymeric material, wherein the at least one photochromic material is represented by PC-[S']$_n$, which is set forth in detail above, and wherein the fade rate of the at least one photochromic material represented by PC-[S']$_n$ when bonded to the polymeric material is equal to or faster than the fade rate of a corresponding photochromic material represented by PC (i.e., without S') in contact with the polymeric material or the fade rate a corresponding photochromic material represented by PC-L-H (i.e., without the residue of at least one cyclic monomer) when bonded to the polymeric material, wherein PC and L are as set forth above. According to other non-limiting embodiments, the T½ value of the at least one photochromic material represented by PC-[S']$_n$ when bonded to the polymeric material is no greater than a T½ value of the photochromic material represented by PC in contact with the polymeric material or a T½ value of the photochromic material represented by PC-L-H when bonded to the polymeric material. According to still other non-limiting embodiments, the T½ value of the at least one photochromic material represented by PC-[S']$_n$ when bonded to the polymeric material is less than a T½ value of the photochromic material represented by PC in contact with the polymeric material or a T½ value of the photochromic material represented by PC-L-H when bonded to the polymeric material.

Another non-limiting embodiment provides a photochromic composition comprising (a) a polymeric material; and (b) at least one photochromic material bonded to at least a portion of the polymeric material, the at least one photochromic material comprising (1) a photochromic group, and (2) at least one segment comprising the residue of a plurality of ring-opening cyclic monomers bonded to the photochromic group, the ring-opening cyclic monomers being chosen from cyclic esters, cyclic carbonates, cyclic ethers, cyclic siloxanes, and combinations thereof, wherein the at least one segment has a number average molecular weight of at least 1000 g/mol., and wherein the photochromic material when bonded to the polymeric material has a T½ value that is no greater than a T½ value of a corresponding photochromic material that lacks a segment comprising the residue of a plurality of ring-opening cyclic monomers.

As previously discussed, the present invention further contemplates optical elements made using the photochromic materials and compositions according to various non-limiting embodiments disclosed herein. As used herein the term "optical" means pertaining to or associated with light and/or vision.

The optical elements according to various non-limiting embodiments disclosed herein can be chosen from ophthalmic elements, display elements, windows, mirrors, and active and passive liquid crystal cell elements. As used herein the term "ophthalmic" means pertaining to or associated with the eye and vision. Non-limiting examples of ophthalmic elements include corrective and non-corrective lenses, including single vision or multi-vision lenses, which may be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors. As used herein the term "display" means the visible or machine-readable representation of information in words, numbers, symbols, designs or drawings. Non-limiting examples of display elements include screens, monitors, and security elements, such as security marks. As used herein the term "window" means an aperture adapted to permit the transmission of radiation therethrough. Non-limiting examples of windows include automotive and aircraft transparencies, filters, shutters, and optical switches. As used herein the term "mirror" means a surface that specularly reflects a large fraction of incident light. As used herein the term "liquid crystal cell" refers to a structure containing a liquid crystal material that is capable of being ordered. Active liquid crystal cells are cells wherein the liquid crystal material is capable of being switched between ordered and disordered states or between two ordered states by the application of an external force, such as electric or magnetic fields. Passive liquid crystal cells are cells wherein the liquid crystal material maintains an ordered state. One non-limiting example of an active liquid crystal cell element or device is a liquid crystal display.

For example, one non-limiting embodiment provides an optical element comprising (a) a substrate; and (b) at least one photochromic material connected to at least a portion of the substrate, the at least one photochromic material comprising a reaction product of (1) at least one ring-opening cyclic monomer chosen from a cyclic ester and a cyclic carbonate, and (2) a photochromic initiator.

As used herein, the term "connected to" means in direct contact with an object or in indirect contact with an object. For example and without limitation, the photochromic materials disclosed herein can be in direct contact with a portion of the substrate, such as by bonding to a portion of the material from which the substrate is made, blending with the substrate material, or coating on the substrate. Alternatively, they can be in indirect contact with the substrate such as through an intermediate coating, film or layer. For example, according to one non-limiting embodiment, the substrate comprises a polymeric material and the at least one photochromic material is bonded to at least a portion of the polymeric material. According to another non-limiting embodiment, the substrate comprises a polymeric material and the at least one photochromic material is blended with at least a portion of the polymeric material. Non-limiting examples of polymeric materials that are useful in forming the substrates according to various non-limiting embodiments disclosed herein are set forth above in detail.

According to still other non-limiting embodiments, the substrate can be a polymeric substrate or an inorganic substrate (such as, but not limited to, a glass substrate) and the at least one photochromic material can be present as part of an at least partial coating connected to at least a portion of the substrate. For example, one non-limiting embodiment provides an optical element comprising (a) a substrate; and (b) an at least partial coating connected to at least a portion of the substrate, the at least partial coating comprising at least one photochromic material comprising the reaction product of (1) at least one ring-opening cyclic monomer chosen from a cyclic ester and a cyclic carbonate, and (2) a photochromic initiator.

According to various non-limiting embodiments, the at least partial coating comprising the at least one photochromic material can be directly connected to the at least portion of the substrate, for example, by directly applying a coating composition comprising the at least one photochromic material to at least a portion of a surface of the substrate, and at least partially setting the coating composition. As used herein, the term "setting" includes, without limitation, curing, polymerizing, cross-linking, cooling, and drying. Additionally or alternatively, the at least partial coating comprising the at least one photochromic material can be indirectly connected to the substrate, for example, through one or more additional coatings. For example, while not limiting herein, according to various non-limiting embodiments, at least one additional coating composition can be applied to at least a portion of the surface of the substrate, at least partially set, and thereafter the coating composition comprising the at least one photochromic material can be applied to the substrate and at least partially set. Non-limiting methods of applying coatings to substrates are discussed herein below.

Non-limiting examples of other coatings and films that can be used in conjunction with the optical elements disclosed herein include primer coatings; protective coatings, including transitional coatings and abrasion resistant coatings; antireflective coatings; and polarizing coatings and films. As used herein the term "protective coating" refers to coatings that can prevent wear or abrasion, provide a transition in properties from one coating to another, protect against the effects of polymerization reaction chemicals and/or protect against deterioration due to environmental conditions such as moisture, heat, ultraviolet light, oxygen, etc.

Non-limiting examples of primer coatings that can be used in conjunction with various non-limiting embodiments disclosed herein include coatings comprising coupling agents, at least partial hydrolysates of coupling agents, and mixtures thereof. As used herein "coupling agent" means a material having at least one group capable of reacting, binding and/or associating with a group on at least one surface. In one non-limiting embodiment, a coupling agent can serve as a molecular bridge at the interface of at least two surfaces that can be similar or dissimilar surfaces. Coupling agents, in another non-limiting embodiment, can be monomers, pre-polymers and/or polymers. Such materials include, but are not limited to, organo-metallics such as silanes, titanates, zirconates, aluminates, zirconium aluminates, hydrolysates thereof and mixtures thereof. As used herein the phrase "at least partial hydrolysates of coupling agents" means that at least some to all of the hydrolyzable groups on the coupling agent are hydrolyzed. Other non-limiting examples of primer coatings that are suitable for use in conjunction with the various non-limiting embodiments disclosed herein include those primer coatings described U.S. Pat. No. 6,025,026 at col. 3, line 3 to col. 11, line 40 and U.S. Pat. No. 6,150,430 at col. 2, line 39 to col. 7, line 58, which disclosures are hereby specifically incorporated herein by reference.

As used herein, the term "transitional coating" means a coating that aids in creating a gradient in properties between two coatings. For example, although not limiting herein, a transitional coating can aid in creating a gradient in hardness between a relatively hard coating and a relatively soft coating. Non-limiting examples of transitional coatings include radiation-cured acrylate-based thin films as described in U.S. Patent Application Publication 2003/0165686, which coating disclosure is hereby specifically incorporated by reference herein.

Non-limiting examples of abrasion resistant coatings include abrasion-resistant coatings comprising organosilanes, organosiloxanes, abrasion-resistant coatings based on inorganic materials such as silica, titania and/or zirconia, organic abrasion-resistant coatings of the type that are ultraviolet light curable, oxygen barrier-coatings, UV-shielding coatings, and combinations thereof. As used herein the term "abrasion resistant coating" refers to a coating of a protective polymeric material that demonstrates a resistance to abrasion that is greater than a standard reference material, e.g., a polymer made of CR-39® monomer available from PPG Industries, Inc, as tested in a method comparable to ASTM F-735 Standard Test Method for Abrasion Resistance of Transparent Plastics and Coatings Using the Oscillating Sand Method.

Non-limiting examples of antireflective coatings include a monolayer or multilayer of metal oxides, metal fluorides, or other such materials, which can be deposited onto the articles of the present invention through vacuum deposition, sputtering, or some other method. Non-limiting examples of polarizing coatings include, but are not limited to, coatings comprising dichroic compounds that are known in the art.

As discussed above, according to various non-limiting embodiments, these coatings can be applied to the substrate prior to applying the at least partial coating comprising the at least one photochromic material. Alternatively or additionally, these coatings can be applied to the substrate after applying the at least partial coating comprising the at least one photochromic material, for example as an overcoating on the at least partial coating comprising the at least one photochromic material. For example, while not limiting herein, according to various other non-limiting embodiments, the aforementioned coatings can be connected to at least a portion of the same surface of a substrate in the following order from the surface: primer, photochromic, transitional, abrasion resistant, polarizing film or coating, antireflective, and abrasion resistant; or primer, photochromic, transitional, abrasion resistant, and antireflective; or photochromic, transitional, and polarizing; or primer, photochromic, and polarizing; or primer, photochromic, and antireflective. Further, the aforementioned coating can be applied to one or more surfaces of a substrate, e.g., both surfaces of an optical substrate.

Non-limiting embodiments of methods of making photochromic compositions and optical elements according to various non-limiting embodiments disclosed herein will now be discussed. One non-limiting embodiment provides a method of making a photochromic composition, the method comprising connecting at least one photochromic material to at least a portion of a substrate, wherein the at least one photochromic material comprises a reaction product of (1) at least one ring-opening cyclic monomer chosen from a cyclic ester and a cyclic carbonate, and (2) a photochromic initiator.

Non-limiting methods of connecting photochromic materials to a polymeric material include, for example, mixing the photochromic material into a solution or melt of a polymeric, pre-polymeric, or monomeric material, and subsequently at least partially setting the polymeric, pre-polymeric, or monomeric material. It will be appreciated by those skilled in the art that, according to this non-limiting embodiment, in the resultant photochromic composition, the photochromic materials can be blended with the polymeric material (i.e., intermixed with but not bonded to) or bonded to the polymeric material. For example, if the photochromic material contains a reactive functionality that is compatible with the polymeric, pre-polymeric, or monomeric material, during setting of the material the photochromic material can be reacted with at least a portion thereof to bond the photochromic material to the resultant polymeric material.

Another method of connecting a photochromic material to a polymeric material that can be use in conjunction with various non-limiting embodiments disclosed herein is imbibition. According to this method, the photochromic material is caused to diffuse into the polymeric material, for example, by immersing polymeric material in a solution containing the photochromic material, with or with out heating. Thereafter, the photochromic material can be bonded to the polymeric material, for example, if the photochromic material contains a reactive functionality that is compatible with the polymeric material.

Other non-limiting embodiments disclosed herein provide a method of making an optical element comprising: connecting at least one photochromic material to at least a portion of a substrate, wherein the at least one photochromic material comprises a reaction product of (1) at least one ring-opening cyclic monomer chosen from a cyclic ester and a cyclic carbonate, and (2) a photochromic initiator. Non-limiting methods of connecting the photochromic material to at least a portion of the substrate include: imbibition (which is described above), cast-in-place, in-mold casting, coating, and lamination.

According to one non-limiting embodiment, wherein the substrate comprises a polymeric material, the photochromic material can be connected to at least a portion of a substrate by the cast-in-place method. According to this non-limiting embodiment, the photochromic material is mixed with a polymeric solution or melt, or other pre-polymeric and/or monomeric solution or mixture, which is subsequently cast into a molding having a desired shape and at least partially set to form the substrate. According to this non-limiting embodiment, the at least one photochromic material can be bonded to the polymeric material or it can be blended (i.e., intermixed but not bonded) with the polymeric material of the substrate.

According to another non-limiting embodiment, wherein the substrate comprises a polymeric material, the photochromic material can be connected to at least a portion of a substrate by in-mold casting. According to this non-limiting embodiment, a coating composition comprising the photochromic material, which can be a liquid coating composition or a powder coating composition, is applied to the surface of a mold and at least partially set. Thereafter, a polymer solution or melt, or pre-polymer or monomeric solution or mixture is cast over the coating and at least partially set. After setting, the substrate with the coating is removed from the mold. Non-limiting examples of powder coatings in which the photochromic materials according to various non-limiting embodiments disclosed herein can be employed are set forth in U.S. Pat. No. 6,068,797 at col. 7, line 50 to col. 19, line 42, which disclosure is hereby specifically incorporated by reference herein.

According to still another non-limiting embodiment, wherein the substrate comprises a polymeric material or an inorganic material such as glass, the photochromic material can be connected to at least a portion of a substrate by coating. Non-limiting examples of suitable coating methods include, spin coating, spray coating (e.g., using a liquid or powder coating), curtain coating, roll coating, spin and spray coating, in-mold casting, and over-molding. For example, according to one non-limiting embodiment, the photochromic material can be connected to the substrate by over-molding. According to this non-limiting embodiment, a coating composition comprising the photochromic material (which may be a liquid coating composition or a powder coating composition as previously discussed) is applied to a mold and the substrate is then placed into the mold such that the substrate contacts the coating causing it to spread over at least a portion of the surface of the substrate. Thereafter, the coating composition is at least partially set and the coated substrate is removed from the mold. Alternatively, over-molding can be done by placing the substrate into a mold such that an open region is defined between the substrate and the mold, and thereafter injecting a coating composition comprising the photochromic material into the open region. Thereafter, the coating composition can be at least partially set and the coated substrate is removed from the mold.

According to yet another non-limiting embodiment, wherein the substrate comprises a polymeric material or an inorganic material such as glass, the photochromic material can be connected to at least a portion of a substrate by lamination. According to this non-limiting embodiment, a film comprising the photochromic material can be adhered to a portion of the substrate, with or without an adhesive and/or the application of heat and pressure. Thereafter, if desired, a second substrate can be applied over the first substrate and the two substrates can be laminated together (i.e., by the application of heat and pressure) to form an element wherein the film comprising the photochromic material is interposed between the two substrates. Methods of forming films comprising a photochromic material can include for example and without limitation, combining a photochromic material with a polymeric solution or pre-polymer solution or mixture, casting or extruding a film therefrom, and, if required, at least partially setting the film. Additionally or alternatively, a film can be formed (with or without a photochromic material) and imbibed with the photochromic material (as discussed above).

Further, it will be appreciated by those skilled in the art that the photochromic compositions and photochromic coating compositions according to various non-limiting embodiments disclosed herein can further comprise other additives that aid in the processing and/or performance of the composition. For example, and without limitation, the such additives can be chosen from photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, and adhesion promoters (such as hexanediol diacrylate and coupling agents).

As previous discussed, it has been observed by the inventors that photochromic material according to various non-limiting embodiments disclosed herein can have favorable migration performance. Accordingly, one non-limiting embodiment disclosed herein provides a method of inhibiting migration of a photochromic material in a polymeric material, the method comprising bonding the photochromic material to at least a portion of the polymeric material, wherein the photochromic material comprises (1) a photochromic group, and (2) at least one segment comprising the residue a plurality of ring-opening cyclic monomers bonded to the photochromic group, the ring-opening cyclic monomers being chosen from cyclic esters, cyclic carbonates, cyclic ethers, cyclic siloxanes, and combinations thereof, wherein the at least onesegment has a number average molecular weight of at least 1000 g/mol. Further, according to this non-limiting embodiment, the residue of the at least one ring-opening cyclicmonomer can have a number average molecular weight ranging from 2000 to 6000 g/mol.

Various non-limiting embodiments of the present invention will now be illustrated in the following non-limiting examples.

Tin(II) 2-ethyloctonate were charged under nitrogen into a three-neck flask equipped with a condenser, nitrogen inlet and stir bar. The mixture was stirred at room temperature until a dark homogenous solution was formed. Polymerization was carried out at approximately 120° C. for 22 hours. Thereafter, the highly viscous mixture was cooled to approximately 80° C. and transferred to glass bottle. The product is believed to consist of a mixture of photochromic materials having the structure generally represented by Formula 19 below, wherein 'a' is an integer ranging from 1 to 165. The structures were confirmed by mass spectroscopy.

Formula 17

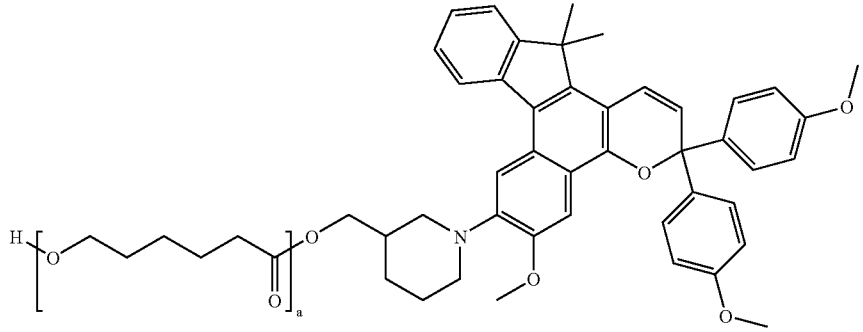

EXAMPLES
Preparation of Photochromic Materials
Example 1

Preparation of Example Photochromic Material "PM-1"

Part A:

A photochromic initiator (represented by structure 1.49 in Table 1 above) was prepared as follows. To an oven-dried reaction flask was added 3-piperidinomethanol (5.1 grams) and tetrahydrofuran anhydrous (330 mL). Reaction mixture was cooled in an ice bath. To this was added 51 mL of butyllithium (2.5 M in hexanes) slowly dropwise over 20 minutes. Reaction mixture was allowed to warm to room temperature and then the desired product of Example 4, Step 6 in U.S. Pat. No. 6,296,785 (3,3-di(4-methoxyphenyl)-6,7-dimethoxy-13,13-dimethyl-3H,13H-indeno[2,1-f]naphtho[1,2-b]pyran, 11.0 grams) was charged. The reaction mixture was stirred overnight at room temperature and then slowly poured into ice water (400 mL). Aqueous hydrochloric acid (10% v/v) was added until the pH was 5 and then diluted with ethyl acetate (200 mL). The layers were phase separated and the aqueous layer was extracted with three 175 mL portions of ethyl acetate. The organic layers were combined and washed with saturated aqueous sodium bicarbonate (200 mL). The organic layer was dried over anhydrous sodium sulfate and concentrated by rotary evaporation. The resulting residue was purified by column chromatography on silica gel (300 grams) eluting with 40% ethyl acetate in hexanes. The photochromic fractions were combined and concentrated by rotary evaporation. The resulting residue was recrystallized in t-butyl methyl ether yielding 5.6 grams of an off-white solid. NMR and Mass Spectrometry analysis showed the product to have a structure and molecular weight consistent with 3,3-di(4-methoxyphenyl)-6-methoxy-7-(3-piperidinomethanol)-13,13-dimethyl-3H,13H-indeno[2,1-f]naphtho[1,2-b]pyran.

Part B:

Example photochromic material "PM-1" was prepared using the photochromic initiator set forth in PART A (above) as follows: 0.8038 g of the photochromic initiator of PART A above, 7.37 g of ε-caprolactone monomer and half drop of

Example 2

Preparation of Example Photochromic Material "PM-2"

A photochromic initiator (represented by structure 1.51 in Table 1 above) was prepared as follows. The product of Example 5 in U.S. Pat. No. 5,645,767 (which example is hereby specifically incorporated by reference) (3,3-di(4-methoxyphenyl)-6,11,13-trimethyl-13-hydroxy-3H,13H-indeno[2,1-f]naphtho[1,2-b]pyran, 200 grams) was added to a reaction flask containing 700 mL triethylene glycol and 750 mL of acetonitrile. The resulting mixture was stirred under a nitrogen atmosphere and heated to 80° C. Subsequently, 2 grams of p-toluene sulfonic acid was added to the reaction mixture. After 30 minutes at 80° C., the reaction was quenched into 8 L of water with vigorous stirring until a green solid precipitated out. The solid was filtered, washed with water, dried in air, and purified by column chromatography. Subsequent crystallization from diethyl ether yielded 152 grams of white solid. NMR analysis showed the product to have a structure consistent with 3,3-di(4-methoxyphenyl)-6,11,13-trimethyl-13-(2-(2-(2-hydroxyethoxy)ethoxy)ethoxy)-3H,13H-indeno[2,1-f]naphtho[1,2-b]pyran.

Part B:

Example photochromic material "PM-2" was prepared using the photochromic initiator set forth in PART A (above) as follows: 40.3190 g of the photochromic initiator of PART A (above), 120.5558 g of ε-caprolactone monomer and 0.4209 g Tin(II) 2-ethyloctonate were charged under nitrogen into a three-neck flask equipped with a condenser, nitrogen inlet and mechanical stirrer. The mixture was stirred at room temperature until a dark homogenous solution was formed. Polymerization of the ε-caprolactone was carried out at 120° C. for 5 hours. Thereafter, the highly viscous mixture was cooled to approximately 80° C. and transferred to glass bottle. The resultant product was a solid at room temperature, with number and weight average molecular weights of 3300 and 4500 g/mol., respectively, as determined by GPC, relative to a polystyrene standard. The product is believed to consist of a mixture of photochromic materials having the structure generally represented by Formula 19 below, wherein 'a' is an integer ranging from 1 to 307.

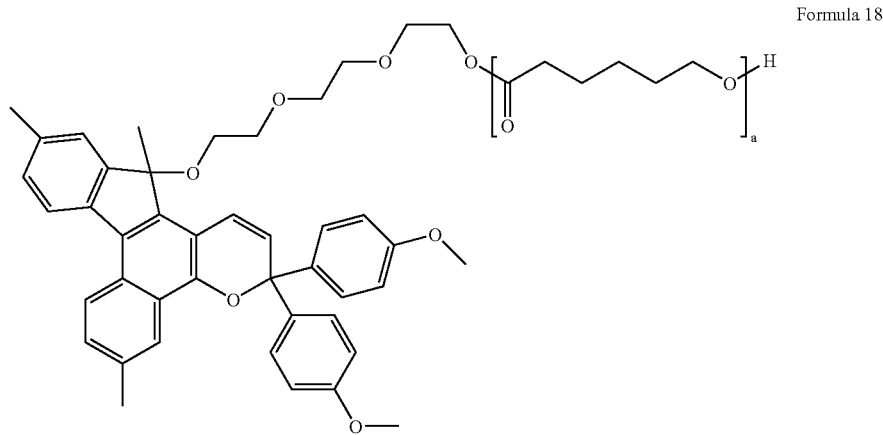

Formula 18

Example 3

Preparation of Example Photochromic Material "PM-3"

Example photochromic material "PM-3" was prepared using the photochromic initiator set forth in PART A of Example 2 (above) as follows: 1.5822 g of the photochromic initiator of PART A of Example 2 (above), 4.7089 g of 6-valerolactone monomer and 0.0157 g Tin(II) 2-ethyloctonate were charged under nitrogen into a three-neck flask equipped with a condenser, nitrogen inlet and a magnetic stir bar. The polymerization procedure was the same as set forth in PART B of Example 2 (above). The resultant product was a solid at room temperature, with number and weight average molecular weights of 2800 and 3500 g/mol., respectively, as determined by GPC relative to a polystyrene standard. The product is believed to consist of a mixture of photochromic materials having the structure generally represented by Formula 19 below, wherein 'a' is an integer ranging from 1 to 166.

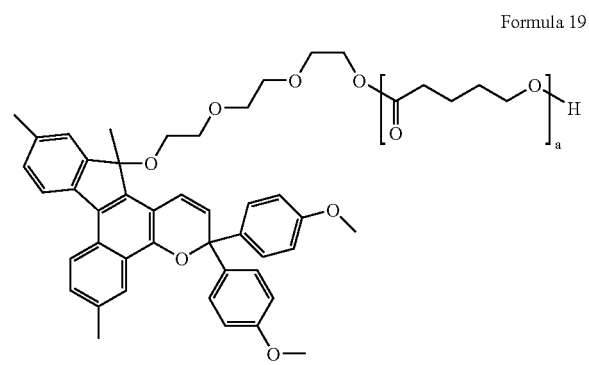

Formula 19

Example 4

Preparation of Example Photochromic Material "PM-4"

xample photochromic material "PM-4" was prepared using the photochromic initiator set forth in PART A of Example 2 (above) as follows: 100.0114 g of the photochromic initiator of PART A of Example 2 (above), 139.0881 g of 6-valerolactone, 158.5649 g of $\epsilon$-caprolactone and 0.9942 g Tin(II) 2-ethyloctonate were charged under nitrogen into a three-neck flask equipped with a condenser, nitrogen inlet and mechanical stirrer. The polymerization procedure is the same set forth in PART B of Example 2 (above). The product material was a viscous liquid at room temperature, with number and weight average molecular weights of 2800 and 3600 g/mol., respectively, as determined by GPC relative to a polystyrene standard. The product is believed to consist of a mixture of photochromic materials having the structure generally represented by Formula 20 below, wherein the "Random Copolymer" is a random copolymer of $\epsilon$-caprolactone and 6-valerolactone.

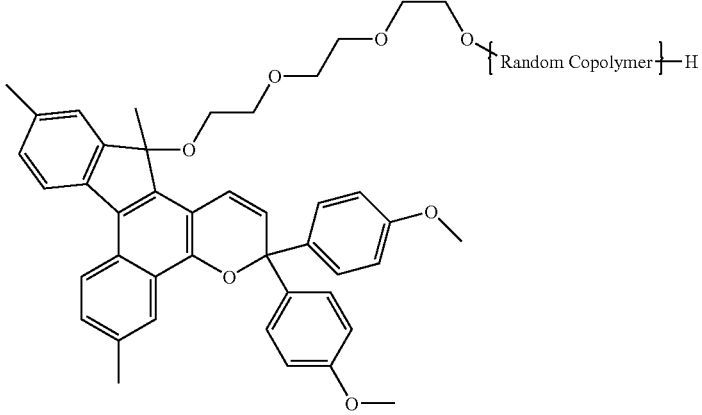

Formula 20

Example 5

Preparation of Example Photochromic Material "PM-5"

Part A:

A photochromic group initiator (represented by structure 1.3 in Table 1 above) was prepared as follows. Step 1: 4-fluoro-4'-(2-hydroxyethoxy)-benzophenone from Part A, Step 1 of Example 7 (below) (7-974) (43.3 grams) and acetylene saturated N,N-dimethylformamide (130 mL) were combined in a reaction flask. Reaction flask was cooled in an ice bath. Sodium acetylide solution (9% by weight in toluene, 221 grams) was added to the cooled reaction mixture dropwise over 30 minutes. The ice bath was removed and the reaction mixture was allowed to warm to room temperature. The reaction mixture was poured into ice water (450 mL) and diethyl ether (300 mL) was added to it. The layers were phase separated and the aqueous layer was extracted one time with diethyl ether (300 mL) and twice with ethyl acetate (300 mL each). The organic layers were combined, dried over anhydrous sodium sulfate, and concentrated by rotary evaporation. The resulting residue was purified by column chromatography on silica gel (600 grams) eluting with a mixture of 45% ethyl acetate in hexanes. The fractions containing pure desired product were combined and concentrated by rotary evaporation to yield 30.1 grams of 1-(4-fluorophenyl)-1-(4'-(2-hydroxyethoxy)phenyl)-2-propyn-1-ol.

Step 2: 1-(4-fluorophenyl)-1-(4'-(2-hydroxyethoxy)phenyl)-2-propyn-1-ol from Step 1 (19.9 grams), 2,3-dimethoxy-5,7-dihydroxy-7-ethyl-7H-benzo[C]fluorene from Part A, Step 4 of Example 8 (below) (18.0 grams), p-toluenesulfonic acid monohydrate (1.02 grams) and chloroform (preserved with pentene, 360 mL) were combined in a reaction flask and stirred at room temperature for 2.5 hours. The reaction mixture was washed with 50% saturated aqueous sodium bicarbonate (300 mL), dried over anhydrous sodium sulfate, and concentrated by rotary evaporation. The resulting residue was purified by column chromatography on silica gel (500 grams) eluting with a mixture of 50% ethyl acetate in hexanes. Fractions containing the desired photochromic were combined and concentrated by rotary evaporation to yield 18.9 grams of 3-(4-fluorophenyl)-3-(4-(2-hydroxyethoxy)phenyl)-6,7-dimethoxy-13-ethyl-13-hydroxy-3H,13H-indeno[2,1-f]naphtho[1,2-b]pyran.

Step 3: 3-(4-fluorophenyl)-3-(4-(2-hydroxyethoxy)phenyl)-6,7-dimethoxy-13-ethyl-13-hydroxy-3H,13H-indeno[2,1-f]naphtho[1,2-b]pyran from Step 2 (18.9 grams), diethylene glycol (190 mL), toluene (190 mL), and p-toluenesulfonic acid monohydrate (0.60 grams) were combined in a reaction flask and heated to 85° C. for 2.5 hours. The reaction mixture was cooled to room temperature and diluted with toluene (190 mL). The reaction mixture was washed with saturated aqueous sodium bicarbonate (350 mL) and two portions of saturated aqueous sodium chloride (350 mL each). The organic layer was dried over anhydrous sodium sulfate and concentrated by rotary evaporation. The resulting residue was chromatographed on silica gel (650 grams) eluting with a mixture of 65% ethyl acetate in hexanes. The pure photochromic fractions were combined and concentrated by rotary evaporation to a dark green oil. NMR analysis showed the product to have a structure consistent with 3-(4-fluorophenyl)-3-(4-(2-hydroxyethoxy)phenyl)-6,7-dimethoxy-13-ethyl-13-(2-(2-hydroxyethoxy)ethoxy)-3H,13H-indeno[2,1-f]naphtho[1,2-b]pyran.

Part B:

Example photochromic material "PM-5" was prepared using the photochromic initiator set forth in PART A (above) as follows: 0.4194 g of the photochromic initiator set forth in Part A (above), 1.6973 g of 6-valerolactone, 1.9349 g of δ-caprolactone and 0.0101 g of Tin(II) 2-ethyloctonate were charged under nitrogen into a three-neck flask equipped with a condenser, nitrogen inlet and a magnetic stir bar. The polymerization procedure was the same as set forth in PART B of Example 2 (above). The product was a viscous liquid at room temperature, with number and weight average molecular weights of 8800 and 9800 g/mol., respectively, as determined by GPC relative to a polystyrene standard. The product is believed to consist of a mixture of photochromic materials having the structure generally represented by Formula 21 below, wherein the "Random Copolymer" is a random copolymer of α-caprolactone and 6-valerolactone.

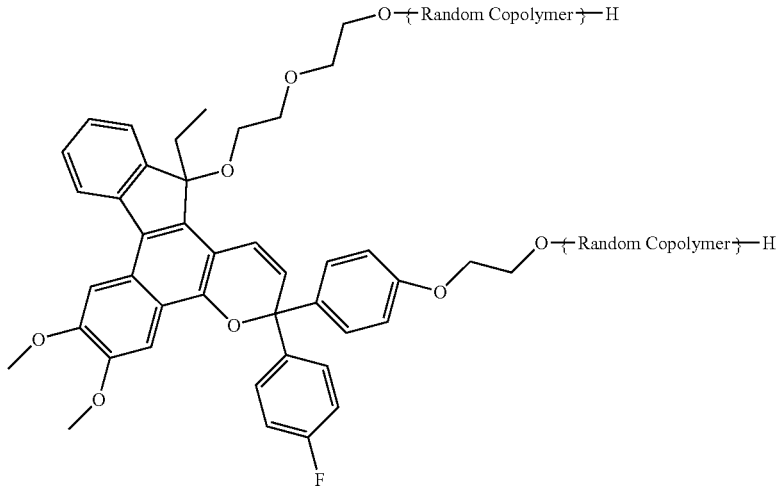

Formula 21

Example 6

Preparation of Example Photochromic Material "PM-6"

Example photochromic-material "PM-6" was prepared using the photochromic initiator set forth in PART A of Example 2 (above) as follows: 12.1814 g of the photochromic initiator of PART A of Example 2 (above), 11.2488 g of 6-valerolactone, 12.8240 g of α-caprolactone and 0.0906 g of Tin(II) 2-ethyloctonate were charged under nitrogen into a three-neck flask equipped with a condenser, nitrogen inlet and a mechanical stirrer. The polymerization procedure is the same set forth in PART B of Example 2 (above). After the polymerization, the resultant mixture was cooled to 80° C., one drop dibutyltin dilaurate was added and 2.8097 g of 2-isocyanatoethyl methacrylate was charged over 30 minutes at approximately 80° C. The reaction was kept at 80° C. until no isocyanate groups were detected by IR. The product was a viscous liquid at room temperature, with number and weight average molecular weights of 2400 and 3900 g/mol., respectively, as determined by GPC relative to a polystyrene standard. The product is believed to consist of a mixture of photochromic materials having the structure generally represented by Formula 22 below, wherein the "Random Copolymer" is a random copolymer of ε-caprolactone and δ-valerolactone.

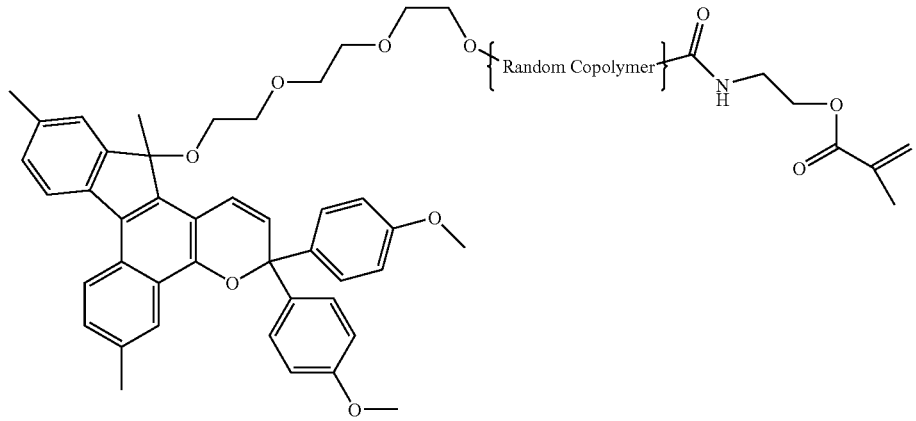

Formula 22

Example 7

Preparation of Example Photochromic Material "PM-7"

Part A:

A photochromic initiator (represented by structure 1.37 in Table 1) was prepared as follows. Step 1: 4-hydroxy-4'-fluoro-benzophenone (100 grams), 2-chloroethanol (93 grams), sodium iodide (14 grams), potassium carbonate (128 grams) were added to a reaction flask containing 400 mL of N,N-dimethylformamide. The resulting mixture was heated to 95° C. and stirred under a nitrogen atmosphere. After 4 hours at 95° C., an additional 30 grams of 2-chloroethanol and 5 grams of sodium iodide were added to the reaction mixture. After another 14 hours at 95° C., the reaction was quenched into a mixture of 50 mL of a 50% sodium hydroxide solution and 4 L of water with vigorous stirring to precipitate out a white solid. The solid was filtered, washed with water and dried open to air to obtain 117 grams of the desired product, 4-(2-hydroxyethoxy)-4'-fluoro-benzophenone. This material was used in the next step without further purification.

Step 2: The product of Step 1,4-(2-hydroxyethoxy)-4'-fluoro-benzophenone (90 grams), morpholine (75.3 grams), triethylamine (69.9 grams) were added to a reaction flask containing 160 mL of dimethylsulfoxide. The resulting mixture was heated to 95° C. and stirred under a nitrogen atmosphere. After 4 hours at 95° C., an additional 40 grams of morpholine and 35 grams of triethylamine were added to the reaction mixture. After another 14 hours at 95° C., an additional 60 grams of morpholine was added to the reaction mixture. After another 24 hours at 95° C., the reaction was quenched into 5 L of water with vigorous stirring to see a light yellow solid precipitate out. The solid was filtered, washed with water and dried open to air to obtain 105 grams of the desired product, 4-(2-hydroxyethoxy)-4'-morpholino-benzophenone. This material was used in the next step without further purification.

Step 3: The product of Step 2,4-(2-hydroxyethoxy)-4'-morpholino-benzophenone (105 grams) was added to a reaction flask containing 600 mL of N,N-dimethylformamide saturated with acetylene. The resulting mixture was stirred using a mechanical stirrer at room temperature under a nitrogen atmosphere. Sodium acetylide in xylenes/mineral oil (214 grams of an 18% by weight solution) was added over thirty minutes to the reaction mixture while stirring. After stirring for half hour at room temperature, the reaction was quenched into 4 L of water with vigorous stirring to see a light yellow solid precipitate out. The solid was filtered, washed with water and dried open to air to obtain 111.1 grams of the desired product, 1-(4-(2-hydroxyethoxy)-phenyl-1-(4-morpholinophenyl)-2-propyn-1-ol. This material was used in the next step without further purification.

Step 4: The product of example 1 step 2 in U.S. Pat. No. 5,645,767 (1-phenyl-2-methoxycarbonyl-4-acetoxynaphthalene, 50 grams) was added to a reaction flask containing 500 mL of tetrahydrofuran. The resulting mixture was cooled in a ice water bath and stirred under a nitrogen atmosphere. 703 mL of a methyl magnesium chloride solution (1M in tetrahydrofuran) was added dropwise over forty-five minutes. The resulting yellow reaction mixture was stirred at 0° C. for 2 hours and slowly warmed to room temperature. The reaction mixture was poured into 2 L of an ice/water mixture. Ether (1 L) was added, and the layers separated. The aqueous layer was extracted with two 500 mL portions of ether, and the organic portions were combined and washed with 1 L of water. The organic layer was dried over anhydrous sodium sulfate and concentrated by rotary evaporation. The resulting oil was transferred into a reaction vessel (fitted with a Dean-Stark trap) containing 500 mL of toluene to which ten drops of dodecylbenzene sulfonic acid were added. The reaction mixture was heated to reflux for 2 hours and cooled. The toluene was removed via rotary evaporation to yield 40.2 grams of an light yellow solid. An NMR spectrum showed the product to have a structure consistent with 7,7-dimethyl-5-hydroxy-7H-benzo[C]fluorene. This material was not purified further but was used directly in the next step.

Step 5: The product of step 4,7,7-dimethyl-5-hydroxy-7H-benzo[C]fluorene (40 grams), the product of step 3,1-(4-(2-hydroxyethoxy)-phenyl-1-(4-morpholinophenyl)-2-propyn-1-ol (54.3 grams), twenty drops of methane sulfonic acid and 800 mL of chloroform were combined in a reaction flask and stirred at reflux temperatures under a nitrogen atmosphere. After two hours, an additional 5 grams of 1-(4-(2-hydroxyethoxy)-phenyl-1-(4-morpholinophenyl)-2-propyn-1-ol was added to the reaction mixture followed by another 5 gram addition after another two hours. The reaction mixture was heated at reflux for 16 hours and then cooled to room temperature. The reaction mixture was washed carefully with a mixture of 500 mL of a saturated sodium bicarbonate solution and 500 mL of water. The organic layer was separated, dried over sodium sulfate, and concentrated by rotary evaporation. The residue was chromatographed on a silica gel column using a mixture of hexane, methylene chloride and ethyl acetate (50/40/10) as the eluant. Photochromic fractions were collected and concentrated by rotary evaporation to obtain a bluish solid (66 grams). An NMR spectrum showed the product to have a structure consistent with 3-(4-(2-hydroxyethoxy)-phenyl-3-(4-morpholinophenyl)-13,13-dimethyl-3H,13H-indeno[2,1-f]naphtho[1,2-b]pyran.

Part B:

Example photochromic material "PM-7" was prepared using the photochromic initiator set forth in PART A (above) as follows: 1.4230 g of the photochromic initiator set forth in PART A above, 4.7830 g of ε-caprolactone monomer, and 0.0064 g of tin(II) 2-ethyloctonate were charged under nitrogen into a three-neck flask equipped with a condenser, nitrogen inlet and magnetic stir bar. The reaction mixture was stirred at room temperature until a dark homogeneous solution was formed. Polymerization was subsequently carried out at 140° C. for 10 hours. Thereafter, the highly viscous mixture was cooled to approximately 80° C. and transferred to a glass bottle. The product was a solid at room temperature, with number and weight average molecular weights of 1800 and 3100 g/mol., respectively, as determined by GPC relative to a polystyrene standard. The product is believed to be a mixture of photochromic materials having the general structure represented by Formula 23 below, wherein 'a' is an integer ranging from 1 to 228.

Formula 23

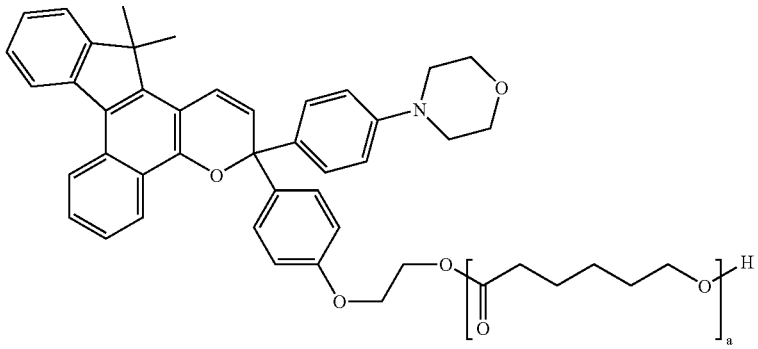

Example 8

Preparation of Example Photochromic Material "PM-8"

PART A: Preparation of Photochromic Initiator

A photochromic initiator (represented by structure 1.32 in Table 1) was prepared as follows. Step 1: The product of Example 4 Step 2 in U.S. Pat. No. 6,296,785 (mixture of E and Z isomers of 4-(3,4-dimethoxyphenyl)-4-phenyl-3-methoxycarbonyl-3-butenoic acids, 225 grams) and acetic anhydride (900 mL) were added to a reaction flask under a nitrogen atmosphere. The reaction mixture was heated to reflux for 5 hours. The reaction mixture was cooled to room temperature and the resulting precipitate was collected by vacuum filtration and washed with cold methanol yielding 211 grams of 1-phenyl-2-methoxycarbonyl-4-acetoxy-6,7-dimethoxynaphthalene. The product was used without further purification in the subsequent reaction.

Step 2: 1-phenyl-2-methoxycarbonyl-4-acetoxy-6,7-dimethoxynaphthalene from step 1 (100 grams), water (675 mL), methanol (35 mL), and sodium hydroxide (75 grams) were combined in a reaction flask and heated to reflux for 1 hour. The reaction mixture was cooled to room temperature and slowly poured into 1.5 L of a 4N HCl/ice mixture. Additional 4N HCl was added until the pH of the reaction mixture was three. The resulting white precipitate was collected by vacuum filtration and washed with water yielding 96 grams of 1-phenyl-2-hydroxycarbonyl-4-hydroxy-6,7-dimethoxy-naphthalene. The product was used without further purification in the subsequent reaction.

Step 3: 1-phenyl-2-hydroxycarbonyl-4-hydroxy-6,7-dimethoxy-naphthalene from step 2 (105 grams), acetic anhydride (420 mL), acetic acid (630 mL), and zinc chloride (7 grams) were combined in a reaction flask and heated to reflux for ten hours. The reaction mixture was cooled and the resulting precipitate was collected by vacuum filtration and washed with acetic acid followed by water yielding an orange solid. This solid was slurried in saturated aqueous sodium bicarbonate for fifteen minutes, collected by vacuum filtration and washed with water yielding an orange solid. The orange solid was slurried in hot methanol, cooled to room temperature, collected by vacuum filtration, and washed with cold methanol yielding 84.2 grams of 2,3-dimethoxy-5-acetoxy-7H-benzo[C]fluoren-7-one. The product was used without further purification in the subsequent reaction.

Step 4: A reaction flask was charged with 2,3-dimethoxy-5-acetoxy-7H-benzo[C]fluoren-7-one from Step 3 (50.0 grams) under a nitrogen atmosphere. Anhydrous tetrahydrofuran (1250 mL) was added to the reaction flask. The reaction mixture was cooled in an ice bath and 178 mL of an ethyl magnesium bromide solution (3.0M in diethyl ether) was added dropwise over thirty minutes. The reaction mixture was slowly warmed to room temperature and subsequently poured into saturated aqueous ammonium chloride and ice mixture (1.3 L). The layers were phase separated and the aqueous layer was extracted with two 750 mL portions of ethyl acetate. The organic portions were combined and washed with saturated aqueous sodium bicarbonate (800 mL). The organic layer was dried over anhydrous sodium sulfate and concentrated by rotary evaporation. The resulting orange solid was slurried in hot t-butyl methyl ether, cooled to room temperature, collected by vacuum filtration, and washed with cold t-butyl methyl ether yielding 41.3 grams of 2,3-dimethoxy-5,7-dihydroxy-7-ethyl-7H-benzo[C]fluorene. The product was used without further purification in the subsequent reaction.

Step 5: 2,3-dimethoxy-5,7-dihydroxy-7-ethyl-7H-benzo[C]fluorene from Step 4 (30 g), morpholine (46.7 mL), and anhydrous tetrahydrofuran (900 mL) were combined in a reaction flask. The reaction mixture was cooled in an ice bath and a n-butyllithium solution (2.5M in hexanes, 178 mL) was added dropwise over 30 minutes. The ice bath was removed and the reaction mixture was heated to reflux for 3 hours. The reaction mixture was cooled to room temperature and then poured into a saturated aqueous ammonium chloride and ice mixture (1 L). The layers were phase separated and the aqueous layer was extracted with two 350 mL portions of ethyl acetate. The organic portions were combined and washed with saturated aqueous sodium bicarbonate (500 mL). The organic layer was dried over anhydrous sodium sulfate and concentrated by rotary evaporation. The resulting orange solid was slurried in hot t-butyl methyl ether, cooled to room temperature, collected by vacuum filtration and washed with cold t-butyl methyl ether yielding 26.6 grams of 2-morpholino-3-methoxy-5,7-dihydroxy-7-ethyl-7H-benzo[C]fluorene. The product was used without further purification in the subsequent reaction.

Step 6: 2-morpholino-3-methoxy-5,7-dihydroxy-7-ethyl-7H-benzo[C]fluorene from Step 5 (20 grams), the product of example 1 step 1 in U.S. Pat. No. 5,458,814 (1,1-bis(4-methoxyphenyl)-2-propyn-1-ol, 17.8 grams), dodecylbenzene sulfonic acid (1.7 grams) and chloroform (preserved with pentene, 600 mL) were combined in a reaction flask and stirred at room temperature for 2 hours. The reaction mixture was washed with 50% saturated aqueous sodium bicarbonate (300 mL) and the organic layer was dried over anhydrous sodium sulfate. The organic layer was concentrated by rotary evaporation. Added hot methanol to the resulting residue and then cooled to room temperature. The precipitate obtained was collected by vacuum filtration and washed with cold methanol yielding 26.8 grams of 3,3-di(4-methoxyphenyl)-6-methoxy-7-morpholino-13-ethyl-13-hydroxy-3H,13H-indeno[2, 1-f]naphtho[1,2-b]pyran. The product was used without further purification in the subsequent reaction.

Step 7: 3,3,-di(4-methoxyphenyl)-6-methoxy-7-morpholino-13-ethyl-13-hydroxy-3H,13H-indeno[2,1-f]naphtho[1,2-b]pyran from Step 6 (12 grams), diethylene glycol (120 mL), toluene (120 mL), and p-toluene sulfonic acid monohydrate (0.36 grams) were combined in a reaction flask and heated to 85° C. for 4 hours. The reaction mixture was cooled to room temperature and diluted with toluene (120 mL). Reaction mixture was washed with saturated aqueous sodium bicarbonate (100 mL) and four portions (100 mL each) of saturated aqueous sodium chloride. The organic layer was dried over anhydrous sodium sulfate and concentrated to a dark colored oil. The oil was chromatographed on a silica gel column eluting with a mixture of 40% ethyl acetate in hexanes. Photochromic fractions were collected and concentrated by rotary evaporation. The resulting residue was recrystallized in a mixture of 40% hexanes in t-butyl methyl ether to yield 5 grams of an off-white solid. NMR analysis showed the product to have a structure consistent with 3,3-di(4-methoxyphenyl)-6-methoxy-7-morpholino-13-ethyl-13-(2-(2-hydroxyethoxy)ethoxy)-3H,13H-indeno[2,1-f]naphtho[1,2-b]pyran.

Part B:

Example photochromic material "PM-8" was prepared using the photochromic initiator set forth in PART A (above) as follows: 1.695 g of the photochromic initiator set forth in PART A above, 4.6440 g of ε-caprolactone monomer and 0.0062 g of tin(II) 2-ethyloctonate were charged under nitrogen into a three-neck flask equipped with a condenser, nitrogen inlet and magnetic stir bar. The reaction mixture was stirred at room temperature until a dark homogeneous solution was formed. Polymerization was carried out at 140° C. for 6 hours. Thereafter, the highly viscous mixture was cooled to approximately 80° C. and transferred to a glass bottle. The product was as solid at room temperature, with number and weight average molecular weights of 2000 and 3100 g/mol., respectively, as determined by GPC relative to a polystyrene standard. The product is believed to be a mixture of photochromic materials having the general structure represented by Formula 24 below, wherein 'a' is an integer ranging from 1 to 166.

grams), 4-fluorobenzoyl chloride (35 grams) and dichloromethane (250 mL) were combined in a reaction flask. Aluminum chloride (30.8 grams) was added to the reaction mixture slowly over 20 minutes. Stirred the reaction mixture at room temperature for two hours and then poured it into a mixture of 70 mL concentrated hydrochloric acid and 500 mL of water. The layers were phase separated and the aqueous layer was extracted with two portions of dichloromethane (300 mL each). The organic portions were combined and washed with saturated aqueous sodium bicarbonate (400 mL). The organic layer was dried over anhydrous sodium sulfate and evaporated to yield 48.0 grams of 4-fluoro-4'-methoxy-benzophenone as a white solid. This material was not purified further but was used directly in the next step.

Step 2: 4-fluoro-4'-methoxy-benzophenone from Step 1 (126.7 grams) and acetylene saturated N,N-dimethylformamide (380 mL) were combined in a reaction flask. Sodium acetylide solution (9% by weight in toluene, 343 grams) was added to the reaction mixture dropwise over 45 minutes. The reaction mixture was stirred at room temperature for 1 hour and then poured into ice water (600 mL). The layers were phase separated and the aqueous layer was extracted with three portions of diethyl ether (200 mL). The organic layers were combined and washed with saturated aqueous ammonium chloride (200 mL), saturated aqueous sodium chloride (200 mL), and saturated aqueous sodium bicarbonate (200 mL). The organic layer was dried over anhydrous sodium sulfate and evaporated to an amber colored oil yielding 136.6 grams of 1-(4-fluorophenyl)-1-(4-methoxyphenyl)-2-propyn-1-ol. This material was not purified further but was used directly in the next step.

Step 3: 1-(4-fluorophenyl)-1-(4-methoxyphenyl)-2-propyn-1-ol from Step 2 (26.3 grams), 2,3-dimethoxy-5,7-dihydroxy-7-ethyl-7H-benzo[C]fluorine from Step 4 of PART A of Example 8 (30.0 grams), dodecylbenzene sulfonic acid (2.9 grams) and chloroform (preserved with pentene, 600 mL) were combined in a reaction flask and stirred at room temperature for 1 hour. The reaction mixture was washed with 50% saturated aqueous sodium bicarbonate (300 mL) and the organic layer was dried over anhydrous sodium sulfate.

Formula 24

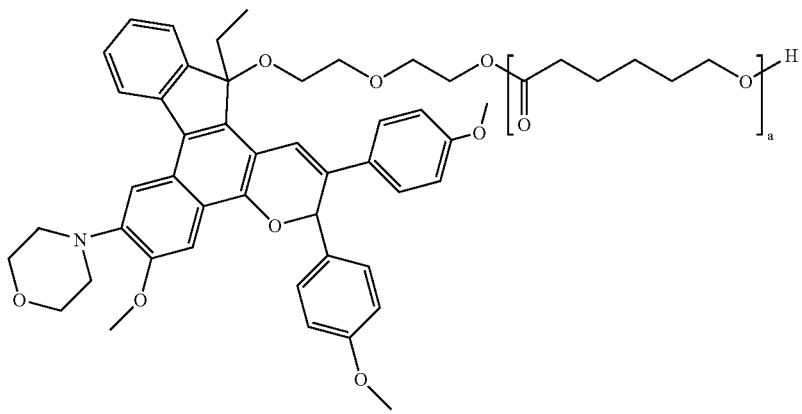

Example 9

Preparation of Example Photochromic Material "PM-9"

PART A: Preparation of Photochromic Initiator

A photochromic initiator (represented by structure 1.31 in Table 1 above) was prepared as follows. Step 1: Anisole (27.5

Evaporated the organic layer to a dark colored oil to which warm methanol was added. The resulting precipitate was collected by vacuum filtration and washed with cold methanol yielding 34.5 grams of 3-(4-fluorophenyl)-3-(4-methoxyphenyl)-6,7-dimethoxy-13-ethyl-13-hydroxy-3H,13H-indeno[2,1-f]naphtho[1,2-b]pyran. This material was used directly in the next step without further purification.

Step 4: 3-(4-fluorophenyl)-3-(4-methoxyphenyl)-6,7-dimethoxy-13-ethyl-13-hydroxy-3H,13H-indeno[2,1-f]naphtho[1,2-b]pyran from Step 7 (35.0 grams), diethylene glycol (350 mL), toluene (350 mL), and p-toluene sulfonic acid monohydrate (1.73 grams) were combined in a reaction flask and heated to 85° C. for 6 hours. The reaction mixture was cooled to room temperature and diluted with toluene (350 mL). The reaction mixture was washed with saturated aqueous sodium bicarbonate (300 mL) and four portions of saturated aqueous sodium chloride (300 mL each). The organic layer was dried over anhydrous sodium sulfate and concentrated to a dark colored oil. The oil was chromatographed on silica gel eluting with a mixture of 25% ethyl acetate in hexanes. The photochromic fractions were collected and concentrated by rotary evaporation. The resulting residue was recrystallized in a mixture of 10% hexanes in t-butyl methyl ether yielding 16.6 grams of a white solid. NMR analysis showed the product to have a structure consistent with 3-(4-fluorophenyl)-3-(4-methoxyphenyl)-6,7-dimethoxy-13-ethyl-13-(2-(2-hydroxyethoxy)ethoxy)-3H,13H-indeno[2,1-f]naphtho[1,2-b]pyran.

Part B:

Example photochromic material "PM-9" was prepared using the photochromic initiator set forth in PART A (above) as follows: 1.6577 g of the photochromic initiator set forth in PART A above, 5.0002 g of ε-caprolactone monomer and 0.0067 g tin(II) 2-ethyloctonate were charged under nitrogen into a three-neck flask equipped with a condenser, nitrogen inlet and magnetic stir bar. The reaction mixture was stirred at room temperature until a dark homogenous solution was formed. Polymerization was carried out at 140° C. for 8 hours. Thereafter, the highly viscous mixture was cooled to approximately 80° C. and transferred to glass bottle. The product was a solid at room temperature, with number and weight average molecular weights of 2200 and 3700 g/mol., respectively, as determined by GPC relative to a polystyrene standard. The product is believed to be a mixture of photochromic materials having the general structure represented by Formula 25 below, wherein 'a' is an integer ranging from 1 to 382.

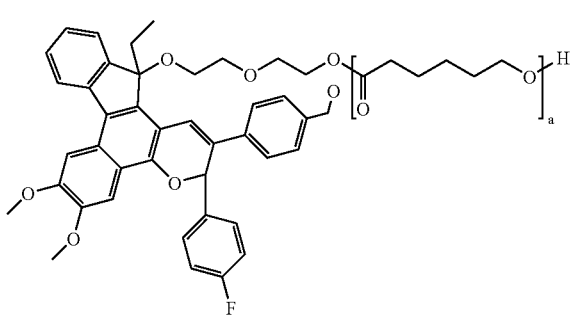

Formula 25

Example 10

Preparation of Example Photochromic Material "PM-10"

Example photochromic material "PM-10" was prepared using the photochromic initiator set forth in PART A of Example 8 (above) as follows: 1.6310 g of the photochromic initiator of PART A of Example 8, 8.9370 g of ε-caprolactone monomer, and 0.0120 g Tin(II) 2-ethyloctonate were charged under nitrogen into a three-neck flask equipped with a condenser, nitrogen inlet and magnetic stir bar. The reaction mixture was stirred at room temperature until a dark homogenous solution was formed. Polymerization was carried out at 140° C. for 10 hours. Thereafter, the highly viscous mixture was cooled to approximately 80° C. and transferred to glass bottle. The product was a solid at room temperature, with number and weight average molecular weights of 3100 and 7200 g/mol., respectively, as determined by GPC relative to a polystyrene standard. The product is believed to be a mixture of photochromic materials having the general structure represented by Formula 25 (above), wherein 'a' is an integer ranging from 1 to 665.

Example 11

Preparation of Example Photochromic Material "PM-11"

Example photochromic material "PM-11" was prepared using the photochromic initiator set forth in PART A of Example 7 (above) as follows: 1.8334 g of the photochromic initiator set forth in PART A of Example 7, 3.080 g of ε-caprolactone monomer, and 0.0041 g Tin(II) 2-ethyloctonate were charged under nitrogen into a three-neck flask equipped with a condenser, nitrogen inlet and magnetic stir bar. The reaction mixture was stirred at room temperature until a dark homogenous solution was formed, and the polymerization was carried out at 140° C. for 7 hours. Thereafter the very viscous mixture was cooled to approximately 80° C. and transferred to glass bottle. The product was a solid at room temperature, with number and weight average molecular weights of 1300 and 1900 g/mol, respectively, as determined by GPC relative to a polystyrene standard. The product is believed to be a mixture of photochromic materials having the general structure represented by Formula 25 (above), wherein 'a' is an integer ranging from 1 to 117.

Example 12

Preparation of Example Photochromic Material "PM-12"

Example photochromic material "PM-12" was prepared using the photochromic initiator set forth in PART A of Example 9 (above) as follows: 1.2358 g of the photochromic initiator set forth in PART A of Example 9 above, 7.4580 g of ε-caprolactone monomer, and 0.0100 g Tin(II) 2-ethyloctonate were charged under nitrogen into a three-neck flask equipped with a condenser, nitrogen inlet and magnetic stir bar. The reaction mixture was stirred at room temperature until a dark homogenous solution was formed. Polymerization was carried out at 140° C. for 10 hours. Thereafter, the highly viscous mixture was cooled to approximately 80° C. and transferred to glass bottle. The product was a solid at room temperature, with number and weight average molecular weights of 3100 and 8100 g/mol., respectively, as determined by GPC relative to a polystyrene standard. The product is believed to be a mixture of photochromic materials having the general structure represented by Formula 25 (above), wherein 'a' is an integer ranging from 1 to 853.

Example 13

Preparation of Example Photochromic Material "PM-13"

PART A: Preparation of Photochromic Initiator

A photochromic initiator (represented by structure 1.18 in Table 1) was prepared as follows: 9.4 g (0.02 moles) of 2,2-bis(4-methoxyphenyl)-5-methoxycarbonyl-6-hydroxy-[2H]-naphtho[1,2-b]pyran was dissolved in 100 ml of DMF dimethyl formamide (DMF) in a 300 ml round bottom flask.

Powdered anhydrous potassium carbonate (13.8 g, 0.1 moles) is added and the mixture stirred and heated to 80° C. while 5 g (0.04 moles) of 2-bromoethanol is added drop-wise. The reaction is monitored by TLC (thin layer chromatography) and after 4 hours with starting material no longer being present, the reaction is quenched by pouring into a liter of water. The product is extracted into chloroform, concentrated and chromatographed on silica using 2:1 ethylacetate:hexane as eluent. The red photochromic fractions are collected and the product crystallized from a diethyl ether: hexane mixture. The resultant material was 2,2-di(4-methoxyphenyl)-5-methoxycarbonyl-6-(2-hydroxyethoxy)-[2H]-naphtho[1,2-b]pyran represented by the structure 1.18 in Table 1 above.

Part B:

Example photochromic material "PM-13" was prepared using the photochromic initiator set forth in PART A (above) as follows: 1.4580 g of the photochromic initiator set forth in PART A above, 3.0340 g of ε-caprolactone, 2.6613 g δ-valerolactone, and 0.0179 g Tin(II) 2-ethyloctonate were charged under nitrogen into a three-neck flask equipped with a condenser, nitrogen inlet and magnetic stir bar. The reaction mixture was stirred at room temperature until a dark homogenous solution was formed. Polymerization was carried out at 120° C. for 7 hours. Thereafter, the highly viscous mixture was cooled to approximately 80° C. and transferred to glass bottle. The product was a liquid at room temperature, with number and weight average molecular weights of 2900 and 3400 g/mol. as determined by GPC relative to a polystyrene standard. The product is believed to be a mixture of photochromic materials having the general structure represented by Formula 26 below, wherein the "Random Copolymer" is a random copolymer of ε-caprolactone and δ-valerolactone.

had the structure set forth above in Formula 18, except that the hydroxyl group was capped with a p-anisic ester group.

Example 15

Preparation of Example Photochromic Material "PM-15"

Example photochromic material "PM-15" was prepared using the photochromic initiator set forth in PART A of Example 2 (above) as follows: 1.2475 g of the photochromic initiator of PART A of Example 2 (above), 3.7128 g of trimethylene carbonate (TMC) monomer and 0.0124 g Tin(II) 2-ethyloctonate were charged under nitrogen into a three-neck flask equipped with a condenser, nitrogen inlet and a magnetic stir bar. The polymerization procedure was the same as set forth in PART B of Example 2 (above). The product was a solid at room temperature, with number and weight average molecular weights of 2700 and 4700 g/mol., respectively, as determined by GPC relative to polystyrene standard. The product is believed to be a mixture of photochromic materials having the general structure represented by Formula 27 below, wherein 'a' is an integer ranging from 1 to 402.

Formula 26

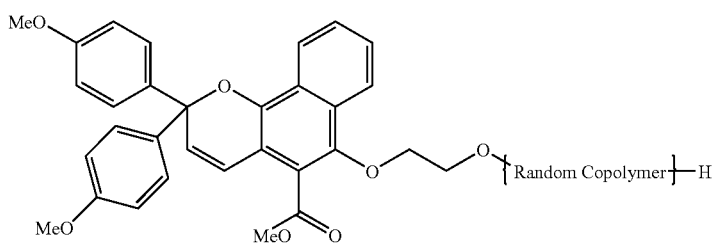

Example 14

Preparation of Example Photochromic Material "PM-14"

Photochromic material PM-14 was prepared as follows: 6.5 g of photochromic material PM-2, which is described above in Example 2, was dissolved with stirring, in 50 ml of chloroform. A molar excess of triethylamine along with a catalytic amount of 4-dimethyaminopyridine (DMAP) was then added followed by five drops of 4-methoxybenzoyl chloride. The progress of the reaction was followed by TLC. After two hours, five more drops of the benzoyl chloride were added. The process was repeated until TLC showed no more starting material present. At this point, the reaction mixture was poured into 250 ml of water. The organic fraction was separated, concentrated, then chromatographed on silica using a 2:1 mixture of hexane: ethylacetate. The photochromic fractions were collected, combined and concentrated to give an oil that solidified on standing. The resultant material Formula 27

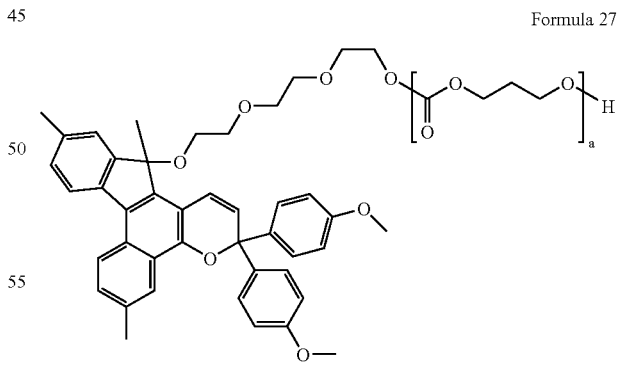

Example 16

Preparation of Example Photochromic Material "PM-16"

Example photochromic material "PM-16" was prepared using the photochromic initiator set forth in PART A of Example 2 (above) as follows: 2.1127 g of the photochromic initiator of PART A of Example 2 (above), 6.2878 g of lactide (LT) monomer and 0.0210 g Tin(II) 2-ethyloctonate were charged under nitrogen into a three-neck flask equipped with a condenser, nitrogen inlet and a magnetic stir bar. The polymerization procedure was the same as set forth in PART B of Example 2 (above). The product was a solid at room temperature, with number and weight average molecular weights of 1756 and 3840 g/mol., respectively, as determined by GPC relative to polystyrene standard. The product is believed to be a mixture of photochromic materials having the general structure represented by Formula 28 below, wherein 'a' is an integer ranging from 1 to 209.

Formula 28

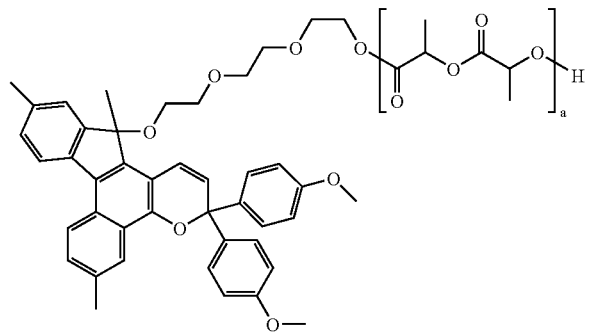

Testing

Example 17

A photochromic coating composition (indicated as "Example Coating 1" in Table 3 below) was prepared using photochromic material PM-1 set forth in Example 1. In addition, two comparative photochromic coating compositions, indicated in Table 3 as "Comparative Coating A" and "Comparative Coating B," were prepared using the following comparative photochromic materials "CPM-A" and "CPM-B," respectively.

Comparative example photochromic material CPM-A (which is represented by Formula 29 below was prepared as follows. To an oven-dried reaction flask was added piperidine (1.5 mL) and tetrahydrofuran anhydrous (150 mL). Reaction mixture was cooled in an ice bath. To this was added 7 mL of butyllithium (2.5 M in hexanes) slowly dropwise over 20 minutes. Reaction mixture was allowed to warm to room temperature and then the desired product of Example 4, Step 6 in U.S. Pat. No. 6,296,785 (3,3-di(4-methoxyphenyl)-6,7-dimethoxy-13,13-dimethyl-3H,13H-indeno[2,1-f]naphtho [1,2-b]pyran, 5.0 grams) was charged. The reaction mixture was stirred overnight at room temperature and then slowly poured into ice water (250 mL). Aqueous hydrochloric acid (10% v/v) was added until the pH was 4 and then diluted with ethyl acetate (100 mL). The layers were phase separated and the aqueous layer was extracted with three 100 mL portions of ethyl acetate. The organic layers were combined and washed with saturated aqueous sodium bicarbonate (200 mL). The organic layer was dried over anhydrous sodium sulfate and concentrated by rotary evaporation. The resulting residue was recrystallized in t-butyl methyl ether yielding 1.6 grams of a white solid. NMR and Mass Spectrometry analysis showed the product to have a structure and molecular weight consistent with 3,3-di(4-methoxyphenyl)-6-methoxy-7-piperidino-13,13-dimethyl-3H,13H-indeno[2,1-f]naphtho[1,2-b]pyran.

Formula 29

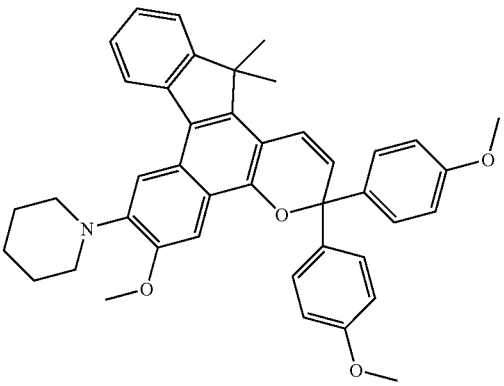

Comparative example photochromic material CPM-B was the photochromic material set forth in Part A of Example 1.

Each coating compositions was prepared by pre-dissolving the appropriate photochromic material in N-methylpyrrolidinone ("NMP") and subsequently adding the remaining components set forth in Table 3 in the listed amounts to this solution. The resultant mixture was stirred using a magnetic stir bar for approximately 30 minutes until a homogeneous mixture was obtained. After mixing, each coating composition was applied to a Gentex PDQ hardcoated polycarbonate lens (1.5×70 mm), which had been previously plasma treated, by spin coatings at 1500 rpm for 6 seconds to a wet weight of approximately 0.2 g. The coatings were cured at 120° C. for 1 hour to a final thickness of approximately 20 microns. The components of the coating compositions were adjust such that each of the three-coatings had essentially the same Fischer Hardness-(as indicated in Table 3). The Fischer Hardness and photochromic performance of each of the coated lenses were measured as discussed below.

TABLE 3

| | Amount in Grams (g) | | |
|---|---|---|---|
| Component | Example Coating 1 | Comparative Coating A | Comparative Coating B |
| HDI biuret B17960[1] | 1.0 | 1.0 | 1.0 |
| HC-86-7726[2] | 0.5 | 0.5 | 0.5 |
| PC-1122[3] | 0.5 | 0.5 | 0.5 |
| N-methyl pyrrolidinone ("NMP")[4] | 1.0 | 0.94 | 0.94 |
| Dibutyl tin dilaurate ("DBTDL")[5] | 0.015 | 0.015 | 0.015 |
| PM-1 | 0.08 | — | — |
| CPM-A | — | 0.031 | — |
| CPM-B | — | — | 0.031 |
| Fischer Hardness (N/mm$^2$) | 10 | 12 | 11 |

[1] HDI Biuret BI7960 is a blocked hexamethylene diisocyanate, which is available from Baxenden Chemical Co. of Lancashire, England.
[2] HC-86-7776 is a polyacrylate polymer, which is available from PPG Industries, Inc., of Pittsburgh, Pennsylvania.
[3] PC-1122 is aliphatic carbonate diol, which is available form Stahl USA.
[4,5] Available from Aldrich of Milwaukee, Wisconsin. NMP was biotechnical grade.

The Fischer Microhardness test was performed using a Fischerscope HCV, Model H-100 available from Fischer Technology, Inc. The Fischer microhardness (or "Fischer Hardness"), measured in Newtons per mm$^2$, of the coatings was determined under the conditions of a 100 milliNewton load, 30 load steps and 0.5 second pauses between load steps. The Fischer Hardness data reported herein were measured at an indentor depth of 2 μm.

The photochromic performance of each of the aforementioned coating compositions was performed as follows. The coated lenses prepared above were tested for photochromic response on the Bench for Measuring Photochromics ("BMP") optical bench made by Essilor, Ltd. France. The optical bench was maintained at a constant temperature of 73.4° F. (23° C.) during testing.

Prior to testing on the optical bench, each of the coated lenses were exposed to 365-nanometer ultraviolet light for about 10 minutes at a distance of about 14 centimeters to activate the photochromic materials. The UVA (315 to 380 nm) irradiance at the lens was measured with a Licor Model Li-1800 spectroradiometer and found to be 22.2 watts per square meter. The lens was then placed under a 500 watt, high intensity halogen lamp for about 10 minutes at a distance of about 36 centimeters to bleach (inactivate) the photochromic materials. The illuminance at the lens was measured with the Licor spectroradiometer and found to be 21.4 Klux. The lenses were then kept in a dark environment at room temperature (from 70 to 75° F., or 21 to 24° C.) for at least 1 hour prior to testing on an optical bench. Prior to optical bench measurement, the lenses were measured for ultraviolet absorbance at 390 and 405 nanometers.

The BMP optical bench was fitted with two 150-watt Oriel Model #66057 Xenon arc lamps at right angles to each other. The light path from Lamp 1 was directed through a 3 mm Schott KG-2 band-pass filter and appropriate neutral density filters that contributed to the required UV and partial visible light irradiance level. The light path from Lamp 2 was directed through a 3 mm Schott KG-2 band-pass filter, a Schott short band 400 nm cutoff filter and appropriate neutral density filters in order to provide supplemental visible light illuminance. A 2 inch×2 inch 50% polka dot beam splitter, at 45° to each lamp is used to mix the two beams. The combination of neutral density filters and voltage control of the Xenon arc lamp were used to adjust the intensity of the irradiance. Proprietary software was used on the BMP to control timing, irradiance, air cell and sample temperature, shuttering, filter selection and response measurement. A Zeiss spectrophotometer, Model MCS 501, with fiber optic cables for light delivery through the lens was used for response and color measurement. Photopic response measurements, as well as the response at four select wavelengths, were collected on each lens.

The power output of the optical bench, i.e., the dosage of light that the lens was exposed to, was adjusted to 6.7 Watts per square meter (W/m$^2$) UVA, integrated from 315-380 nm and 50 Klux illuminance, integrated from 380-780 nm. Measurement of the power output was made using the optometer and software contained within the BMP.

Response measurements, in terms of a change in optical density (ΔOD) from the unactivated or bleached state to the activated or colored state were determined by establishing the initial unactivated transmittance, opening the shutter from the Xenon lamp(s) and measuring the transmittance through activation at selected intervals of time. Change in optical density was determined according to the formula: $\Delta OD = \log_{10}(\% Tb/\% Ta)$, where % Tb is the percent transmittance in the bleached state, % Ta is the percent transmittance in the activated state. Optical density measurements were based on photopic optical density.

The results of this testing are presented below in Table 4, wherein the First Fade Half Life ("T½") value is the time interval in seconds for the ΔOD of the activated form of the photochromic material in the coating to reach one half the fifteen-minute ΔOD at 73.4° F. (23° C.), after removal of the activating light source. The Second Fade Half Life ("2T½") value is the time interval in seconds for the ΔOD of the activated form of the photochromic material in the coating to reach one quarter the fifteen-minute ΔOD at 73.4° F. (23° C.), after removal of the activating light source. The Third Half Life ("3T½") value is the time interval in second for ΔOD of the activated form of the photochromic material in the coating to reach one-eighth the fifteen-minute ΔOD at 73.4° F. (23° C.), after removal of the activating light source. Further, the "ΔT¾" value is the time interval in seconds for the bleached form of the photochromic material in the coating to reach three-quarters of the fifteen-minute ΔOD at 73.4° F. (23° C.), after exposure to the activating light source.

TABLE 4

| Response | Example Coating 1 | Comparative Coating A | Comparative Coating B |
| --- | --- | --- | --- |
| T½ (sec) | 207 | 245 | 375 |
| 2T½ (sec) | 453 | 551 | 894 |
| 3T½ (sec) | 727 | 968 | 1743 |
| AT¾ (sec) | 42 | 43 | 63 |

As evident from the results in Table 4, the T½, 2T½, and 3T½ values o Example Coating 1, which contained the photochromic material PM-1 of Example 1, were less than those of either Comparative Coating A or Comparative Coating B, which contained comparative photochromic materials CPM-A and CPM-B, respectively (i.e., the fade rates of Example Coating 1 were faster than that of either Comparative Coating). Additionally, the ΔT¾ value of Example Coating 1 was less than the ΔT¾ activation rate for Comparative Coating B and essentially the same as the ΔT¾ activation rate for Comparative Coating A.

Example 18

Two photochromic coating compositions (indicated as "Example Coating 2" and "Example Coating 4" in Table 5, below) were prepared using example photochromic material PM-2 set forth in Example 2 and example photochromic material PM-4 set forth in Example 4. In addition, two comparative example photochromic coating compositions (indicated as "Comparative Coating C" and "Comparative Coating D" in Table 5 below) were prepared using the comparative photochromic materials CPM-C and CPM-D, respectively.

Comparative photochromic material CPM-C (which is represented by Formula 30 below) was a 3,3-di(4-methoxyphenyl)-6,11,13-trimethyl-13-hydroxy-3H,13H-indeno[2,1-f]naphtho[1,2-b]pyran, which was prepared as set forth in Example 5 of U.S. Pat. No. 5,645,767.

Formula 30

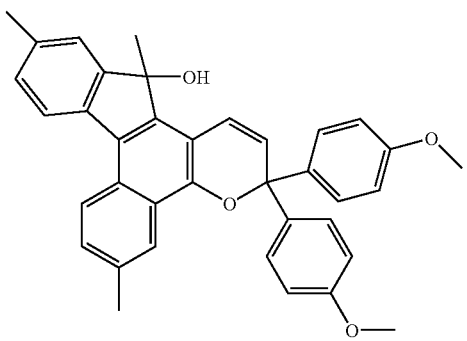

Comparative photochromic material CPM-D was the photochromic material set forth in PART A of Example 2.

Each coating composition was prepared by mixing the components set forth in Table 5 in the listed amounts as set forth above in Example 17. After preparation, each coatings was applied to a plasma treated Gentex PDQ hardcoated plano polycarbonate lens and cured as described above in Example 15, except that spin coating was conducted at 1500 rpm for 5 sec. The components of Example Coating 2 and the comparative coatings were adjusted such that each of the three coatings had essentially the same Fischer Hardness (as indicated in Table 5 below). Example Coating 4 had a higher Fischer Hardness.

TABLE 5

| Component | Amount (g) | | | |
|---|---|---|---|---|
| | Example Coating 2 (53-10) | Comparative Coating C (53-3) | Comparative Coating D (53-2) | Example Coating 4 |
| HDI biuret B17960 | 1.0 | 1.0 | 1.0 | 2.0 |
| HC-86-7726 | 0.5 | 0.5 | 0.5 | 0.64 |
| PC-1122 | 0.5 | 0.5 | 0.5 | 0.19 |
| NMP | 1.0 | 0.94 | 0.94 | 1.74 |
| DBTDL | 0.015 | 0.015 | 0.015 | 0.12 |
| PM-2 | 0.15 | — | — | — |
| CPM-C | — | 0.031 | — | — |
| CPM-D | — | — | 0.031 | — |
| PM-4 | — | — | — | 0.78 |
| Fischer Hardness (N/mm$^2$) | 11 | 14 | 12 | 27 |

Fischer hardness testing and photochromic performance testing were performed on each of the coated lenses as discussed above in Example 17. Additionally, a NMP soak test was performed on the lenses with Example Coating 2 and the two comparative coatings to determine the amount of photochromic material that could be leached from the coating. More specifically, in the NMP soak test, each coating was applied to a hard-coated polycarbonate lenses and cured. Thereafter, each lens was soaked in NMP for 1 hour. The UV absorbance at 390 nm was measured before and after NMP soak. The percent photochromic loss was determined by taking the percent loss in UV absorbance after soaking. NMP was used in this test because the photochromic materials can be extracted into the solvent.

The results of the aforementioned tests are set forth in Table 6 below.

TABLE 6

| Response | Example Coating 2 | Comparative Coating C | Comparative Coating D | Example Coating 4 |
|---|---|---|---|---|
| T½ (sec) | 37 | 54 | 63 | 31 |
| 2T½ (sec) | 94 | 152 | 222 | 67 |
| 3T½ (sec) | — | — | — | 145 |
| ΔT¾ (sec) | 4.6 | 5.9 | 6.6 | 4.3 |
| NMP soak (% photochromic loss) | 0 | 90 | 10 | —* |

*Not tested.

As evident from the results in Table 6, the ΔT¾, T½, and 2T½ values of both Example Coatings 2 and 4, which contained example photochromic material PM-2 (of Example 2) and PM-4 (of Example 4), respectively, were less than ΔT¾, T½ and 2T½ values of either of the comparative coating compositions (i.e., the activation and fade rates of the example coatings were faster than those of the comparative coatings). Further, Example Coating 4, which had a Fischer Hardness at least twice that of the comparative coating compositions, had T½, 2T½ and ΔT¾ values that were less than the comparative coatings. Additionally, during the NMP soak, essentially no leaching of photochromic material from Example Coating 2 was detected after the NMP soak, whereas, leaching of the photochromic materials from comparative coatings was detected.

Example 19

An example photochromic coating composition (indicated as "Example Coating 5" in Table 7, below) was prepared using example photochromic material PM-5 set forth in Example 5. In addition, a comparative example photochromic coating composition (indicated as "Comparative Coating H'" in Table 7 below) was prepared using comparative photochromic material "CPM-H," which photochromic material set forth below in Example 20.

Each coating composition was prepared by mixing the components set forth in. Table 7 in the listed amounts as set forth above in Example 17. After preparation, each coatings was applied to a plasma treated Gentex PDQ hardcoated plano polycarbonate lens and cured as described above in Example 18. The components of Example Coating 5 and Comparative Coating H' were adjusted such that each of the coatings had essentially the same Fischer Hardness (as indicated in Table 7 below).

TABLE 7

| Component | Amount (g) | |
|---|---|---|
| | Example Coating 5 | Comparative Coating H' |
| HDI biuret B17960 | 1.23 | 1.66 |
| HC-86-7726 | 0.71 | 0.71 |
| PC-1122 | — | 0.74 |
| NMP | 1.15 | 1.2 |
| DBTDL | 0.04 | 0.05 |
| PM-5 | 0.74 | — |
| CPM-H | — | 0.11 |
| Fischer Hardness(N/mm$^2$) | 18 | 18 |

Fischer hardness testing and photochromic performance testing were performed on each of the coated lenses as discussed above in Example 17. Additionally, a NMP soak test was performed as discussed above in Example 18.

The results of the aforementioned tests are set forth in Table 8 below.

TABLE 8

| Response | Example Coating 5 | Comparative Coating E |
|---|---|---|
| T½ (sec) | 72 | 70 |
| 2T½ (sec) | 173 | 168 |
| ΔT¾ | 46 | 49 |

As evident from the results in Table 8, the T½, 2T½, and ΔT¾ values of Example Coatings 5, which contained example photochromic material PM-5 (of Example 5) were similar to those of Comparative Coating H', which contained comparative photochromic material CPM-H.

Example 20

The migration performance of the following photochromic materials was tested as follows: two coating composition ("Example Coating 789" and "Comparative Coating FGH") were prepared by mixing the components set forth in Table 9. Example Coating 789 contained three example photochromic materials PM-7, PM-8, and PM-9, which are described above in Examples 7, 8, and 9 respectively. Comparative Coating FGH contained three comparative example photochromic materials (CPM-F, -G, and -H), which were not bonded to the polymeric coating.

Comparative example photochromic material CPM-F was prepared as follows: 7,7-dimethyl-5-hydroxy-7H-benzo[C]fluorene (2.6 g, 0.01 mol) from Step 4 of PART A of Example 7 was dissolved along with 3.5 g (a slight molar excess) of 1-(4-methoxyphenyl-1-(4-morpholinophenyl)-2-propyn-1-ol in 100 ml of toluene. The mixture was stirred at 40° C. and dodecylbenzenesulfonic acid was added drop-wise until a consistent dark color was obtained. After 2 hours, TLC indicated the reaction was largely complete. Thereafter, 300 ml of water was added to the stirred mixture. The organic layer was separated and the solvent removed on a rotary evaporator. The crude product was chromatographed on a silica column using a 2:1 mixture of hexane to ethyl acetate. The photochromic fractions were collected, combined and the solvent removed on a rotary evaporator. The residue was crystallized from methanol to yield 1.8 g of white crystals whose NMR was consistent with the structure 3-(4-methoxyphenyl)-3-(4-morpholinophenyl)-13,13-dimethyl-3H,13H-indeno[2,1-f]naphtho[1,2-b]pyran.

Comparative example photochromic material CPM-G was a prepared as follows: 3,3-di(4-methoxyphenyl)-6-methoxy-7-morpholino-13-ethyl-13-hydroxy-3H,13H-indeno[2,1-f]naphtho[1,2-b]pyran from Step 6 of PART A of Example 8 (68.7 grams), methanol anhydrous (685 mL), toluene (685 mL), and p-toluenesulfonic acid monohydrate (5.1 grams) were combined in a reaction flask and heated to reflux. Additional p-toluenesulfonic acid monohydrate was charged in two 0.5 gram portions; after refluxing for four hours, and then again after eight hours. The reaction mixture was then refluxed overnight. Subsequently, the reaction mixture was cooled to room temperature and diluted with toluene (400 mL). Reaction mixture was washed with 50% saturated aqueous sodium bicarbonate (800 mL). Organic was dried over anhydrous sodium sulfate and concentrated by rotary evaporation. The resulting residue was chromatographed on silica gel (1,300 grams) eluting with 25% ethyl acetate in hexanes. Photochromic fractions were combined and concentrated by rotary evaporation. The resulting residue was recrystallized in 20% hexanes in t-butyl methyl ether yielding 62.6 grams of a tan solid. Mass Spectrometry analysis and the NMR spectrum showed the product to have a structure consistent with 3,3-di(4-methoxyphenyl)-6-methoxy-7-morpholino-13-ethyl-13-methoxy-3H,13H-indeno[2,1-f]naphtho[1,2-b]pyran.

Comparative example photochromic material CPM-H was prepared as follows: 3-(4-fluorophenyl)-3-(4-methoxyphenyl)-6,7-dimethoxy-13-ethyl-13-hydroxy-3H,13H-indeno[2,1-f]naphtho[1,2-b]pyran from Step 3 of PART A of Example 9 (14.9 grams), diethylene glycol monomethyl ether (150 mL), toluene (150 mL), and p-toluenesulfonic acid monohydrate (0.495 grams) were combined in a reaction flask and heated to 95° C. for 6 hours. The reaction mixture was cooled to room temperature and diluted with toluene (150 mL). Reaction mixture was washed with 50% saturated aqueous sodium bicarbonate (200 mL) and four portions of saturated aqueous sodium chloride (175 mL each). The organic layer was dried over anhydrous sodium sulfate and concentrated by rotary evaporation. The resulting residue was chromatographed on silica gel eluting with 25% ethyl acetate in hexanes. Photochromic fractions were collected and concentrated by rotary evaporation. The resulting residue was recrystallized in 20% hexanes in t-butyl methyl ether yielding 9.3 grams of a white crystalline solid. Mass Spectrometry analysis and the NMR spectrum show the product to have a structure consistent with 3-(4-fluorophenyl)-3-(4-methoxyphenyl)-6,7-dimethoxy-13-ethyl-13-(2-(2-methoxyethoxy)ethoxy)-3H,13H-indeno[2,1-f]naphtho[1,2-b]pyran.

Each coating composition was then spun coat onto each of two plasma treated Gentex PDQ hardcoated plano polycarbonate lenses and cured as set forth above in Example 18. One coated lens from each pair of coated lenses was further plasma treated and a protective coating having the composition set forth below in Table 10 was spun over the photochromic coating to a wet film weight of approximately 0.6 grams and cured by UV in a nitrogen atmosphere to a thickness of approximately 10-12 microns. Each of the protective coated lenses was then subjected to a post-bake of 105° C. for 3 hours to simulate the conditions seen during a typical hard-coat curing process.

TABLE 9

| | Amount (g) | |
|---|---|---|
| Component | Comparative Coating 789 | Example Coating FHG |
| HDI biuret BL7960 | 1.0 | 1.5 |
| PC-1122 | 0.5 | — |
| HC-86-7726 | 0.5 | 0.6 |
| NMP | 0.94 | 1.4 |
| DBTDL | 0.015 | 0.09 |
| PM-7 | — | 0.44 |
| PM-8 | — | 0.12 |
| PM-9 | — | 0.24 |
| CPM-F | 0.057 | — |
| CPM-G | 0.032 | — |
| CPM-H | 0.019 | — |

TABLE 10

| Component | Amount in Weight Percent |
|---|---|
| SR-399[6] | 5 |
| SR-350[7] | 30 |
| SR-348[8] | 35 |
| Partially methacrylated bisphenol A diepoxide[9] | 30 |
| SILQUEST ™ A-187[10] | 20 |
| Irgacure 819[11] | 0.1 |
| CD-1011[12] | 4 |

[6]SR-399 is a dipentaerythritol pentaacrylate, which is available from Sartomer Company of Exton, Pennsylvania.
[7]SR-305 is a trimethylolpropane trimethacrylate, which is available from Sartomer Company.
[8]SR-348 is an ethoxylated bisphenol A dimethacrylate, which is available from Sartomer Company.
[9]Obtained from Echo Resins and Laboratories, of Versailles, Missouri as ADME#302.
[10]SILQUEST A-187 is A γ-glycidoxypropyl trimethoxysilane, which is available from Osi Specities of Paris, France.
[11]Irgacure 819 is a bisacrylphosphine oxide photoinitiator, which is available from Ciba-Geigy of Basel, Switzerland.
[12]CD-1011 is a triarylsulfonium hexafluorophosphate cationic photoinitiator, which is available from Sartomer Company.

Photochromic performance testing on each lens in the pair of coated lenses (i.e., with and without the protective coating) was performed as described above in Example 17. The results of this testing are presented below in Table 11.

TABLE 11

| Photochromic Coating | Protective Coating | T½ (sec) | 2T½ (sec) | t = 70% (min) | t = 75% (min) | Abs. at 390 nm |
|---|---|---|---|---|---|---|
| Example Coating 789 | No | 36 | 84 | 2.67 | 3.9 | 1.97 |
| | Yes | 32 | 74 | 2.56 | 4.0 | 2.30 |
| Comparative Coating FGH | No | 41 | 98 | 2.87 | 4.0 | 1.55 |
| | Yes | 41 | 110 | 4.3 | 12.3 | 1.54 |

As evident from Table 11 above, the T½ and 2T½ values of Example Coating 789 coating, both with the protective coating and without the protective coating, were less than those of the Comparative Coating FGH, with and without the protective coating, respectively. Further, as seen in Table 11, the 2T½ value, t=70%, and t=75% values (i.e, the time interval in minutes for the lens to reach 70% and 75% transmittance, respectively) of Example Coating 789 were essentially the same with the protective coating and without the protective coating. This suggests that migration of the photochromic materials, which were bonded to the coating composition, into the relatively hard protective coating in Example Coating 789 was low. In contrast, the t=70% and t=75% values for Comparative Coating FGH were longer with the protective coating than without the protective coating. This suggests that some portion of the comparative photochromic materials of Comparative Coating FGH migrated into the relatively hard protective coating causing deterioration in the photochromic performance of Comparative Coating FGH.

Example 21

The example coatings and comparative coatings set forth in Table 12 below were prepared as described above in Example 17 and coated on lenses as described above in Example 18. Each photochromic coating was formulated to have a Fischer Hardness of approximately 15 N/mm$^2$.

TABLE 12

| Photochromic Coating | HDI biuret BL7960 | PC-1122 | HC-86-7726 | NMP | DBTDL | BYK 333[1] | Photochromic Material |
|---|---|---|---|---|---|---|---|
| Comparative Coating F | 2.5 | 1.25 | 1.25 | 2 | 0.08 | 0.003 | 0.08 g CPM-F |
| Comparative Coating I | 2.5 | 1.25 | 1.25 | 2 | 0.08 | 0.003 | 0.0804 g CPM-I[2] |
| Example Coating 11 | 1.25 | 0.39 | 0.45 | 0.92 | 0.04 | 0.002 | 0.219 g PM-11 |
| Example Coating 7 | 1.25 | 0.04 | 0.45 | 0.92 | 0.04 | 0.002 | 0.183 g PM-7 |
| Comparative Coating H | 2.5 | 1.25 | 1.25 | 2 | 0.08 | 0.003 | 0.0914 g CPM-H |
| Comparative Coating J | 2.5 | 1.25 | 1.25 | 2 | 0.08 | 0.003 | 0.0895 g CPM-J[3] |
| Example Coating 9 | 1.25 | 0.425 | 0.45 | 0.92 | 0.04 | 0.002 | 0.19 g PM-9 |
| Example Coating 12 | 1.25 | 0.39 | 0.45 | 0.92 | 0.04 | 0.002 | 0.219 g PM-12 |
| Comparative Coating G | 2.5 | 1.25 | 1.25 | 2 | 0.08 | 0.003 | 0.0887 g CPM-G |
| Comparative Coating K | 2.5 | 1.25 | 1.25 | 2 | 0.08 | 0.003 | 0.0986 g CPM-K[4] |
| Example Coating 8 | 2.5 | 0.85 | 0.9 | 1.84 | 0.08 | 0.003 | 0.388 g PM-8 |
| Example Coating 10 | 1.25 | 0.39 | 0.45 | 0.92 | 0.04 | 0.002 | 0.232 g PM-10 |

[1]BYK 333 is a polyether modified dimethylpolysiloxane compolymer, which is available from BYK-Chemie of Wallingford, Connecticut.
[2]The photochromic material of PART A of Example 7.
[3]The photochromic material of PART A of Example 9.
[4]The photochromic material of PART A of Example 8.

The number average molecular weight of each of the photochromic materials used in the photochromic coatings listed in Table 12 were determined using GPC or by theoretical calculation as indicated. The T½ and 2T½ fade rates for each of the photochromic coatings listed in Table 12 were measured as discussed above in Example 17. These results are set forth below in Table 13.

TABLE 13

| Photochromic Coating | MW (g/mol.) | T½ (sec) | 2T½ (sec) |
|---|---|---|---|
| Comparative Coating F | 565* | 34 | 78 |
| Comparative Coating I | 595* | 70 | 225 |
| Example Coating 11 | 1300 | 37 | 95 |
| Example Coating 7 | 1800 | 30 | 70 |
| Comparative Coating H | 677* | 61 | 150 |
| Comparative Coating J | 663* | 97 | 315 |
| Example Coating 9 | 2200 | 54 | 130 |
| Example Coating 12 | 3100 | 50 | 117 |
| Comparative Coating G | 656* | 49 | 120 |
| Comparative Coating K | 730* | 77 | 265 |

TABLE 13-continued

| Photochromic Coating | MW (g/mol.) | T½ (sec) | 2T½ (sec) |
|---|---|---|---|
| Example Coating 8 | 2000 | 34 | 78 |
| Example Coating 10 | 3100 | 32 | 75 |

*MW determined by theoretical calculation as rounded.

As evident from Table 13, of the example coatings that contained photochromic materials according to various non-limiting embodiments disclosed herein generally had shorter T½ and 2T½ values (i.e., faster fade rates) than the photochromic coatings that contained the comparative photochromic materials.

Example 22

An example photochromic coating composition (indicated as "Example Coating 13" in Table 14, below) was prepared using example photochromic material PM-13 set forth in Example 13. In addition, two comparative example photochromic coating compositions (indicated as "Comparative Coating L" and "Comparative Coating M" in Table 14 below) were prepared using the comparative photochromic material CPM-L, set forth below, and comparative photochromic material CPM-M, which was the photochromic material set forth in PART A of Example 13, above. Further, the photochromic material PM-13 and CPM-M were each bonded to the polymeric material of their respective coatings (Example Coating 13 and Comparative Coating M); whereas photochromic material CPM-L was not.

Comparative photochromic material CPM-L, which has the structure indicated below in Formula 31, was prepared as set forth in Example 2 of U.S. Pat. No. 5,458,814, at col. 13 line 55 to col. 14 line 7, which example is hereby specifically incorporated by reference herein.

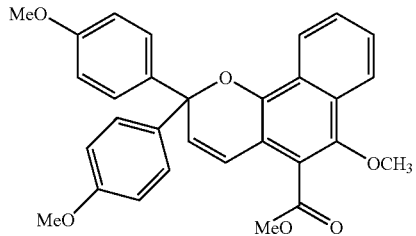

Formula 31

Each coating composition was prepared by mixing the components set forth in Table 14 in the listed amounts as set forth above in Example 17. After preparation, each coatings was applied to a plasma treated Gentex PDQ hardcoated piano polycarbonate lens and cured as described above in Example 18. As indicated in Table 14 below, the components of Example Coating 13 and Comparative Coatings L and M were adjusted such that each of the coatings had essentially the same Fischer Hardness.

TABLE 14

| | Amount (g) | | |
|---|---|---|---|
| Component | Example Coating 5 | Comparative Coating L | Comparative Coating M |
| HDI biuret B17960 | 1.83 | 1 | 1 |
| HC-86-7726 | 0.60 | 0.5 | 0.5 |

TABLE 14-continued

| Component | Amount (g) Example Coating 5 | Amount (g) Comparative Coating L | Amount (g) Comparative Coating M |
|---|---|---|---|
| PC-1122 | — | 0.5 | 0.5 |
| NMP | 1.67 | 0.91 | 0.91 |
| DBTDL | 0.025 | 0.015 | 0.015 |
| PM-13 | 1 | — | — |
| CPM-L | — | 0.14 | — |
| CPM-M | — | — | 0.076 |
| Fischer Hardness (N/mm²) | 12 | 12 | 12 |

Photochromic performance testing was conducted on the coatings discussed above as set forth in Example 17. The results of the photochromic tests are set forth in Table 15 below.

TABLE 15

| Response | Example Coating 13 | Comparative Coating L | Comparative Coating M |
|---|---|---|---|
| T½ (sec) | 75 | 100 | 160 |
| 2T½ (sec) | 230 | 350 | 1100 |

As evident from the results in Table 15, Example Coating 13 had shorter T½ and 2T½ values (i.e., faster fade rates) than either Comparative Coating L or Comparative Coating M.

Example 23

An example photochromic coating composition (indicated as "Example Coating 14" in Table 16, below) was prepared using example photochromic material PM-14 set forth in Example 14. A second example photochromic coating composition (indicated as "Example Coating 2'" in Table 16, below) was prepared using example photochromic material PM-2, set forth in Example 2 above. In addition, a comparative example photochromic coating composition (indicated as "Comparative Coating C'" in Table 14 below) was prepared using the comparative photochromic material CPM-C, set forth above in Example 18.

Each coating composition was prepared by mixing the components set forth in Table 16 in the listed amounts as set forth above in Example 17. After preparation, each coatings was applied to a plasma treated Gentex PDQ hardcoated plano polycarbonate lens and cured as described above in Example 17. As indicated in Table 16 below, the components each coating composition were adjusted such that each of the coatings had essentially the same Fischer Hardness. Both photochromic materials PM-14 and CPM-C were blended in, but not bonded to, the polymeric material of their respective photochromic coating compositions, i.e., Example Coating 14 and Comparative Coating C'. Photochromic material PM-2 was bonded to the polymeric material of Example Coating 2'.

TABLE 16

| Component | Amount (g) Example Coating 14 | Amount (g) Example Coating 2' | Amount (g) Comparative Coating C' |
|---|---|---|---|
| HDI biuret B17960 | 1 | 1.5 | 1 |
| HC-86-7726 | 0.5 | 0.7 | 0.5 |
| PC-1122 | 0.5 | 0.56 | 0.5 |
| NMP | 0.91 | 1.4 | 0.91 |
| DBTDL | 0.015 | 0.02 | 0.015 |
| PM-14 | 0.31 | — | — |
| PM-2 | — | 0.12 | — |
| CPM-C | — | — | 0.05 |
| Fischer Hardness (N/mm²) | 12 | 12 | 13 |

Photochromic performance and NMP soak tests were conducted on the coatings discussed above as set forth in Example 18. The results these tests are set forth in Table 17 below.

TABLE 17

| Response | Example Coating 14 | Example Coating 2' | Comparative Coating C' |
|---|---|---|---|
| T½ (sec) | 31 | 35 | 64 |
| 2T½ (sec) | 120 | 95 | 177 |
| % loss in NMP Soak | 61 | 0 | 55 |

As evident from the results in Table 17, both Example Coatings 14 and 2' had lower T½ and 2T/12 values (i.e., faster fade rates) than Comparative Coating C'. Additionally, no leaching of photochromic material from Example Coating 2' was detected after the NMP soak, whereas, leaching of the photochromic materials from Comparative Coating C' and Example Coating 14 was detected. Further, Example Coating 14, in which the photochromic material was not bonded to the polymer coating, exhibited blooming on curing.

It is to be understood that the present description illustrates aspects of the invention relevant to a clear understanding of the invention. Certain aspects of the invention that would be apparent to those of ordinary skill in the art and that, therefore, would not facilitate a better understanding of the invention have not been presented in order to simplify the present description. Although the present invention has been described in connection with certain embodiments, the present invention is not limited to the particular embodiments disclosed, but is intended to cover modifications that are within the spirit and scope of the invention, as defined by the appended claims.

We claim:

1. A photochromic material comprising a reaction product of:
   (a) at least one ring-opening cyclic monomer chosen from a cyclic ester and a cyclic carbonate; and
   (b) a photochromic initiator.

2. The photochromic material of claim 1 wherein the photochromic material comprises the reaction product of a plurality ring-opening cyclic monomers.

3. The photochromic material of claim 2 wherein each of the plurality of ring-opening cyclic monomers is independently chosen from ε-caprolactone and δ-valerolactone.

4. The photochromic material of claim 1 wherein the photochromic initiator comprises at least one functional group adapted to initiate ring-opening of the at least one ring-opening cyclic monomer, the at least one functional group being chosen from an alcohol, an amine, a carboxylic acid, a silanol, a thiol, and combinations, salts and complexes thereof.

5. The photochromic material of claim 4 wherein the at least one functional group is chosen from a primary alcohol group, a secondary alcohol group, and salts and complexes thereof.

6. The photochromic material of claim 1 wherein at least one ring-opening cyclic monomer is a cyclic ester represented by:

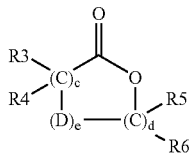

wherein c and d are integers ranging from 1 to 8; and R³, R⁴, R⁵, and FR6 are independently chosen for each (C)$_c$ and (C)$_d$ unit) from —H, —CH₃, C2-C16 alkyl, C(CH₃)₂, and HO—OH₂—; e is 0 or 1; and D is chosen from —O— or —O—C(O); or wherein c is 1, D is —C(R³')(R⁴')—, and R³' and R⁴' come together with R³ and R⁴ to form a fused-aryl, fused-heterocyclic aryl, or fused-cycloaliphatic group.

7. The photochromic material of claim 1 wherein at least one ring-opening cyclic monomer is a cyclic ester chosen from s-caprolactone; t-butyl caprolactone; ζ-enantholactone; δ-valerolactone; a monoalkyl δ-valerolactone; a nonalkyl-, dialkyl-, or trialkyl-ε-caprolactones; β-lactones; γ-lactones; dilactones; and ketodioxanones.

8. The photochromic material of claim 1 wherein at least one ring-opening cyclic monomer is a cyclic carbonate represented by:

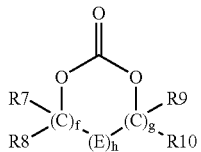

wherein f and g are integers ranging from 1 to 3; R⁷, R⁸, R⁹, R¹⁰ are each independently chosen for each carbon unit from —H, —OH₃, C2-C16 alkyl, C(CH₃)₂, HO—OH₂—, or —OC₆H₅; h is 0 or 1; and E is —O—.

9. The photochromic material of claim 1 wherein the photochromic initiator is a photochromic material chosen from a pyran, an oxazine, and a fulgide.

10. The photochromic material of claim 1 wherein the photochromic initiator is a pyran chosen from a benzopyran, a naphthopyran, a phenanthropyran, a quinolinopyran, a fluoroanthenopyran, and a spiropyran.

11. The photochromic material of claim 1 wherein the photochromic initiator is a naphthopyran chosen from a naphtho[1,2-b]pyran, a naphtho[2,1-b]pyran, an indenonaphthopyran, and a heterocyclic-fused naphthopyran.

12. The photochromic material of claim 1 wherein the photochromic initiator is chosen from:

(1) 3,3-di(4-methoxyphenyl)-6,7-dimethoxy-13-methyl-13-(2-(2-hydroxyethoxy)ethoxy)-3H, 13H-indeno[2,1-f]naphtho[1,2-b]pyran;

(2) 3,3-d (4-methoxyphenyl)-6-methoxy-7-((3-hydroxymethyl)piperidinyl)-13-ethyl-13-(2-(2-hydroxyethoxy)ethoxy)-3H, 13H-indeno[2,1-f]naphtho[1,2-b]pyran;

(3) 3-(4-(2-hydroxyethoxy)phenyl)-3-(4-fluorophenyl)-6,7-dimethoxy-13-ethyl-13-(2-(2-hydroxyethoxy)ethoxy)-3H, 13H-indeno[2,1-f]naphtho[1,2-b]pyran;

(4) 3-phenyl-3-(4-(2-hydroxyethoxy)phenyl)-6-methoxy-7-(3-methylpiperidinyl)-13,13-dimethyl-3H, 13H-indeno[1,2-b]pyran:

(5) 3-(4-methoxyphenyl)-3-(4-fluorophenyl)-6-methoxy-7-(piperidino)-13-butyl-13-(2-(2-hydroxyethoxy)ethoxy)-3H, 13H-indeno[2,1-f]naphtho[1,2-b]pyran;

(6) 3-phenyl-3-(4-(2-hydroxyethoxy)phenyl)-6-methoxy-7-piperidino-13,13-dimethyl-3H, 13H-indeno[2,1-f]naphtho[1,2-b]pyran;

(7) 3-phenyl-3-(4-methoxyphenyl)-6,11-dimethoxy-13-(2-hydroxyethyl)-3H, 13H-indeno[2,1-f]naphtho[1,2-b]pyran;

(8) 3-phenyl-3-(4-morpholinophenyl)-6,7-dimethoxy-13-hydroxymethyl-13-(2-hydroxyethyl)-3H, 13H-indeno[2,1-f]naphtho[1,2-b]pyran;

(9) 3-(4-methoxyphenyl)-3-(4-morpholinophenyl)-6-methoxy-7-pyrrolidino-13-ethyl-13-(2-(2-hydroxyethoxy)ethoxy)-3H, 13H-indeno[2,1-f]naphtho[1,2-b]pyran;

(10) 3-(4-methoxyphenyl)-3-(4-fluorophenyl)-6-methoxy-7-morpholino-13-ethyl-13-(2-(2-hydroxyethoxy)ethoxy)-3H, 13H-indeno[2,1-f]naphtho[1,2-b]pyran;

(11) 3,3-di-(4-methoxyphenyl)-13-propyl-13-hydroxymethyl-3H, 13H-indeno[2,1-f]naphtho[1,2-b]pyran;

(12) 3,3-di(4-methoxyphenyl)-6,7-dimethoxy-11-fluoro-13-butyl-13-(2-(2-hydroxyethoxy)ethoxy)-3H, 13H-indeno[2,1-f]naphtho[1,2-b]pyran;

(13) 3-phenyl-3-(4-(2-hydroxyethoxy)phenyl)-6,11-dimethoxy-3H, 13H-indeno[2,1-f]naphtho[1,2-b]pyran;

(14) 3,3-di(4-methoxyphenyl)-6,7-dimethoxy-13-hydroxymethyl-13-(2-hydroxyethyl)-3H, 13H-indeno[2,1-f]naphtho[1,2-b]pyran;

(15) 3-phenyl-3-(4-(2-hydroxyethoxy)phenyl)-6,11-dimethyl-3H, 13H-indeno[2,1-f]naphtho[1,2-b]pyran;

(16) 3-phenyl-3-(4-methoxyphenyl)-6,11-dimethoxy-13-ethyl-13-(2-(2-hydroxyethoxy)ethoxy)-3H, 13H-indeno[2,1-f]naphtho[1,2-b]pyran;

(17) 3,3-di-(4-methoxyphenyl)-6,11,13-trimethyl-13-(2,2-di(hydroxymethyl)butoxy-3H, 13H-indeno[2,1-f]naphtho[1,2-b]pyran;

(18) 2,2-di(4-methoxyphenyl)-5-methoxycarbonyl-6-(2-hydroxyethoxy)-[2H]-naphtho[1,2-b]pyran;

(19) 3-phenyl-3-(4-(2-hydroxyethoxy)phenyl)-6,11-dimethoxy-13,13-dimethyl-3H, 13H-indeno[2,1-f]naphtho[1,2-b]pyran;

(20) 3-phenyl-3-(4-methoxyphenyl)-6-methoxy-7-((3-hydroxymethyl)piperidno)-13,13-dimethyl-3H, 13H-indeno[2,1-f]naphtho[1,2-b]pyran;

(21) 3-(4-methoxyphenyl)-3(4-morpholin-1-yl-phenyl)-6,11-dimethyl-13-butyl-13-(2-(2-(2-hydroxyethoxy)ethoxy)ethoxy)-3H, 13H-indeno[2,1-f]naphtho[1,2-b]pyran;

(22) 3-phenyl-3-(4-(2-hydroxyethoxy)phenyl)-6-methoxy-7-(morpholino)-13,13-dimethyl-3H, 13H-indeno[2,1-f]naphtho[1,2-b]pyran;

(23) 3-phenyl-3-(4-(2-hydroxyethoxy)phenyl)-6,7-dimethoxy-13,13-dimethyl-3H,13H-indeno[2,1-]naphtho[1,2-b]pyran;

(24) 3-(4-methoxyphenyl)-3-(4-fluorophenyl)-6-methoxy-7-((4-hydroxymethyl)piperidino)-13,13-dimethyl-3H, 13H-indeno[2,1-f]naphtho[1,2-b]pyran;

(25) 3,3-di(4-methoxyphenyl)-6-methoxy-7-(piperidin-1-yl)-13-butyl-13-(2-(2-hydroxyethoxy)ethoxy)-3H, 13H-indeno[2,1-f]naphtho[1,2-b]pyran;

(26) 3,3-di(4-methoxyphenyl)-6,11-dimethyl-13-hydroxymethyl-13-(2-hydroxypropyl)-3H, 13H-indeno[2,1-f]naphtho[1,2-b]pyran;

(27) 3-phenyl-3-(4-morpholinophenyl)-6-methoxy-7-((3-hydroxymethyl)piperidino)-13,13-dimethyl-3H, 13H-indeno[2,1-f]naphtho[1,2-b]pyran;

(28) 3-(4-methoxyphenyl)-3-(4-fluorophenyl)-6-methoxy-7-(morpholin-1-yl)-13-butyl-13-(2-(2-hydroxyethoxy)ethoxy)-3H, 13H-indeno[2,1-f]naphtho[1,2-b]pyran;

(29) 3-(4-fluorophenyl)-3-(4-(2-hydroxyethoxy)phenyl)-13,13-dimethyl-3H, 13H-indeno[2,1-f]naphtho[1,2-b]pyran;

(30) 2,2-di(4-methoxyphenyl)-5-(2-(2-hydroxyethoxy)ethoxycarbonyl)-6-phenyl-[2H]-naphtho[1,2-b]pyran;

(31) 3-(4-fluorophenyl)-3-(4-methoxyphenyl)-6,7-dimethoxy-13-ethyl-13-(2-(2-hydroxyethoxy)ethoxy)-3H, 13H-indeno[2,1-f]naphtho[1,2-b]pyran;

(32) 3,3-di(4-methoxyphenyl)-6-methoxy-7-morpholino-13-ethyl-13-(2-(2-hydroxyethoxy)ethoxy)-3H, 13H-indeno[2,1-f]naphtho[1,2-b]pyran;

(33) 3-(4-morpholinophenyl)-3-phenyl-6,7-dimethoxy-13-butyl-13-(2-(2-(2-hydroxyethoxy)ethoxy)ethoxy)-3H, 13H-indeno[2,1-f]naphtho[1,2-b]pyran;

(34) 3-(4-fluorophenyl)-3-(4-(3-hydroxymethyl)piperidinophenyl)-6-methoxy-7-hydroxy-13,13-dimethyl-3H, 13H-indeno[2,1-f]naphtho[1,2-b]pyran:

(35) 3-(4-morpholinophenyl)-3-phenyl-6,7-dimethoxy-13-ethyl-13-(2-(2-hydroxyethoxy)ethoxy)-3H, 13H-indeno[2,1-f]naphtho[1,2-b]pyran;

(36) 2,2-diphenyl-5-hydroxymethyl-8-methyl-2H-naphtho[1,2-b]pyran;

(37) 3-(4-(2-hydroxyethoxy)phenyl)-3-(4-morpholinophenyl)-13,13-dimethyl-3H, 13H-indeno[2,1-f]naphtho[1,2-b]pyran;

(38) 3-(4-(2-hydroxyethoxy)phenyl)-3-phenyl-13,13-dimethyl-3H, 13H-indeno[2,1-f]naphtho[1,2-b]pyran;

(39) 2,2-diphenyl-5-(2-(2-hydroxyethoxy)ethoxycarbonyl)-8,9-dimethoxy-2H-naphtho[1,2-b]pyran;

(40) 3,3-di(4-fluorophenyl)-6,7-dimethoxy-13-butyl-13-(2-(2-(2-hydroxyethoxy)ethoxy)ethoxy)-3H, 13H-indeno[2,1-f]naphtho[,2-b]pyran;

(41) 3-(4-fluorophenyl)-3-(4-methoxyphenyl)-6,7-dimethoxy-13-ethyl-13-(2-(2hydroxyethoxy)ethoxy)ethoxy)-3H, 13H-indeno[2,1-f]naphtho[1,2-b]pyran;

(42) 2,2-diphenyl-5-methoxycarbonyl-6-phenyl-9-(2-hydroxyethoxy)-2H-naphtho[1,2-b]pyran;

(43) 3,3-di(4-methoxyphenyl)-6,7-dimethoxy-13-ethyl-13-(2-(2-(2-hydroxyethoxy)ethoxy)ethoxy)-3H, 13H-indeno[2,1-f]naphtho[1,2-b]pyran;

(44) 3-(4-methoxyphenyl)-3-phenyl-6,11-dimethoxy-13-(2-(2-hydroxyethoxy)ethoxy)-3H, 13H-indeno[2,1-f]naphtho[1,2-b]pyran;

(45) 3-(4-(2-hydroxyethyl)piperazinophenyl)-3-phenyl-13,13-dimethyl-3H, 13H-indeno[2,1-f]naphtho[1,2-b]pyran;

(46) 2,2-di(4-methoxyphenyl)-5-(2-hydroxyethoxy)carbonyl-6-phenyl-2H-naphtho[1,2-b]pyran;

(47) 3-(4-morpholinophenyl)-3-phenyl-13-ethyl-13-(2-(2-(2-hydroxyethoxy)ethoxy)ethoxy)-3H, 13H-indeno[2,1-f]naphtho[1,2-b]pyran;

(48) 3,3-di(4-methoxyphenyl)-6-methoxy-7-(3-hydroxymethyl)piperidinophenyl)-13,13-dimethyl-3H, 13H-indeno[2,1-f]naphtho[1,2-b]pyran;

(49) 3,3-di(4-methoxyphenyl)-6,11,13-trimethyl-13-(2-(2-(2-hydroxyethoxy)ethoxy)ethoxy)-3H, 13H-indeno[2,1-f]naphtho[1,2-b]pyran;

(50) 2,2-diphenyl-5-(2-(2-hydroxyethoxy)ethoxycarbonyl)-6-(4-methoxy)phenyl-9-methoxy-2H-naphtho[1,2-b]pyran;

(51) 2,2-diphenyl-5-hydroxymethyl-7,8-dimethoxy-2H-naphtho[1,2-b]pyran;

(52) 3,3-di(4-methoxyphenyl)-6,11,13-trimethyl-13-(10-hydroxydecoxy)-3H, 13H-indeno[2,1-f]naphtho[1,2-b]pyran;

(53) 2,2di(4-methoxyphenyl)-5-methoxycarbonyl-6-(4-(2-hydroxyethoxy)phenyl-2H-naphtho[1,2-b]pyran;

(54) 3,3-di(4-methoxyphenyl)-6,11-dimethoxy-13-(2-hydroxyethoxy)-3H, 13H-indeno[2,1-f]naphtho[1,2-b]pyran;

(55) 3-phenyl-3-(4-morpholinophenyl)-6,11-dimethoxy-13-(2-hydroxyethoxy)-3H, 13H-indeno[2,1-f]naphtho[2-b]pyran;

(56) 2,2-di(4-methoxyphenyl)-5-methoxycarbonyl-6-phenyl-9-(2-hydroxyethoxy)-2H-naphtho[1,2-b]pyran;

(57) 3,3-di(4-methoxyphenyl)-6,11-dimethyl-13-hydroxy-13-(2-hydroxyethyl)-3H, 13H-indeno[2,1-f]naphtho[1,2-b]pyran;

(58) 3,3-di(4-methoxyphenyl)-6,11,13-trimethyl-13-(5-hydroxypentoxy)-3H, 13H-indeno[2,1-f]naphtho[1,2-b]pyran;

(59) 3,3-di(4-methoxyphenyl)-11-(2-hydroxyethoxy)-13,13-dimethyl-3H, 13H-indeno[2,1-f]naphtho[1,2-b]pyran;

(60) 3,3-di(4-methoxyphenyl)-6,11-dimethyl-13-hydroxy-13-(3-hydroxypropyl)-3H, 13H-indeno[2,1-f]naphtho[1,2-b]pyran;

(61) 3,3-di(4-methoxyphenyl)-6,11-dimethyl-13-(2-hydroxyethoxy)-3H, 13H-indeno[2,1-f]naphtho[1,2-b]pyran;

(62) 3-phenyl-3-(4-methoxyphenyl)-6,11-dimethoxy-13-methyl-13-(2-(2-hydroxyethoxy)ethoxy)-3H, 13H-indeno[2,1-f]naphtho[1,2-b]pyran;

(63) 3,3-di(4-methoxyphenyl)-6,11-dimethyl-13-hydroxy-13-hydroxymethyl)-3H, 13H-indeno[2,1-f]naphtho[1,2-b]pyran;

(64) 3,3-di(4-methoxyphenyl)-6,11-dimethoxy-13-(2-(2-hydroxyethoxy)ethoxy)-3H, 13H-indeno[2,1-f]naphtho[1,2-b]pyran;

(65) 3,3-di(4-methoxyphenyl)-6,11-dimethoxy-13-methyl-13-(2-(2-hydroxyethoxy)ethoxy)-3H, 13H-indeno[2,1-f]naphtho[2-b]pyran;

(66) 2,2-diphenyl-5-(2,3-dihydroxy)propoxycarbonyl-8-methyl-2H-naphtho[1,2-b]pyran;

(67) 3,3-di(4-methoxyphenyl)-6,11-dimethoxy-13-hydyoxy- 13-(4-hydroxybutyl)-3H, 13H-indeno[2,1-f]naphtho[1,2-b]pyran;

(68) 5,5-di(4-(2-(2-hydroxyethoxy)ethoxy)ethoxy)phenyl)-8-(3-chloropropoxy)carbonyl-5H-fluorantheno[3,2-b]pyran;

(69) 3,3-di(4-methoxyphenyl)-6,11-dimethoxy-13-butyl-13-(2-(2-hydroxyethoxy)ethoxy)-3H, 13H-indeno[2,1-f]naphtho[1,2-b]pyran;

(70) 3,3-di(4-methoxyphenyl)-6,11-dimethoxy-13-hydroxy-13-(3-hydroxypropyl)-3H, 13H-indeno[2,1-f]naphtho[1,2-b]pyran;

(71) 3-phenyl-3-(4-morpholinophenyl)-13-methyl-13-(2,3-dihydroxypropoxy)-3H, 13H-indeno[2,1-f]naphtho[1,2-b]pyran;
(72) 3,3-di(4-methoxyphenyl)-6,11,13-trimethyl-13-(2,3-dihydroxypropoxy)-3H, 13H-indeno[2,1-f]naphtho[1,2-b]pyran;
(73) 3,3-di(4-methoxyphenyl)-6,11-dimethoxy-13-methyl-13-(2,3-dihydroxypropoxy)-3H, 13H-indeno[2,1-f]naphtho[2-b]pyran;
(74) 3,3-di(4-methoxyphenyl)-6,11,13-trimethyl-13-(2-hydroxyethoxy)-3H, 13H-indeno[2,1-f]naphtho[1,2-b]pyran;
(75) 2-(4-(2-(2-hydroxyethoxy)ethoxy)ethoxy)phenyl-2-phenyl-5-methoxycarbonyl-6-methyl-9-methoxy-2H-naphtho[1,2-b]pyran;
(76) 3,3-di(4-methoxyphenyl)-6,11,13-trimethyl-13-(2-(2,2-bis[2-hydroxyethoxy)methyl]-3-hydroxypropyloxy)ethoxy)-3H 13H-indeno[2,1-f]naphtho[2-b]pyran;
(77) 3,3-di(4-methoxyphenyl)-6,11,13-trimethyl-13-(2-(2-(2-(2-(2-hydroxyethoxy)ethoxy)ethoxy)ethoxy)ethoxy)-3H, 13H-indeno[2,1-f]naphtho[1,2-b]pyran;
(78) 2,2-diphenyl-5-(2-(2-hydroxyethoxy)ethoxyoarbonyl)-8-methyl-2H-naphtho[1,2-b]pyran;
(79) 3,3-di(4-methoxyphenyl)-6,11,13-trimethyl-13-(2-(2-(2-(2hydroxyethoxy)ethoxy)ethoxy)ethoxy)-3H, 13H-indeno[2,1-f]naphtho[1,2-b]pyran;
(80) 3,3-di(4-methoxyphenyl)-6,11,13-trimethyl-13-(2-(2-hydroxyethoxy)ethoxy)-3H, 13H-indeno[2,1-f]naphtho[1,2-b]pyran;
(81) 2,2-di(4-methoxyphenyl)-5-(2-(2-(2-hydroxyethoxy)ethoxy)ethoxycarbonyl)-6-phenyl-2H-naphtho[1,2-b]pyran;
(82) 2,2-di(4-methoxyphenyl)-5-methoxycarbonyl-6-(2-hydroxyethoxy)ethoxy-2H-naphtho[1,2-b]pyran;
(83) 2,2di(4-methoxyphenyl)-5-(2-(2-(2-(2-hydroxyethoxy)ethoxy)ethoxy)ethoxycarbonyl)-6-phenyl-2H-naphtho[2-b]pyran;
(84) 2,2-di(4-methoxyphenyl)-5-hydroxy-6-(2-hydroxyphenyl)-2H-naphtho[2-b]pyran.

13. A photochromic composition comprising:
(a) a polymeric material; and
(b) at least one photochromic material in contact with at least a portion of the polymeric material, the at least one photochromic material comprising a reaction product of
    (1) at least one ring-opening cyclic monomer chosen from a cyclic ester and a cyclic carbonate; and
    (2) a photochromic initiator.

14. The photochromic composition of claim 13 wherein a fade rate of the at least one photochromic material when bonded to the polymeric material is equal to or faster than a fade rate of a corresponding photochromic material that lacks a residue of a cyclic monomer when bonded to the polymeric material.

15. The photochromic composition of claim 14 wherein a T½ value of the at least one photochromic material when bonded to the polymeric material is no greater than a T½ value of a corresponding photochromic material that does not comprise a residue of a cyclic monomer bonded to the polymeric material.

16. The photochromic composition of claim 14 wherein a T½ value of the at least one photochromic material when bonded to the polymeric material is less than a T½ value of a corresponding photochromic material that does not comprise a residue of a cyclic monomer bonded to the polymeric material.

17. The photochromic composition of claim 13 wherein the polymeric material is chosen from polymeric microparticles; copolymers of ethylene and vinyl acetate; copolymers of ethylene and vinyl alcohol; copolymers of ethylene, vinyl acetate, and vinyl alcohol; cellulose acetate butyrate, poly(urethane); poly(acrylate); poly(methacrylate); epoxies; aminoplast functional polymers; poly(anhydride); poly(urea urethane); N-alkoxymethyl(meth)acrylamide functional polymers; poly(siloxane); and poly(silane).

18. The photochromic composition of claim 13 wherein the at least one photochromic material is blended with at least a portion of the polymeric material.

19. The photochromic composition of claim 13 wherein the at least one photochromic material is bonded to at least a portion of the polymeric material.

20. A photochromic composition comprising:
(a) a polymeric material; and
b) at least one photochromic material bonded to at least a portion of the polymeric material, the at least one photochromic material comprising
    (1) a photochromic group, and
    (2) at least one segment formed by ring-opening polymerization and comprising the residue of a plurality of ring-opening cyclic monomers bonded to the photochromic group, the ring-opening cyclic monomers being chosen from cyclic esters, cyclic carbonates, cyclic ethers, cyclic siloxanes, and combinations thereof, wherein the at least one segment has a number average molecular weight of at least 1000 g/mol.; and wherein the photochromic material when bonded to the polymeric material has a T½ value that is no greater than T½ value of a corresponding photochromic material that lacks a segment comprising the residue of a plurality of ring-opening cyclic monomers.

21. A method of making a photochromic composition comprising: connecting at least one photochromic material to at least a portion of a polymeric material, wherein the at least one photochromic material comprises a reaction product of:
(1) at least one ring-opening cyclic monomer chosen from a cyclic ester and a cyclic carbonate; and
(2) a photochromic initiator.

* * * * *